United States Patent
Brosnan et al.

(10) Patent No.: US 11,938,067 B2
(45) Date of Patent: Mar. 26, 2024

(54) PATIENT CONTAINMENT SYSTEMS FOR USE WITH PATIENT TRANSPORT APPARATUSES

(71) Applicant: Stryker Corporation, Kalamazoo, MI (US)

(72) Inventors: Daniel V. Brosnan, Kalamazoo, MI (US); Melvin Gottschalk, Jr., Byron Center, MI (US); Zachary Baker, Scotts, MI (US); Scott I. Biba, Waunakee, WI (US); Erik P. Eagleman, Madison, WI (US); Cory P. Herbst, Shelbyville, MI (US); Nathan W. Matheny, Portage, MI (US); Trey Thomas Pfeiffer, Portage, MI (US); Kelly Sandmeyer, Mattawan, MI (US); Jeffrey R. Staszak, Deerfield, WI (US); John Wallace, Troy, MI (US); James K. Galer, Byron Center, MI (US); James Robert Tumavich, Jr., Kalamazoo, MI (US); Kevin M. Patmore, Plainwell, MI (US); Scott Zufall, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 477 days.

(21) Appl. No.: 17/131,954

(22) Filed: Dec. 23, 2020

(65) Prior Publication Data

US 2021/0196535 A1 Jul. 1, 2021

Related U.S. Application Data

(60) Provisional application No. 62/954,879, filed on Dec. 30, 2019.

(51) Int. Cl.
*A61G 5/10* (2006.01)
*A61G 3/08* (2006.01)

(52) U.S. Cl.
CPC ............. *A61G 3/0808* (2013.01); *A61G 5/10* (2013.01); *A61G 2200/34* (2013.01); *A61G 2203/70* (2013.01); *A61G 2205/00* (2013.01)

(58) Field of Classification Search
CPC ............................. A61G 3/0808; A61G 5/10
(Continued)

(56) References Cited

U.S. PATENT DOCUMENTS

| 6,648,343 | B2* | 11/2003 | Way ...................... A61G 5/061 280/5.22 |
| 8,936,155 | B2* | 1/2015 | Ravary ...................... G09F 3/14 206/451 |

(Continued)

OTHER PUBLICATIONS

American Quality Health Products, "Karman XO-505 Power Standing Wheelchair Wepage", https://americanqualityhealthproducts.com/all-power-chairs/3944-xo-505-standing-wheelchair-w-multiple-power-functions-by-karman.html#/, 2019, 11 pages.

(Continued)

*Primary Examiner* — Hilary L Gutman
(74) *Attorney, Agent, or Firm* — Howard & Howard Attorneys PLLC

(57) ABSTRACT

A patient containment system for securing a patient to a patient transport apparatus, comprising a first lower strap and a second lower strap. Each of the first lower strap and the second lower strap have a thigh region, a waist region, and a connection region arranged between the thigh region and the waist region. A first connector is coupled to the connection region of the first lower strap. A second connector is coupled to the connection region of the second lower strap, and is configured to releasably attach to the first connector to at least partially limit movement of the first (Continued)

lower strap relative to the second lower strap. The connection region defines a connection width, and the thigh region defines a thigh width larger than the connection width.

19 Claims, 38 Drawing Sheets

(58) Field of Classification Search
USPC .................................................... 296/65.06
See application file for complete search history.

(56) References Cited

U.S. PATENT DOCUMENTS

| | | | | |
|---|---|---|---|---|
| 10,080,693 | B1* | 9/2018 | Scheenstra | A61G 1/044 |
| 10,130,529 | B2* | 11/2018 | Gale | A61G 3/0808 |
| 10,723,242 | B2* | 7/2020 | De Rico Herrero | ........................ B60N 2/01583 |
| 2005/0214088 | A1* | 9/2005 | Acton | A61G 3/0808 280/801.1 |
| 2016/0338886 | A1* | 11/2016 | Schroeder | A61G 1/044 |
| 2019/0274920 | A1* | 9/2019 | Williams | A61H 1/00 |
| 2020/0268576 | A1* | 8/2020 | Scheenstra | A44B 11/2557 |
| 2020/0298792 | A1* | 9/2020 | Eaton | B60N 2/2884 |
| 2021/0128374 | A1* | 5/2021 | Esteireiro | B60R 22/30 |

OTHER PUBLICATIONS

EA Medical, LLC, "BEAR-iatrics Bariatric Equalizing Abdominal Restraint (B.E.A.R.) Webpage", https://www.eamed.com/products/ems/bear-latrics,m, 2019, 2 pages.
Ferno, "Patient Restrainst Systems Webpage", http://www.ferno.com.au/products/emergency-and-rescue/patient-handling/patient-restraint-systems, 2019, 5 pages.
Ferno, "414-R Side Arm Wrist Restraints Webpage", http://www.ferno.com.au/products/mortuary/stretcher-accessories-and-locks/ferno-414-r-sidearm-wrist-restraints, 2019, 2 pages.
Ferno, "EZ-Glide Stair Chair Webpage", https://fernoems.com/stair-chairs/ez-glide-stair-chair-(1), 2019, 8 pages.
Ferno, "Ferno Power X1 Webpage", https://fernoems.com/ambulance-cots/power-x1?hl=en-us, 2019, 12 pages.
Ferno, "Image of Ferno INX", http://www.ferno.com.au/getattachment/1c343c37-13a4-4572-8466-222922d0ed4e/img_er_INX-arms_hi, 2019, 1 page.
Ferno, "Image of Ferno Power X", http://www.ferno.com.au/getattachment/3d770919-949a-45a6-868f-43009806ce69/img_er power-x_hi, 2019, 1 page.
Ferno, "Model 414-OL Over the Lap Restraints", http://www.ferno.com.au/products/mortuary/stretcher-accessories-and-locks/ferno-414-ol-over-the-lap-wrist-restraints, 2019, 2 pages.
Ferno, "Universal Patient Restraint Set Webpage", 2019, http://www.ferno.com.au/products/emergency-and-rescue/patient-handling/patient-restraint-systems/universal-psychiatric-restraint-set, 2019, 3 pages.
Ferno,"Model 35X Series ProFLEXX User's Manual", Aug. 2013, 35 pages.
Quadmed, Inc., "BEAR-iatrics Inc.—Bariatric Equalizing Abdominal Restraint Webpage", https://www.quadmed.com/product/bear-abdominal-restraint, 2019, 5 pages.
Stryker, "Power-Pro XT Operations/Maintenance Manual", 6506-109,001 Rev E, Jun. 2015, 238 pages.
Stryker, "Stair-Pro Stair Chair Webpage",https://www.stryker.com/us/en/emergency-care/products/stair-pro.html, 2019, 3 pages.
Stryker, "XPS Siderail System Webpage", 2019,https://www.stryker.com/us/en/emergency-care/products/xps-siderails.html, 2019, 3 pages.
The Q Blog, "Featuring the ACR4 Ambulance Child Restraint from Quantum EMS! Webpage", http://emsproducts.blogspot.com/2016/09/featuring-acr4-ambulance-child.html?_sm_au_=iVV6q1jk51VM0W0r, Sep. 23, 2016, 2 pages.

* cited by examiner

PATIENT CONTAINMENT SYSTEMS FOR USE WITH PATIENT TRANSPORT APPARATUSES

CROSS-REFERENCE TO RELATED APPLICATION

This application claims priority to and all the benefits of U.S. Provisional Patent Application No. 62/954,879, filed on Dec. 30, 2019.

BACKGROUND

In many instances, patients with limited mobility may have difficulty traversing stairs without assistance. In certain emergency situations, traversing stairs may be the only viable option for exiting a building. In order for a caregiver to transport a patient along stairs in a safe and controlled manner, a stair chair or evacuation chair may be utilized. Stair chairs are adapted to transport seated patients either up or down stairs, with two caregivers typically supporting, stabilizing, or otherwise carrying the stair chair with the patient supported thereon.

Typically, caregivers will secure the patient to the stair chair using an arrangement of straps, harnesses, and the like, which may be adjustable to conform to different patient body types. These conventional straps tend to be difficult to route when used with certain types of patients (e.g., pediatric or bariatric patients), and can cause patient discomfort.

A patient containment system that addresses one or more of the aforementioned challenges is desired.

BRIEF DESCRIPTION OF THE DRAWINGS

Other advantages of the present invention will be readily appreciated as the same becomes better understood by reference to the following detailed description when considered in connection with the accompanying drawings.

DETAILED DESCRIPTION OF THE EMBODIMENTS

Figure 1:
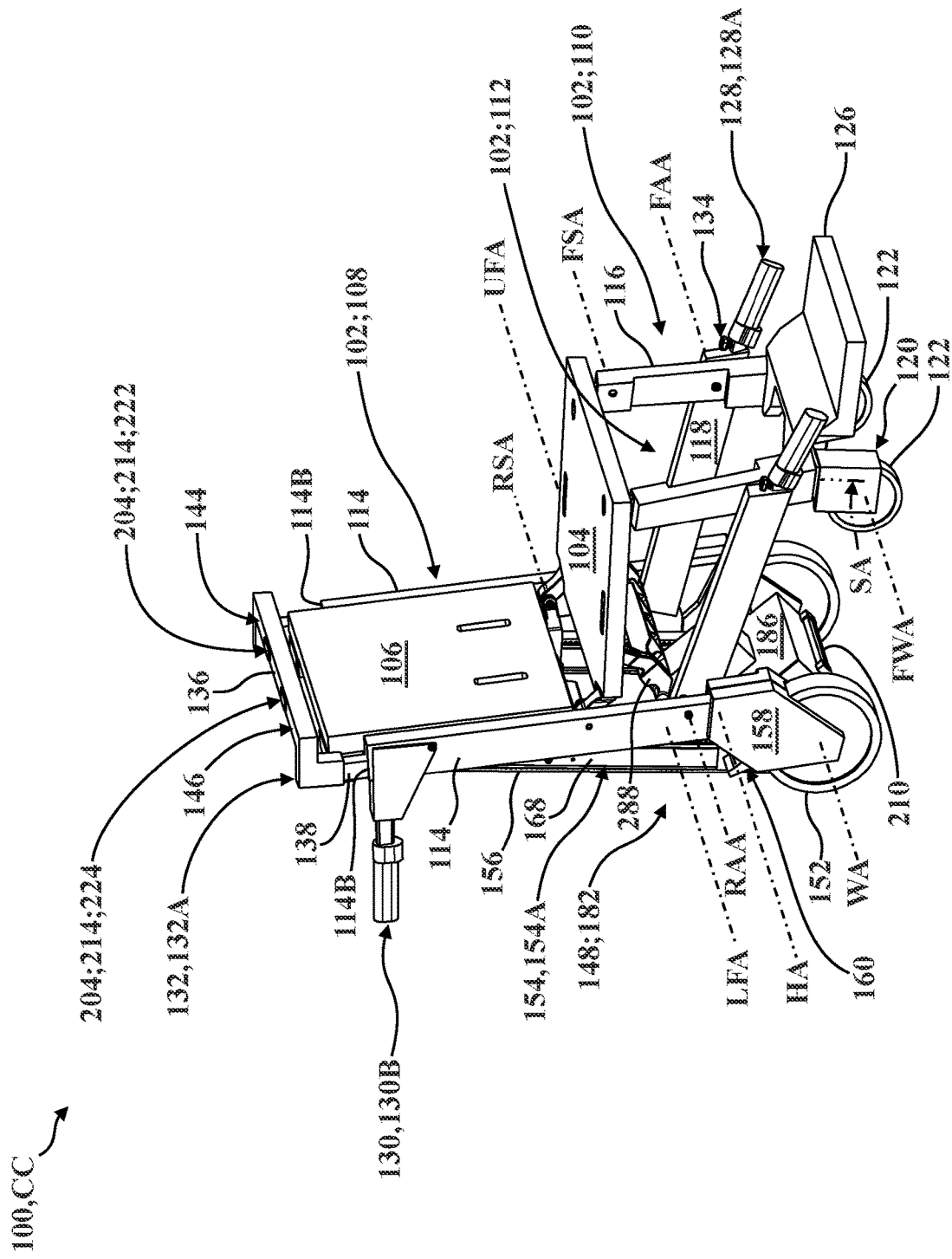
FIG. 1 is a front perspective view of a patient transport apparatus according to the present disclosure, shown arranged in a chair configuration for supporting a patient for transport along a floor surface, and shown having a track assembly disposed in a retracted position, and a handle assembly disposed in a collapsed position.

Referring now to the drawings, wherein like numerals indicate like parts throughout the several views, the present disclosure is generally directed toward a patient transport apparatus 100 configured to allow one or more caregivers to transport a patient. To this end, the patient transport apparatus 100 is realized as a "stair chair" which can be operated in a chair configuration CC (see FIGS. 1 and 6A) to transport the patient across ground or floor surfaces FS (e.g., pavement, hallways, and the like), as well as in a stair configuration SC (see FIGS. 2 and 6B) to transport the patient along stairs ST. As will be appreciated from the subsequent description below, the patient transport apparatus 100 of the present disclosure is also configured to be operable in a stowed configuration WC (see FIG. 5) when not being utilized to transport patients (e.g., for storage in an ambulance).

As is best shown in FIG. 1, the patient transport apparatus 100 comprises a support structure 102 to which a seat section 104 and a back section 106 are operatively attached. The seat section 104 and the back section 106 are each shaped and arranged to provide support to the patient during transport. The support structure 102 generally includes a rear support assembly 108, a front support assembly 110, and an intermediate support assembly 112 that is. The back section 106 is coupled to the rear support assembly 108 for concurrent movement. To this end, the rear support assembly 108 comprises rear uprights 114 which extend generally vertically and are secured to the back section 106 such as with fasteners (not shown in detail). The rear uprights 114 are spaced generally laterally from each other in the illustrated embodiments, and are formed from separate components which cooperate to generally define the rear support assembly 108. However, those having ordinary skill in the art will appreciate that other configurations are contemplated, and the rear support assembly 108 could comprise or otherwise be defined by any suitable number of components. The front support assembly 110 comprises front struts 116 which, like the rear uprights 114, are spaced laterally from each other and extend generally vertically. The intermediate support assembly 112 comprises intermediate arms 118 which are also spaced laterally from each other. Here too, it will be appreciated that other configurations are contemplated, and the front support assembly 110 and/or the intermediate support assembly 112 could comprise or otherwise be defined by any suitable number of components.

The intermediate support assembly 112 and the seat section 104 are each pivotably coupled to the rear support assembly 108. More specifically, the seat section 104 is arranged so as to pivot about a rear seat axis RSA which extends through the rear uprights 114 (compare FIGS. 5-6A; pivoting about rear seat axis RSA not shown in detail), and the intermediate arms 118 of the intermediate support assembly 112 are arranged so as to pivot about a rear arm axis RAA which is spaced from the rear seat axis RSA and also extends through the rear uprights 114 (compare FIGS. 5-6A; pivoting about rear arm axis RAA not shown in detail). Furthermore, the intermediate support assembly 112 and the seat section 104 are also each pivotably coupled to the front support assembly 110. Here, the seat section 104 pivots about a front seat axis FSA which extends through the front struts 116 (compare FIGS. 5-6A; pivoting about front seat axis FSA not shown in detail), and the intermediate arms 118 pivot about a front arm axis FAA which is spaced from the front seat axis FSA and extends through the front struts 116 (compare FIGS. 5-6A; pivoting about front arm axis FAA not shown in detail). The intermediate support assembly 112 is disposed generally vertically below the seat section 104 such that the rear support assembly 108, the front support assembly 110, the intermediate support assembly 112, and the seat section 104 generally define a four-bar linkage which helps facilitate movement between the stowed configuration WC (see FIG. 5) and the chair configuration CC (see FIG. 6A). While the seat section 104 is generally configured to remain stationary relative to the support structure 102 when operating in the chair configuration CC or in the stair configuration CC according to the illustrated embodiments, it is contemplated that the seat section 104 could comprise multiple components which cooperate to facilitate "sliding" movement relative to the seat section 104 under certain operating conditions, such as to position the patient's center of gravity advantageously for transport. Other configurations are contemplated.

Figure 2:
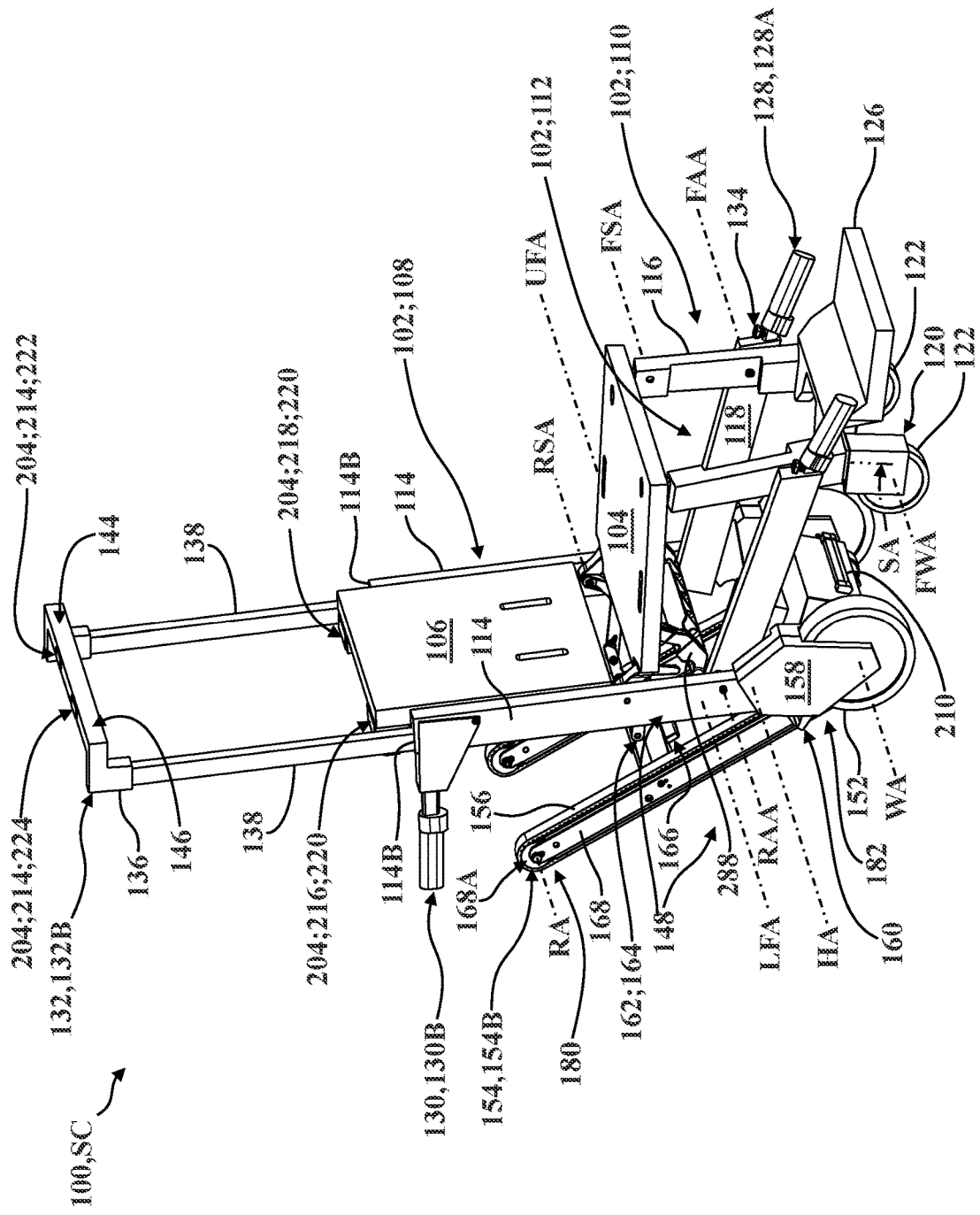
FIG. 2 is another front perspective view of the patient transport apparatus of FIG. 1, shown arranged in a stair configuration for supporting the patient for transport along stairs, and shown with the track assembly disposed in a deployed position, and with the handle assembly disposed in an extended position.
Figure 3:
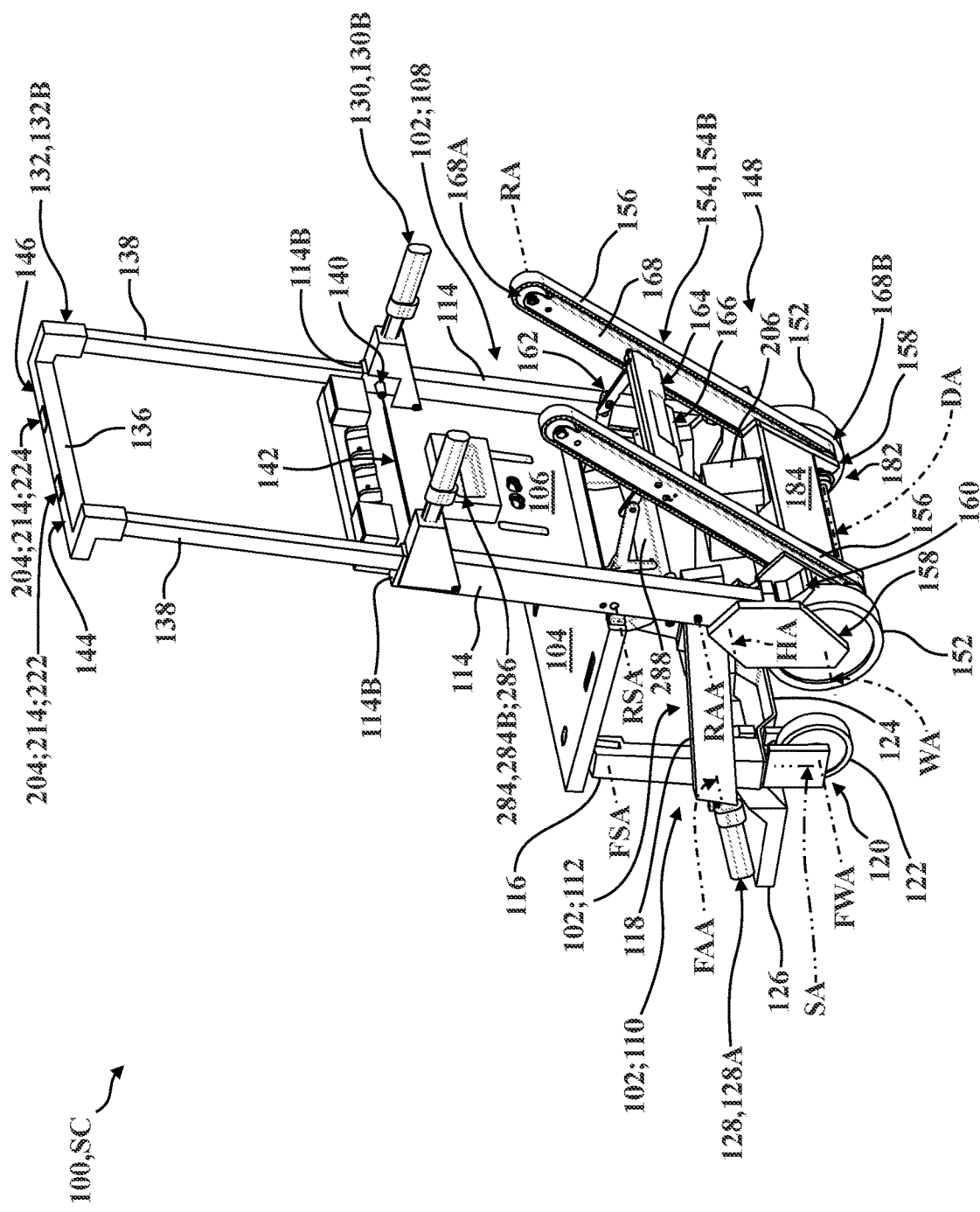
FIG. 3 is a rear perspective view of the patient transport apparatus of FIGS. 1-2, shown arranged in the stair configuration as depicted in FIG. 2, and shown having an extension lock mechanism, a folding lock mechanism, and a deployment lock mechanism.
Figure 5:
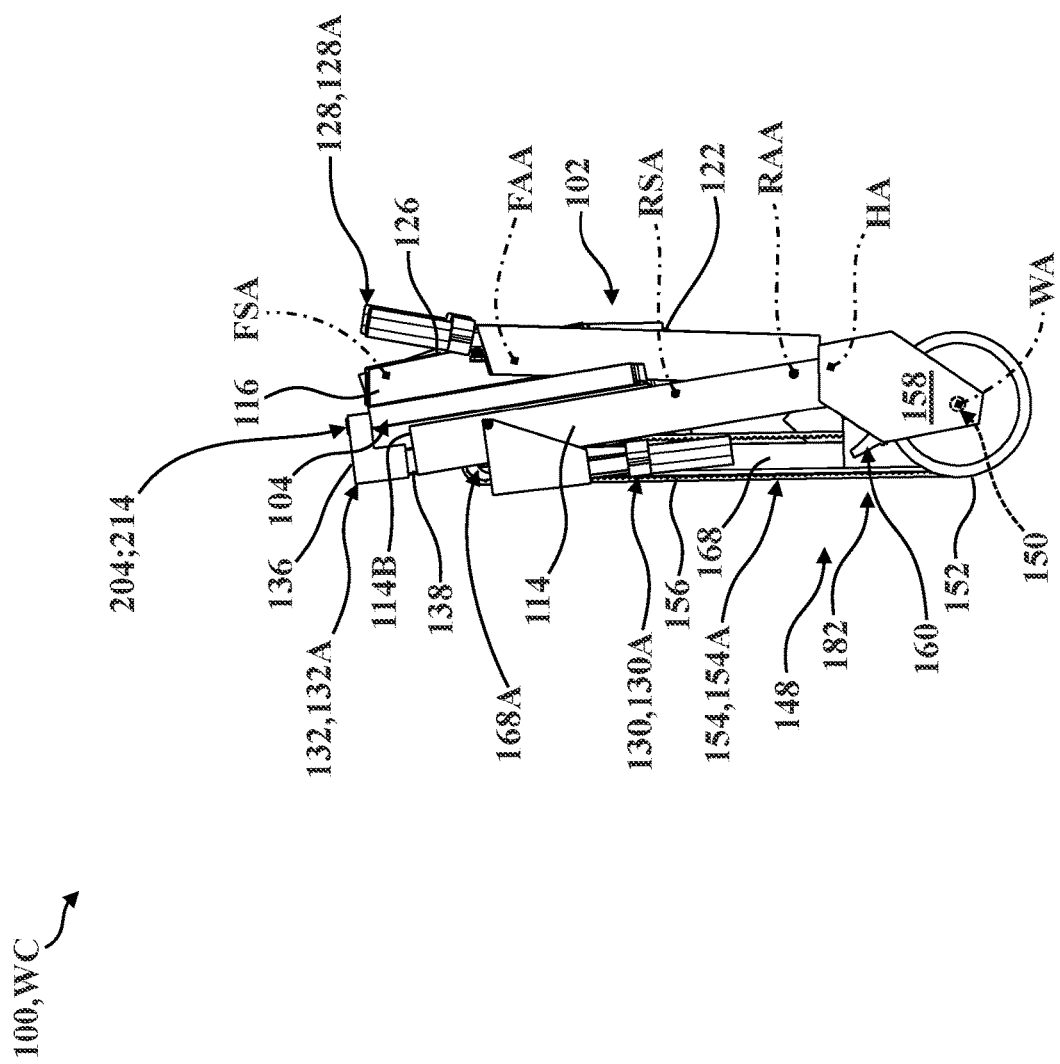
FIG. 5 is a right-side plan view of the patient transport apparatus of FIGS. 1-4, shown arranged in a stowed configuration maintained by the folding lock mechanism.
Figure 6A:
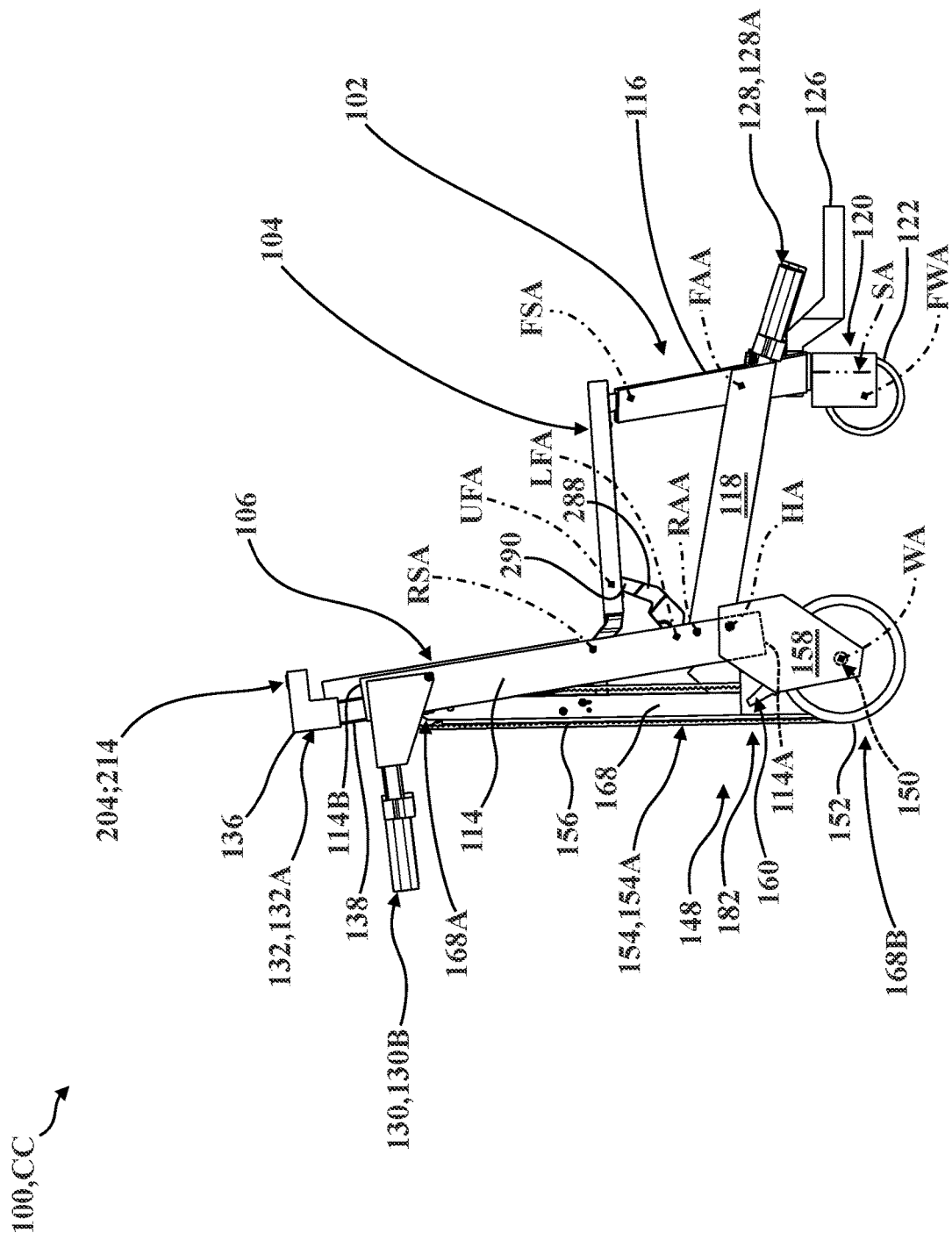
FIG. 6A is another right-side plan view of the patient transport apparatus of FIG. 5, shown arranged in the chair configuration as depicted in FIG. 1.

Referring now to FIGS. 1-3, the front support assembly 110 includes a pair of caster assemblies 120 which each comprise a front wheel 122 arranged to rotate about a respective front wheel axis FWA and to pivot about a respective swivel axis SA (compare FIGS. 5-6A; pivoting about swivel axis SA not shown in detail). The caster assemblies 120 are generally arranged on opposing lateral sides of the front support assembly 110 and are operatively attached to the front struts 116. A lateral brace 124 (see FIG. 3) extends laterally between the front struts 116 to, among other things, afford rigidity to the support structure 102. Here, a foot rest 126 is pivotably coupled to each of the front struts 116 adjacent to the caster assemblies 120 (pivoting not shown in detail) to provide support to the patient's feet during transport. For each of the pivotable connections disclosed herein, it will be appreciated that one or more fasteners, bushings, bearings, washers, spacers, and the like may be provided to facilitate smooth pivoting motion between various components.

The representative embodiments of the patient transport apparatus 100 illustrated throughout the drawings comprise different handles arranged for engagement by caregivers during patient transport. More specifically, the patient transport apparatus 100 comprises front handle assemblies 128, pivoting handle assemblies 130, and an upper handle assembly 132 (hereinafter referred to as "handle assembly 132), each of which will be described in greater detail below. The front handle assemblies 128 are supported within the respective intermediate arms 118 for movement between a collapsed position 128A (see FIG. 12A) and an extended position 128B (see FIG. 12B). To this end, the front handle assemblies 128 may be slidably supported by bushings, bearings, and the like (not shown) coupled to the intermediate arms 118, and may be lockable in and/or between the collapsed position 128A and the extended position 128B via respective front handle locks 134 (see FIG. 1). Here, a caregiver may engage the front handle locks 134 (not shown in detail) to facilitate moving the front handle assemblies 128 between the collapsed position 128A and the extended position 128B. The front handle assemblies 128 are generally arranged so as to be engaged by a caregiver during patient transport up or down stairs ST when in the extended position 128B. It will be appreciated that the front handle assemblies 128 could be of various types, styles, and/or configurations suitable to be engaged by caregivers to support the patient transport apparatus 100 for movement. While the illustrated front handle assemblies 128 are arranged for telescoping movement, other configurations are contemplated. By way of non-limiting example, the front handle assemblies 128 could be pivotably coupled to the support structure 102 or other parts of the patient transport apparatus 100. In some embodiments, the front handle assemblies 128 could be configured similar to as is disclosed in U.S. Pat. No. 6,648,343, the disclosure of which is hereby incorporated by reference in its entirety.

The pivoting handle assemblies 130 are coupled to the respective rear uprights 114 of the rear support assembly 108, and are movable relative to the rear uprights 114 between a stowed position 130A (see FIG. 5) and an engagement position 130B (see FIG. 6A). Like the front handle assemblies 128, the pivoting handle assemblies 130 are generally arranged for engagement by a caregiver during patient transport, and may advantageously be utilized in the engagement position 130B when the patient transport apparatus 100 operates in the chair configuration CC to transport the patient along floor surfaces FS. In some embodiments, the pivoting handle assemblies 130 could be configured similar to as is disclosed in U.S. Pat. No. 6,648,343, previously referenced. Other configurations are contemplated.

Figure 12A:
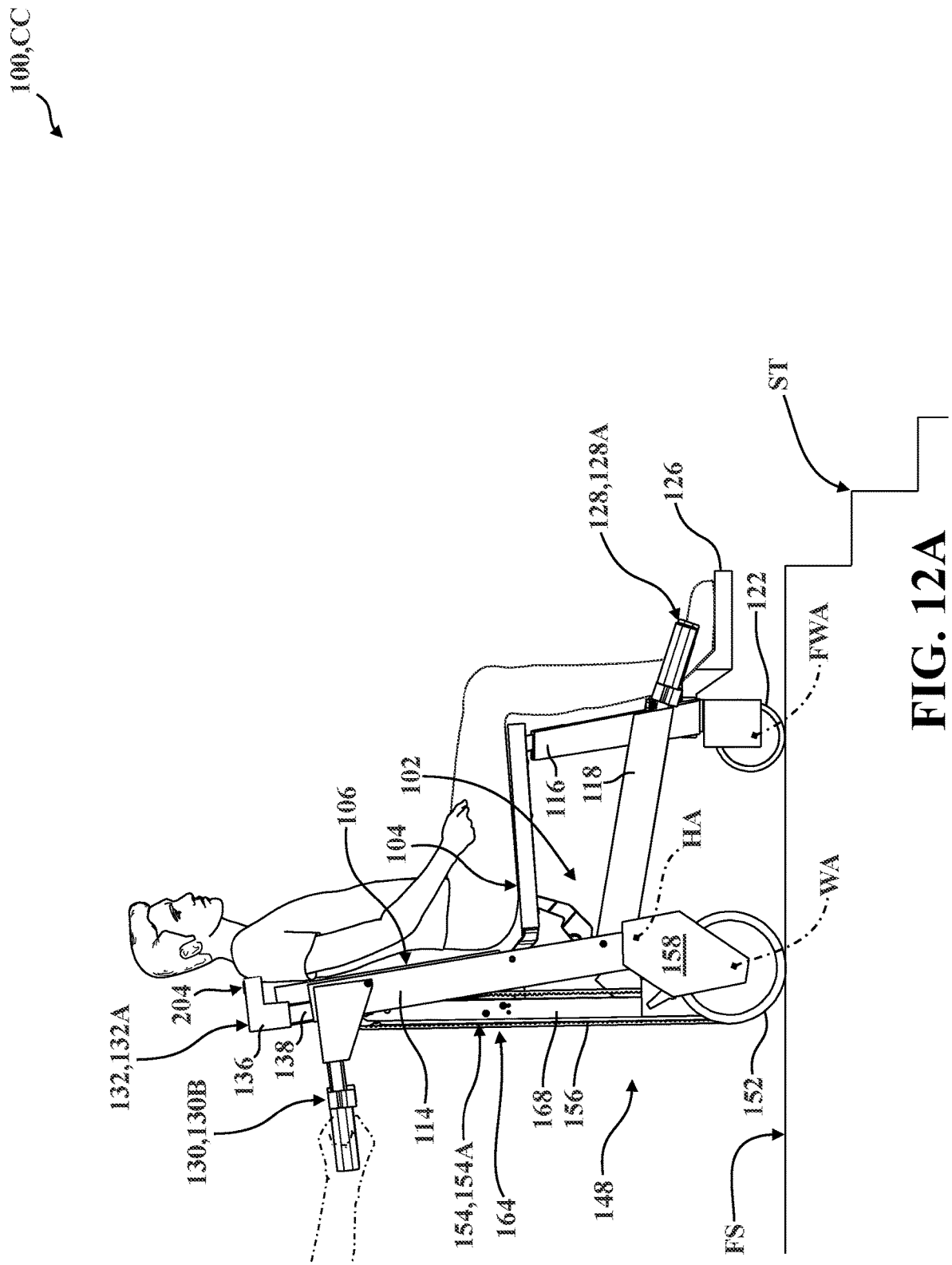
FIG. 12A is a right-side plan view of the patient transport apparatus of FIGS. 1-11D, shown supporting a patient in the chair configuration on a floor surface adjacent to stairs, and shown with a first caregiver engaging a pivoting handle assembly.
Figure 12B:
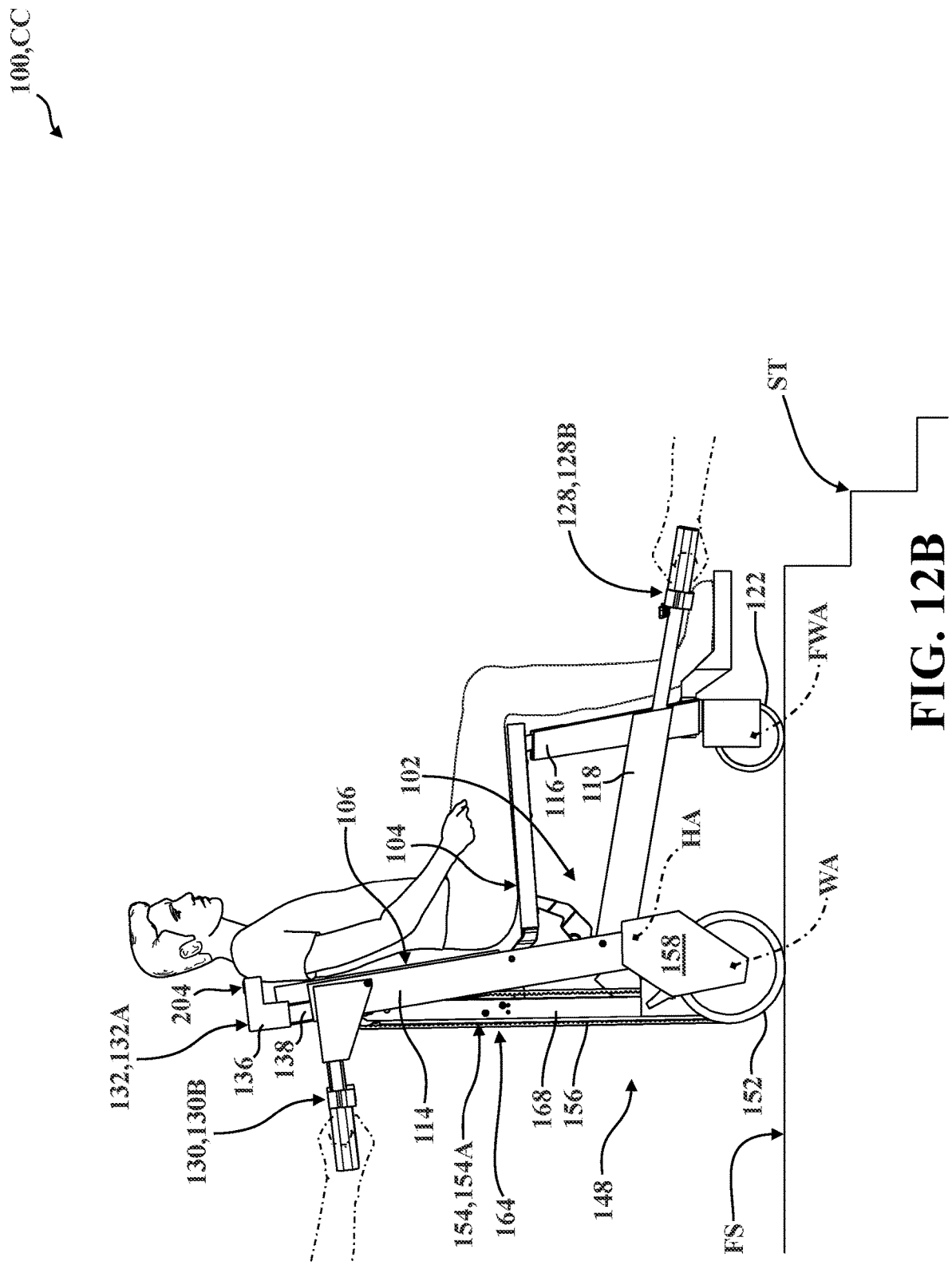
FIG. 12B is another right-side plan view of the patient transport apparatus of FIG. 12A, shown with a second caregiver engaging a front handle assembly in an extended position.
Figure 12C:
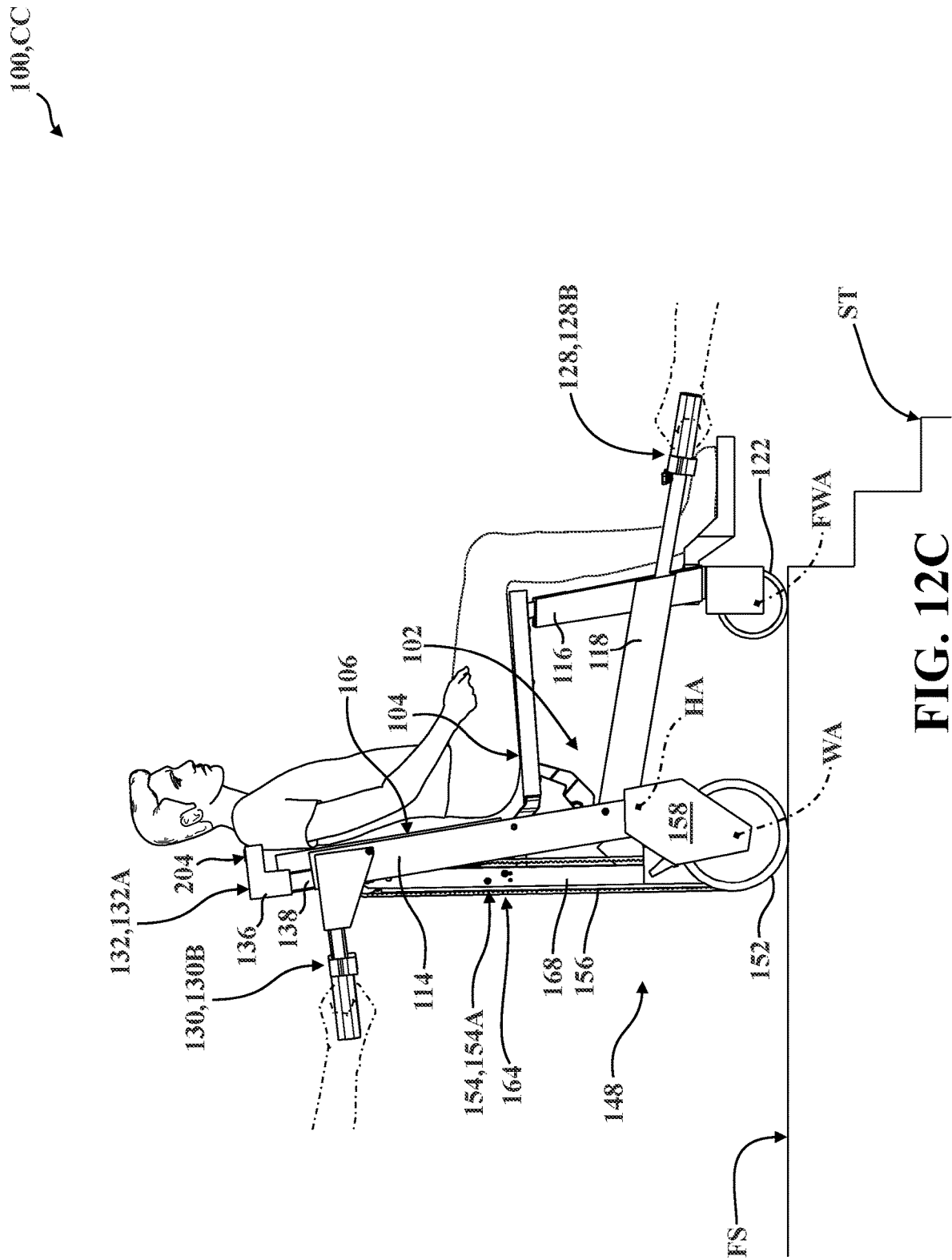
FIG. 12C is another right-side plan view of the patient transport apparatus of FIG. 12B, shown having moved closer to the stairs.
Figure 12D:
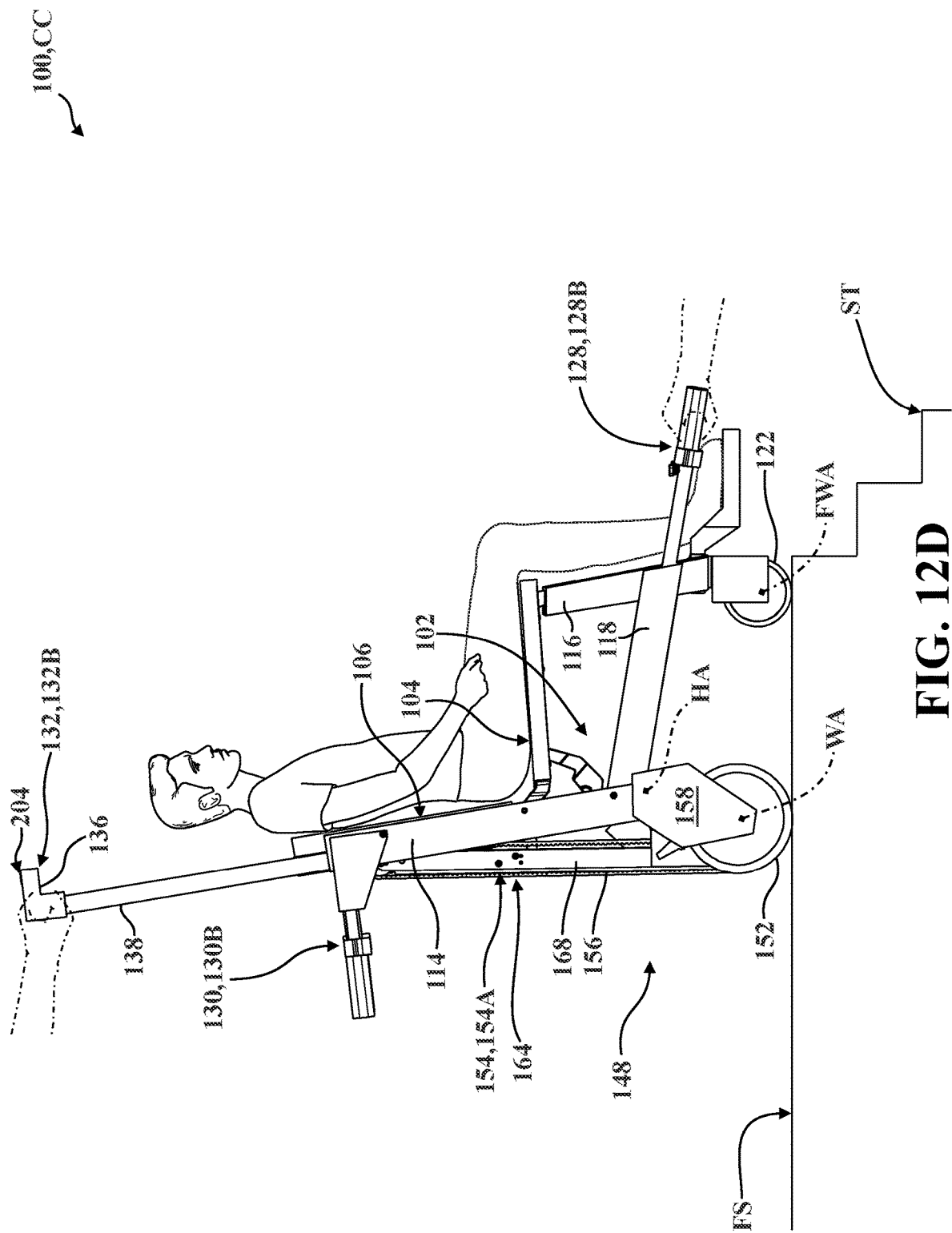
FIG. 12D is another right-side plan view of the patient transport apparatus of FIG. 12C, shown with the first caregiver engaging the handle assembly in the extended position.

The handle assembly 132 is also coupled to the rear support assembly 108, and generally comprises an upper grip 136 operatively attached to extension posts 138 which are supported within the respective rear uprights 114 for movement between a collapsed position 132A (see FIGS. 1 and 12C) and an extended position 132B (see FIGS. 2 and 12D). To this end, the extension posts 138 of the handle assembly 132 may be slidably supported by bushings, bearings, and the like (not shown) coupled to the rear uprights 114, and may be lockable in and/or between the collapsed position 132A and the extended position 132B via an extension lock mechanism 140 with an extension lock release 142 arranged for engagement by the caregiver. As is best shown in FIG. 3, the extension lock release 142 may be realized as a flexible connector which extends generally laterally between the rear uprights 114, and supports a cable connected to extension lock mechanisms 140 which releasably engage the extension posts 138 to maintain the handle assembly 132 in the extended position 132B and the collapsed position 132A (not shown in detail). Here, it will be appreciated that the extension lock mechanism 140 and/or the extension lock release 142 could be of a number of different styles, types, configurations, and the like sufficient to facilitate selectively locking the handle assembly 132 in the extended position 132B. In some embodiments, the handle assembly 132, the extension lock mechanism 140, and/or the extension lock release 142 could be configured similar to as is disclosed in U.S. Pat. No. 6,648,343, previously referenced. Other configurations are contemplated.

Figure 12E:
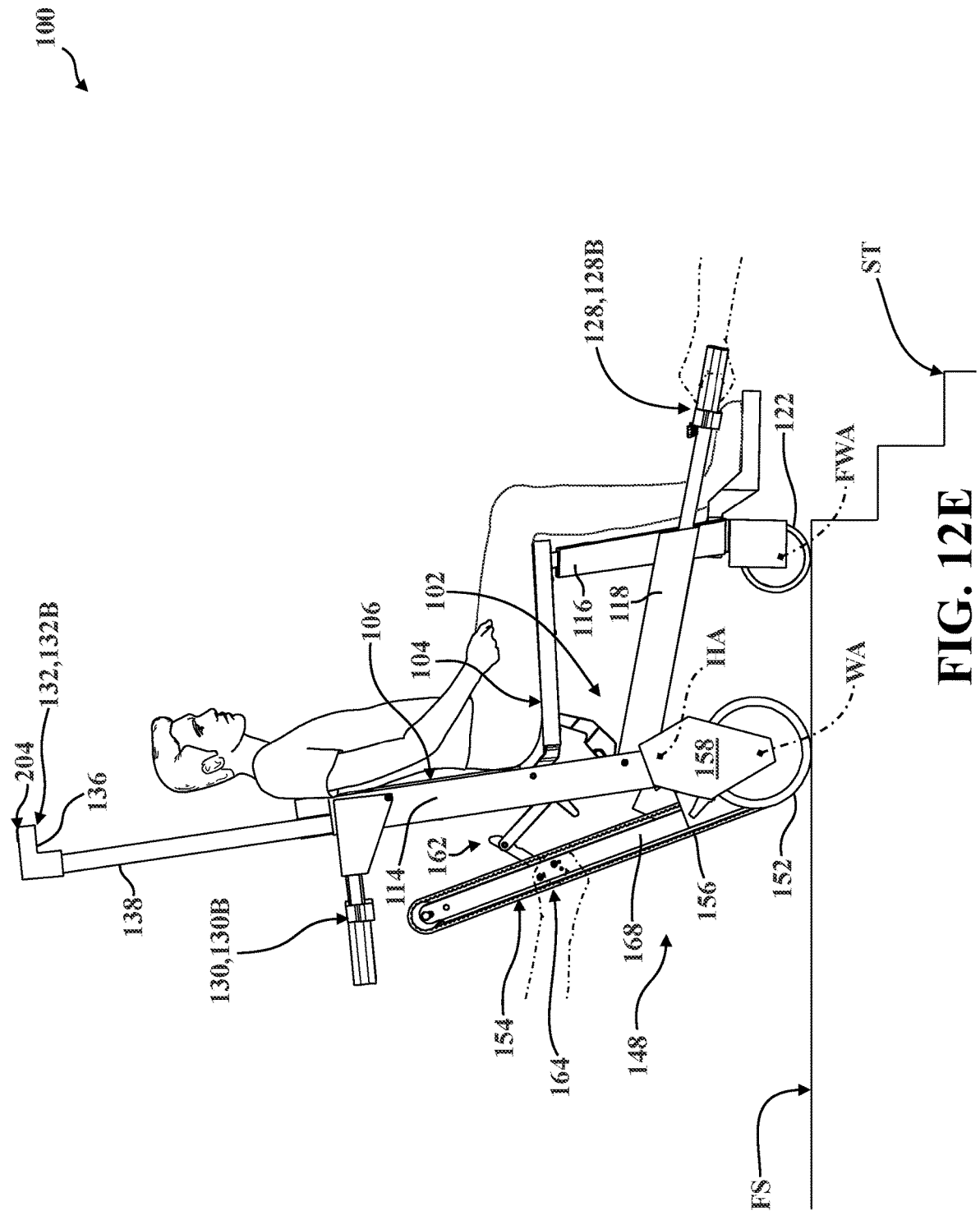
FIG. 12E is another right-side plan view of the patient transport apparatus of FIG. 12D, shown with the first caregiver having engaged the deployment lock mechanism to move the track assembly out of the retracted position.
Figure 12F:
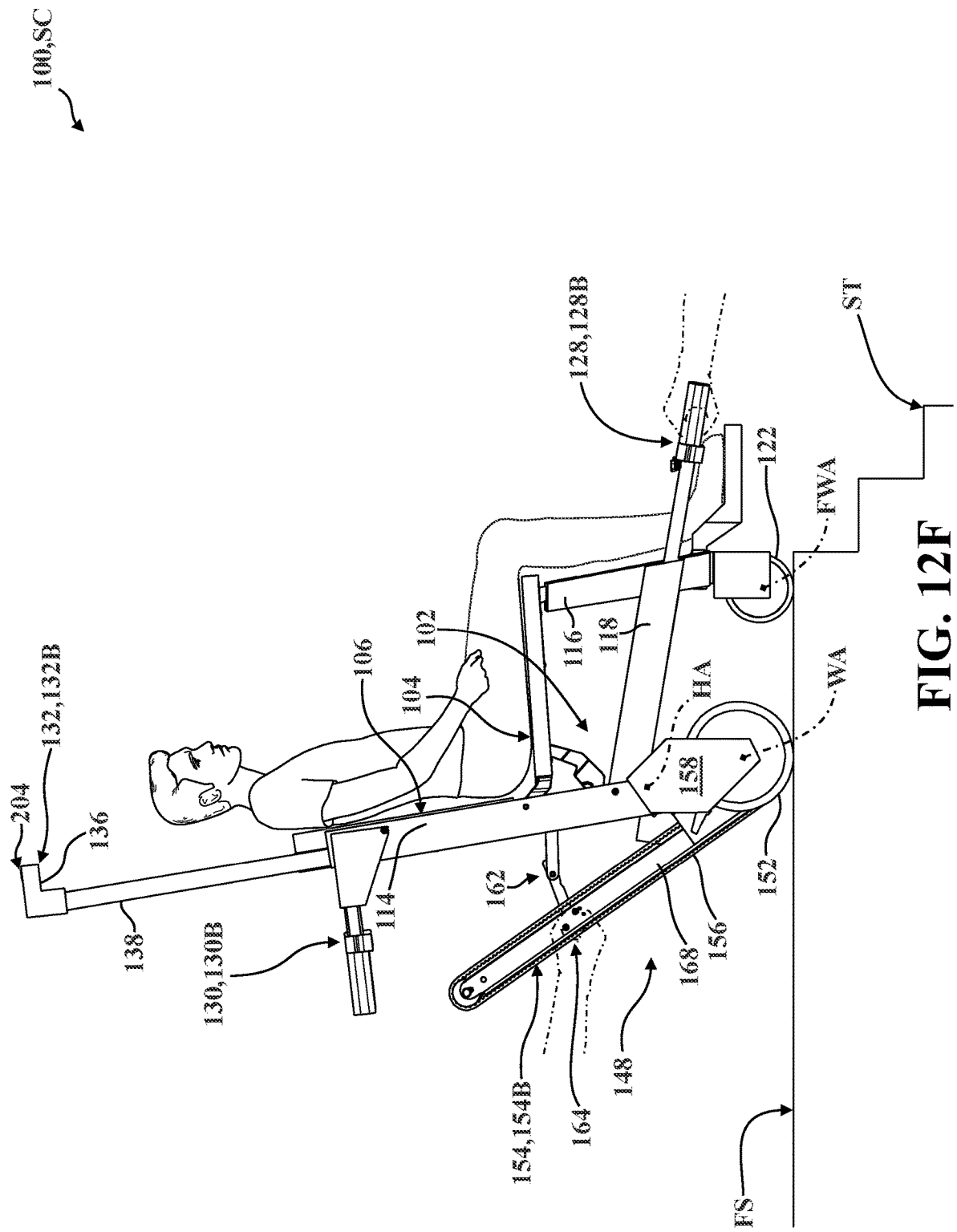
FIG. 12F is another right-side plan view of the patient transport apparatus of FIG. 12E, shown supporting the patient in the stair configuration with the track assembly in the deployed position.
Figure 12G:
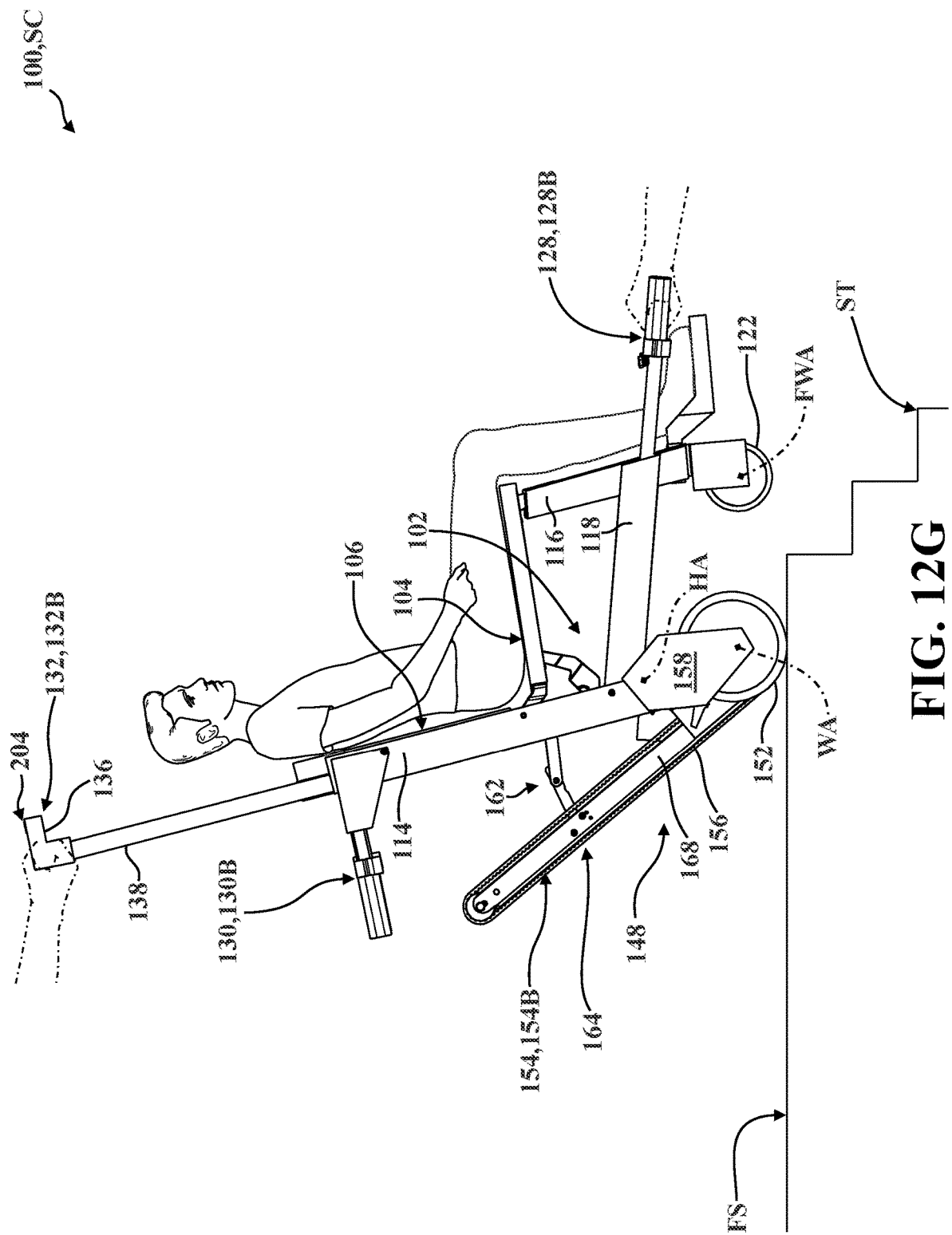
FIG. 12G is another right-side plan view of the patient transport apparatus of FIG. 12F, shown having moved towards the stairs for descent while supported by the first and second caregivers.
Figure 12H:
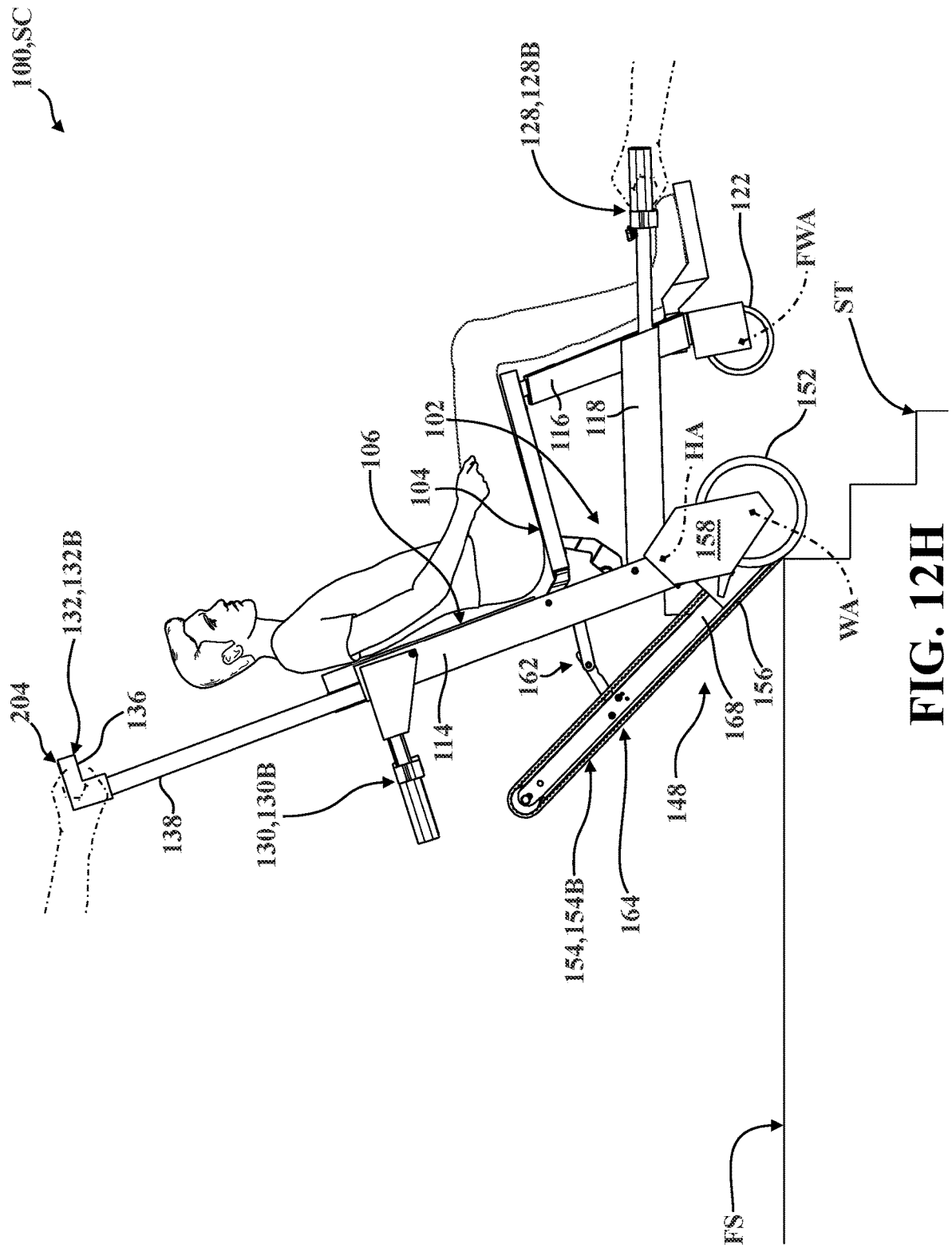
FIG. 12H is another right-side plan view of the patient transport apparatus of FIG. 12C, shown having moved initially down the stairs for descent to bring a belt of the track assembly into contact with the stairs while still supported by the first and second caregivers.
Figure 12I:
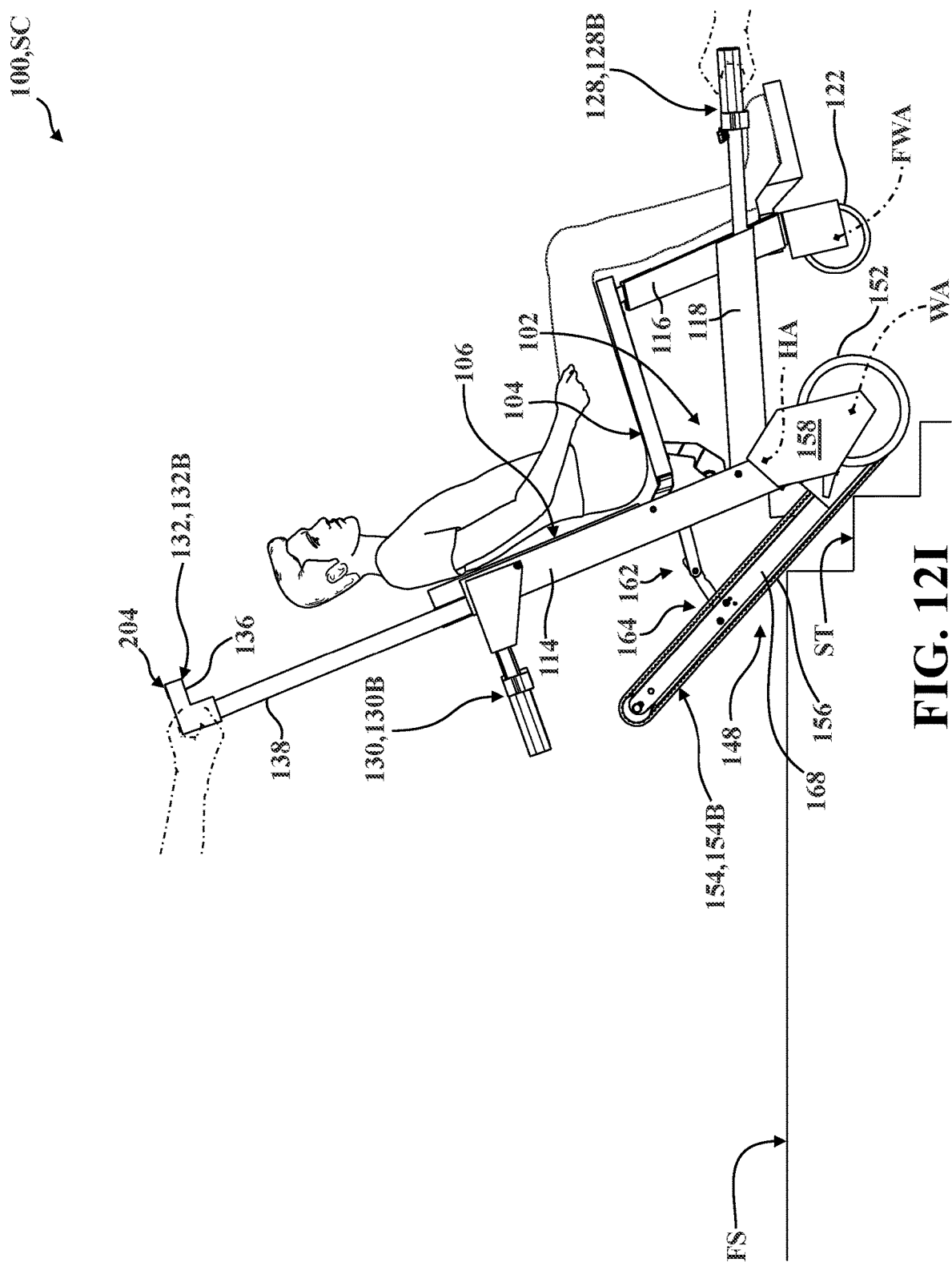
FIG. 12I is another right-side plan view of the patient transport apparatus of FIG. 12C, shown with the belt of the track assembly in contact with the stairs while still supported by the first and second caregivers.

In the representative embodiment illustrated herein, the upper grip 136 generally comprises a first hand grip region 144 arranged adjacent to one of the extension posts 138, and a second hand grip region 146 arranged adjacent to the other of the extension posts 138, each of which may be engaged by the caregiver to support the patient transport apparatus 100 for movement, such as during patient transport up or down stairs ST (see FIGS. 12G-12I).

As noted above, the patient transport apparatus 100 is configured for use int transporting the patient across floor surfaces FS, such as when operating in the stair configuration SC, and for transporting the patient along stairs ST when operating in the stair configuration SC. To these ends, the illustrated patient transport apparatus 100 includes a carrier assembly 148 arranged for movement relative to the support structure 102 between the chair configuration CC and the stair configuration ST. The carrier assembly 148 generally comprises at least one shaft 150 defining a wheel axis WA, one or more rear wheels 152 supported for rotation about the wheel axis WA, at least one track assembly 154 having a belt 156 for engaging stairs ST, and one or more hubs 158 supporting the shaft 150 and the track assembly 154 and the shaft 150 for concurrent pivoting movement about a hub axis HA. Here, movement of the carrier assembly 148 from the chair configuration CC (see FIGS. 1 and 6A) to the stair configuration SC (see FIGS. 2 and 6B) simultaneously deploys the track assembly 154 for engaging stairs ST with the belt 156 and moves the wheel axis WA longitudinally closer to the front support assembly 110 so as to position the rear wheels 152 further underneath the seat section 104 and closer to the front wheels 122.

As is described in greater detail below in connection with FIGS. 12A-12I, the movement of the rear wheels 152 relative to the front wheels 122 when transitioning from the chair configuration CC to the stair configuration SC that is afforded by the patient transport apparatus 100 of the present disclosure affords significant improvements in patient comfort and caregiver usability, in that the rear wheels 152 are arranged to promote stable transport across floor surfaces FS in the chair configuration CC but are arranged to promote easy transitioning from floor surfaces to stairs ST as the patient transport apparatus 100 is "tilted" backwards about the rear wheels 152 (compare FIGS. 12D-12H). Put differently, positioning the rear wheels 152 relative to the front wheels 122 consistent with the present disclosure makes "tilting" the patient transport apparatus 100 significantly less burdensome for the caregivers and, at the same time, much more comfortable for the patient due to the arrangement of the patient's center of gravity relative to the portion of the rear wheels 152 contacting the floor surface FS as the patient transport apparatus 100 is "tilted" backwards to transition into engagement with the stairs ST.

In the representative embodiments illustrated herein, the carrier assembly 148 comprises hubs 158 that are pivotably coupled to the respective rear uprights 114 for concurrent movement about the hub axis HA. Here, one or more bearings, bushings, shafts, fasteners, and the like (not shown in detail) may be provided to facilitate pivoting motion of the hubs 158 relative to the rear uprights 114. Similarly, bearings and/or bushings (not shown) may be provided to facilitate smooth rotation of the rear wheels 152 about the wheel axis WA. Here, the shafts 150 may be fixed to the hubs 158 such that the rear wheels 152 rotate about the shafts 150 (e.g., about bearings supported in the rear wheels 152), or the shafts 150 could be supported for rotation relative to the hubs 158. Each of the rear wheels 152 is also provided with a wheel lock 160 coupled to its respective hub 158 to facilitate inhibiting rotation about the wheel axis WA. The wheel locks 160 are generally pivotable relative to the hubs 158, and may be configured in a number of different ways without departing from the scope of the present disclosure. While the representative embodiment of the patient transport apparatus 100 illustrated herein employs hubs 158 with "mirrored" profiles that are coupled to the respective rear uprights 114 and support discrete shafts 150 and wheel locks 160, it will be appreciated that a single hub 158 and/or a single shaft 150 could be employed. Other configurations are contemplated.

Figure 6B:
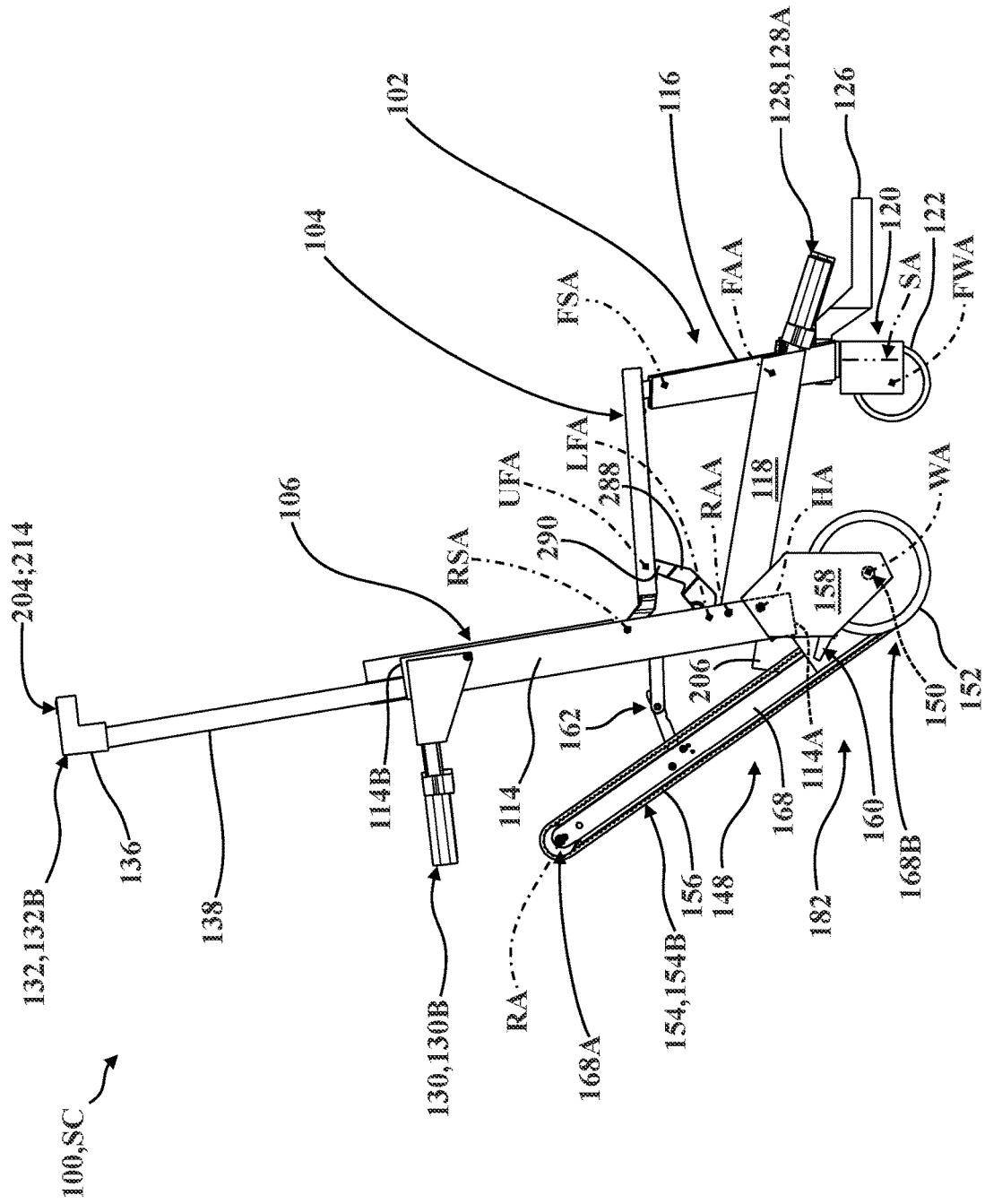
FIG. 6B is another right-side plan view of the patient transport apparatus of FIGS. 5-6A, shown arranged in the stair configuration as depicted in FIGS. 2-3.

As is best depicted in FIGS. 6A-6B, the rear uprights 114 each generally extend between a lower upright end 114A and an upper upright end 114B, with the hub axis HA arranged adjacent to the lower upright end 114A. The lower upright end 114A is supported for movement within the hub 158, which may comprise a hollow profile or recess defined by multiple hub housing components (not shown in detail in FIGS. 6A-6B). The rear uprights 114 may each comprise a generally hollow, extruded profile which supports various components of the patient transport apparatus 100. In the illustrated embodiment, the hub axis HA is arranged generally vertically between the rear arm axis RAA and the wheel axis WA.

Figure 7A:
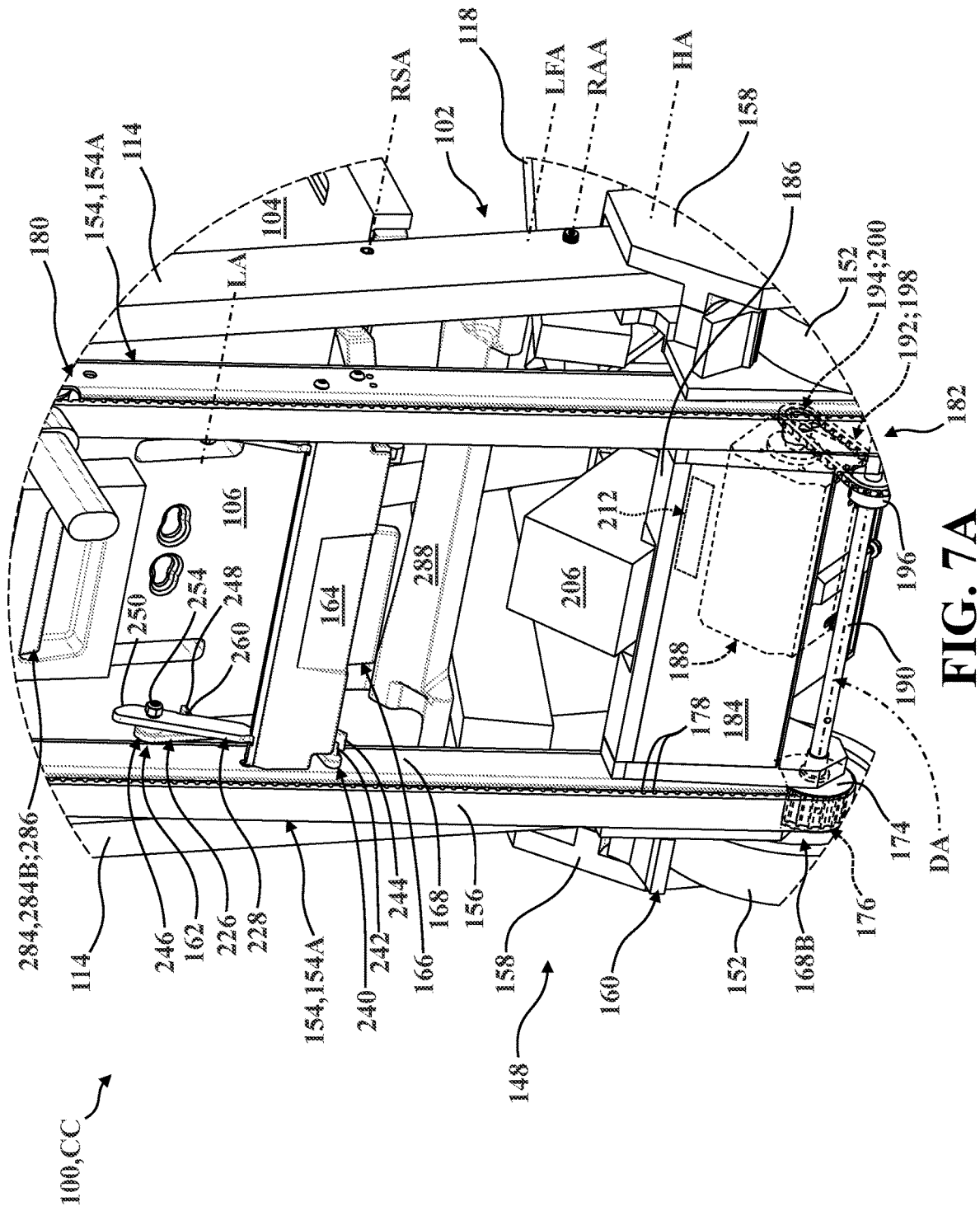
FIG. 7A is a partial rear perspective view of the patient transport apparatus of FIGS. 1-6B, shown arranged in the chair configuration as depicted in FIGS. 1 and 6A, with the deployment lock mechanism shown retaining the track assembly in the retracted position.
Figure 7B:
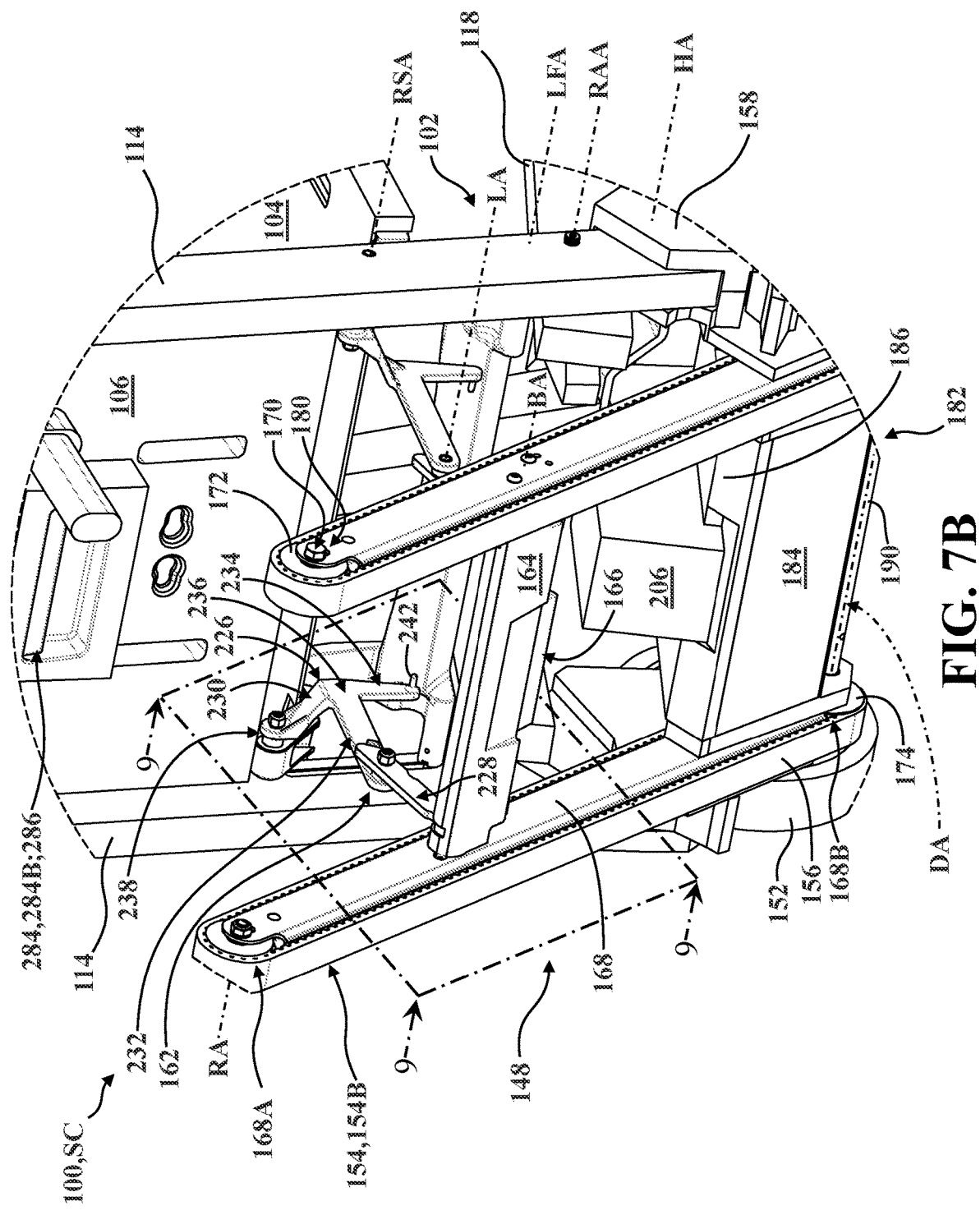
FIG. 7B is another partial rear perspective view of the patient transport apparatus of FIG. 7A, shown arranged in the stair configuration as depicted in FIGS. 2-3 and 6B, with the deployment lock mechanism shown retaining the track assembly in the deployed position.

Referring now to FIGS. 7A-7B, as noted above, the track assemblies 154 move concurrently with the hubs 158 between the chair configuration CC and the stair configuration SC. Here, the track assemblies 154 are arranged in a retracted position 154A when the carrier assembly 148 is disposed in the chair configuration CC, and are disposed in a deployed position 154B when the carrier assembly 148 is disposed in the stair configuration SC. As is described in greater detail below, the illustrated patient transport apparatus 100 comprises a deployment linkage 162 and a deployment lock mechanism 164 with a deployment lock release 166 arranged for engagement by the caregiver to facilitate changing between the retracted position 154A and the deployed position 154B (and, thus, between the chair configuration CC and the stair configuration SC).

In the illustrated embodiment, the patient transport apparatus 100 comprises laterally-spaced track assemblies 154 each having a single belt 156 arranged to contact stairs ST. However, it will be appreciated that other configurations are contemplated, and a single track assembly 154 and/or track assemblies with multiple belts 156 could be employed. The track assemblies 154 each generally comprise a rail 168 extending between a first rail end 168A and a second rail end 168B. The second rail end 168B is operatively attached to the hub 158, such as with one or more fasteners (not shown in detail). An axle 170 defining a roller axis RA is disposed adjacent to the first rail end 168A of each rail 168, and a roller 172 is supported for rotation about the roller axis RA (compare FIGS. 9A-9B). For each of the track assemblies 154, the belt 156 is disposed in engagement with the roller 172 and is arranged for movement relative to the rail 168 in response to rotation of the roller 172 about the roller axis RA. Adjacent to the second rail end 168B of each rail 168, a drive pulley 174 is supported for rotation about a drive axis DA and is likewise disposed in engagement with the belt 156 (see FIGS. 7A-7B; rotation about drive axis DA not shown in detail). Here, the drive pulley 174 comprises outer teeth 176 which are disposed in engagement with inner teeth 178 formed on the belt 156. The track assemblies 154 each also comprise a belt tensioner, generally indicated at 180, configured to adjust tension in the belt 156 between the roller 172 and the drive pulley 174.

In the representative embodiment illustrated herein, the patient transport apparatus 100 comprises a drive system, generally indicated at 182, configured to facilitate driving the belts 156 of the track assemblies 154 relative to the rails 168 to facilitate movement of the patient transport apparatus 100 up and down stairs ST. To this end, and as is depicted in FIG. 7A, the drive system 182 comprises a drive frame 184 and a cover 186 which are operatively attached to the hubs 158 of the carrier assembly 148 for concurrent movement with the track assemblies 154 between the retracted position 154A and the deployed position 154B. A motor 188 (depicted in phantom in FIG. 7A) is coupled to the drive frame 184 and is concealed by the cover 186. The motor 188 is configured to selectively generate rotational torque used to drive the belts 156 via the drive pulleys 174, as described in greater detail below. To this end, a drive axle 190 is coupled to each of the drive pulleys 174 and extends along the drive axis DA laterally between the track assemblies 154. The drive axle 190 is rotatably supported by the drive frame 184, such as by one or more bearings, bushings, and the like (not shown in detail). A geartrain 192 is disposed in rotational communication between the motor 188 and the drive axle 190. To this end, in the embodiment depicted in FIG. 7A, the geartrain 192 comprises a first sprocket 194, a second sprocket 196, and an endless chain 198. Here, the motor 188 comprises an output shaft 200 to which the first sprocket 194 is coupled, and the second sprocket 196 is coupled to the drive axle 190. The endless chain 198, in turn, is supported about the first sprocket 194 and the second sprocket 196 such that the drive axle 190 and the output shaft 200 rotate concurrently. The geartrain 192 may be configured so as to adjust the rotational speed and/or torque of the drive axle 190 relative to the output shaft 200 of the motor, such as by employing differently-configured first and second sprockets 194, 196 (e.g., different diameters, different numbers of teeth, and the like).

While the representative embodiment of the drive system 182 illustrated herein utilizes a single motor 188 to drive the belts 156 of the track assemblies 154 concurrently using a chain-based geartrain 192, it will be appreciated that other configurations are contemplated. By way of non-limiting example, multiple motors 188 could be employed, such as to facilitate driving the belts 156 of the track assemblies 154 independently. Furthermore, different types of geartrains 192 are contemplated by the present disclosure, including without limitation geartrains 192 which comprise various arrangements of gears, planetary gearsets, and the like.

Figure 4:
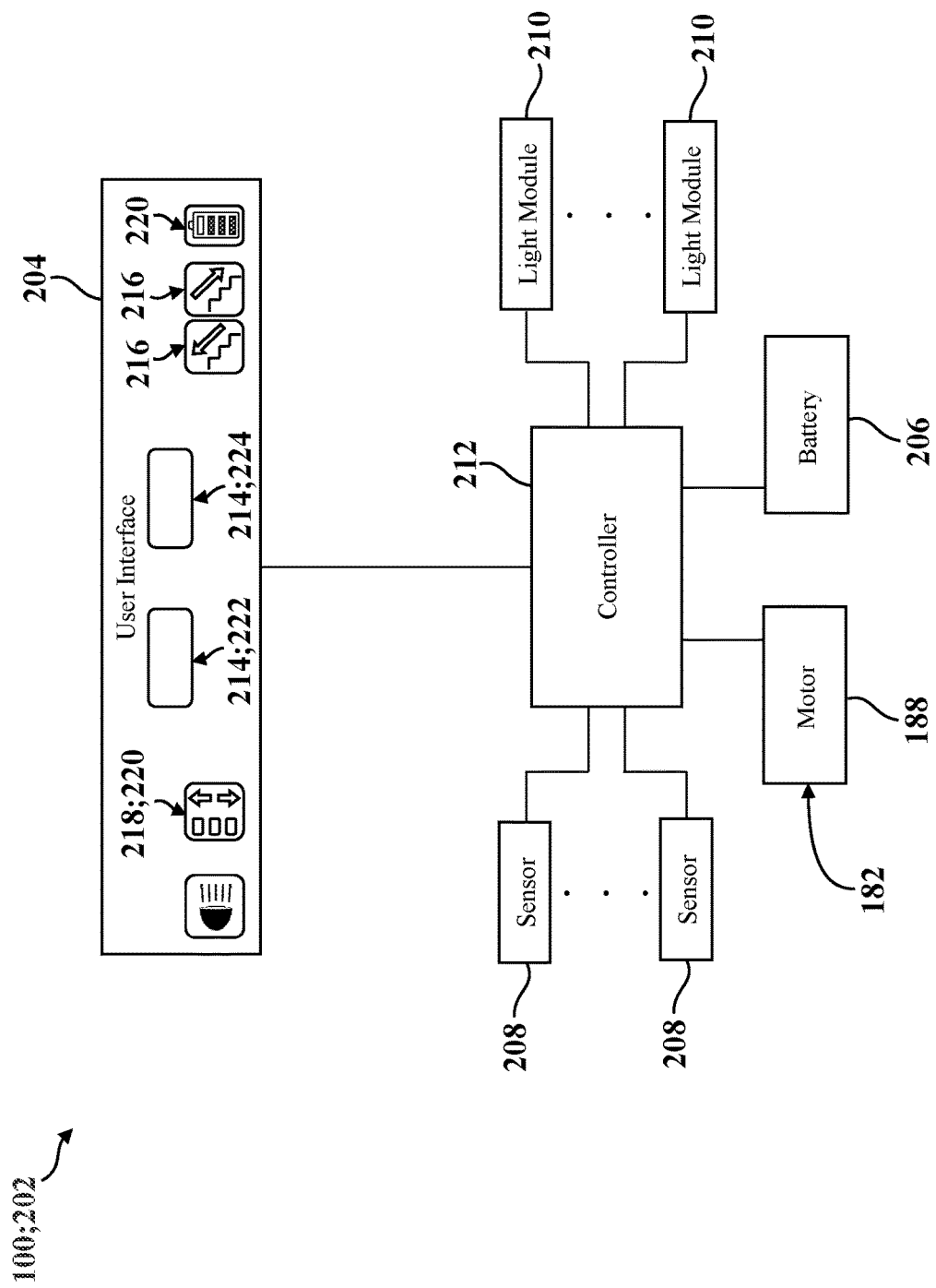
FIG. 4 is a partial schematic view of a control system of the patient transport apparatus of FIGS. 1-3, shown with a controller disposed in communication with a battery, a user interface, a drive system, and a plurality of light modules.

The patient transport apparatus 100 comprises a control system 202 to, among other things, facilitate control of the track assemblies 154. To this end, and as is depicted schematically in FIG. 4, the representative embodiment of the control system 202 generally comprises a user interface 204, a battery 206, one or more sensors 208, and one or more light modules 210 which are disposed in electrical communication with a controller 212. As will be appreciated from the subsequent description below, the controller 212 may be of a number of different types, styles, and/or configurations, and may employ one or more microprocessors for processing instructions or an algorithm stored in memory to control operation of the motor 188, the light modules 210, and the like. Additionally or alternatively, the controller 212 may comprise one or more sub-controllers, microcontrollers, field programmable gate arrays, systems on a chip, discrete circuitry, and/or other suitable hardware, software, and/or firmware that is capable of carrying out the functions described herein. The controller 212 is coupled to various electrical components of the patient transport apparatus 100 (e.g., the motor 188) in a manner that allows the controller 212 to control or otherwise interact with those electrical components the (e.g., via wired and/or wireless electrical communication). In some embodiments, the controller 212 may generate and transmit control signals to the one or more powered devices, or components thereof, to drive or otherwise facilitate operating those powered devices, or to cause the one or more powered devices to perform one or more of their respective functions.

The controller 212 may utilize various types of sensors 208 of the control system 202, including without limitation force sensors (e.g., load cells), timers, switches, optical sensors, electromagnetic sensors, motion sensors, accelerometers, potentiometers, infrared sensors, ultrasonic sensors, mechanical limit switches, membrane switches, encoders, and/or cameras. One or more sensors 208 may be used to detect mechanical, electrical, and/or electromagnetic coupling between components of the patient transport apparatus 100. Other types of sensors 208 are also contemplated. Some of the sensors 208 may monitor thresholds movement relative to discrete reference points. The sensors 208 can be located anywhere on the patient transport apparatus 100, or remote from the patient transport apparatus 100. Other configurations are contemplated.

It will be appreciated that the patient transport apparatus 100 may employ light modules 210 to, among other things, illuminate the user interface 204, direct light toward the floor surface FS, and the like. It will be appreciated that the light modules 210 can be of a number of different types, styles, configurations, and the like (e.g., light emitting diodes LEDs) without departing from the scope of the present disclosure. Similarly, it will be appreciated that the user interface 204 may employ user input controls of a number of different types, styles, configurations, and the like (e.g., capacitive touch sensors, switches, buttons, and the like) without departing from the scope of the present disclosure.

The battery 206 provides power to the controller 212, the motor 188, the light modules 210, and other components of the patient transport apparatus 100 during use, and is removably attachable to the cover 186 of the drive system 182 in the illustrated embodiment (see FIG. 7A; attachment not shown in detail). The user interface 204 is generally configured to facilitate controlling the drive direction and drive speed of the motor 188 to move the belts 156 of the track assembly 154 and, thus, allow the patient transport apparatus 100 to ascend or descend stairs ST. Here, the user interface 204 may comprise one or more activation input controls 214 to facilitate driving the motor 188 in response to engagement by the caregiver, one or more direction input controls 216 to facilitate changing the drive direction of the motor 188 in response to engagement by the caregiver, and/or one or more speed input controls 218 to facilitate operating the motor 188 at different predetermined speeds selectable by the caregiver. The user interface 204 may also comprise various types of indicators 220 to display information to the caregiver. It will be appreciated that the various components of the control system 202 introduced above could be configured and/or arranged in a number of different ways, and could communicate with each other via one or more types of electrical communication facilitated by wired and/or wireless connections. Other configurations are contemplated.

The activation input controls 214 may be arranged in various locations about the patient transport apparatus. In the illustrated embodiments, a first activation input control 222 is disposed adjacent to the first hand grip region 144 of the handle assembly 132, and a second activation input control 224 is disposed adjacent to the second hand grip region 146. In the illustrated embodiment, the user interface 204 is configured such that the caregiver can engage either of the activation input controls 222, 224 with a single hand grasping the upper grip 136 of the handle assembly 132 during use.

In the illustrated embodiments, the patient transport apparatus 100 is configured to limit movement of the belts 156 relative to the rails 168 during transport along stairs ST in an absence of engagement with the activation input controls 214 by the caregiver. Put differently, one or more of the controller 212, the motor 188, the geartrain 192, and/or the track assemblies 154 may be configured to "brake" or otherwise prevent movement of the belts 156 unless the activation input controls 214 are engaged. To this end, the motor 188 may be controlled via the controller 212 to prevent rotation (e.g., driving with a 0% pulse-width modulation PWM signal) in some embodiments. However, other configurations are contemplated, and the patient transport apparatus 100 could be configured to prevent movement of the belts 156 in other ways. By way of non-limiting example, a mechanical brake system (not shown) could be employed in some embodiments.

Referring now to FIGS. 7A-9B, the patient transport apparatus 100 employs the deployment lock mechanism 164 to releasably secure the track assembly 154 in the retracted position 154A and in the deployed position 154B. As is described in greater detail below, the deployment lock release 166 is arranged for engagement by the caregiver to move between the retracted position 154A and the deployed position 154B. The deployment lock mechanism 164 is coupled to the track assemblies 154 for concurrent movement, and the deployment linkage 162 is coupled between the deployment lock mechanism 164 and the support structure 102. The illustrated deployment linkage 162 generally comprises connecting links 226 which are pivotably coupled to the support structure 102, and brace links 228 which are coupled to the deployment lock mechanism 164 and are respectively pivotably coupled to the connecting links 226.

Figure 9A:
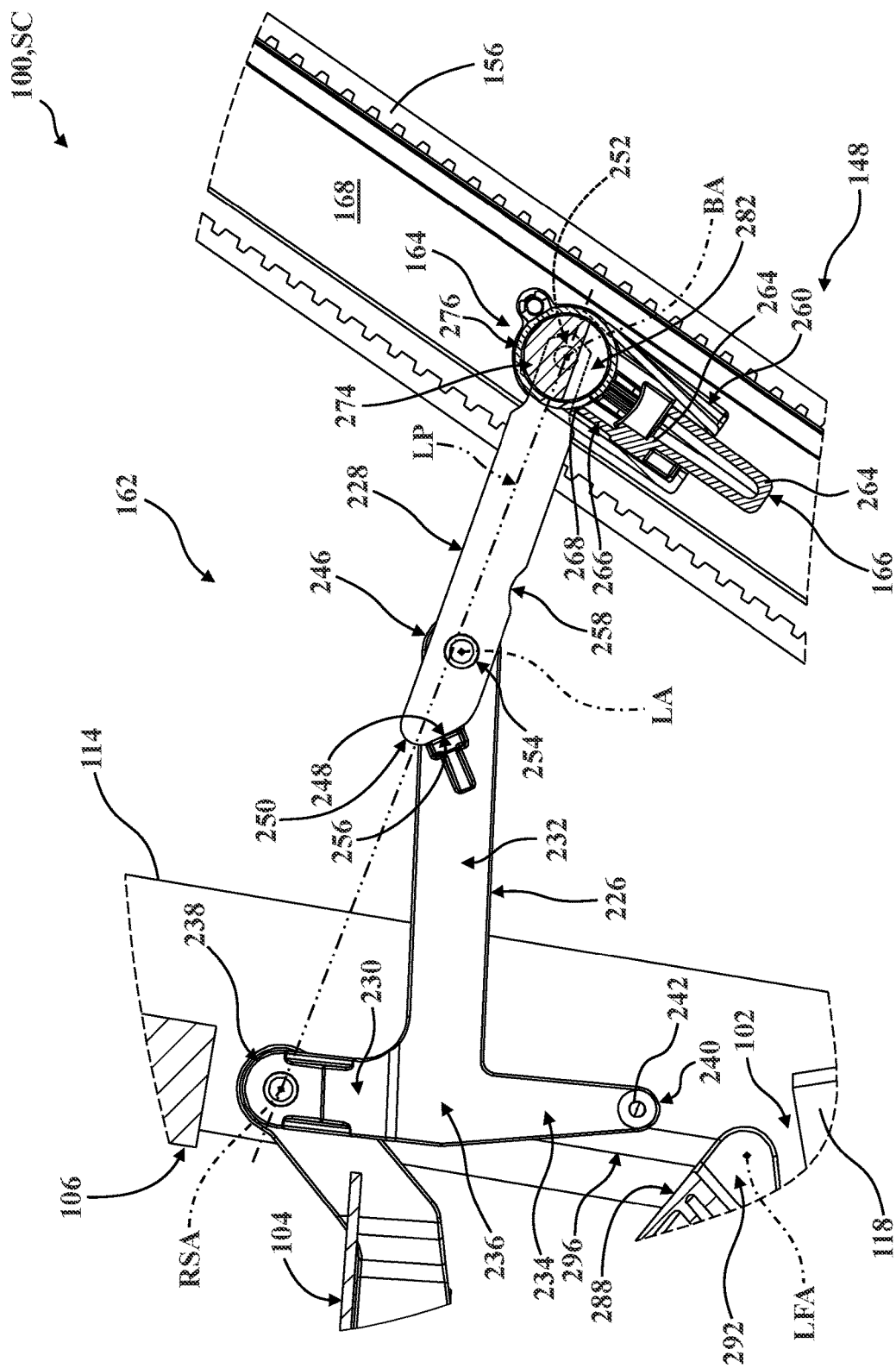
FIG. 9A is a partial section view generally taken through plane 9 of FIGS. 7B-8, shown with the deployment lock mechanism retaining the track assembly in the deployed position.

As is best shown in FIG. 9A, the connecting links 226 each comprise or otherwise define a forward pivot region 230, a connecting pivot region 232, a trunnion region 234, and an interface region 236. The forward pivot regions 230 extend from the interface regions 236 to forward pivot mounts 238 which are pivotably coupled to the rear uprights 114 about the rear seat axis RSA, such as by one or more fasteners, bushings, bearings, and the like (not shown in detail). Here, because the rear uprights 114 are spaced laterally away from each other at a distance large enough to allow the track assemblies 154 to "nest" therebetween in the retracted position 154A (see FIG. 7A), the forward pivot regions 230 of the connecting links 226 extend at an angle away from the rear uprights 114 at least partially laterally towards the track assemblies 154. The trunnion regions 234 extend generally vertically downwardly from the interface regions 236 to trunnion mount ends 240, and comprise trunnions 242 which extend generally laterally and are arranged to abut trunnion catches 244 of the deployment lock mechanism 164 to retain the track assemblies 154 in the retracted position 154A (see FIG. 7A) as described in greater detail below. The connecting pivot regions 232 extend longitudinally away from the interface regions 236 to rearward pivot mounts 246 which pivotably couple to the brace links 228 about a link axis LA. The connecting pivot regions 232 also comprise link stops 248 that are shaped and arranged to abut the brace links 228 in the deployed position 154B (see FIG. 7B), as described in greater detail below. The connecting links 226 are each formed as separate components with mirrored profiles in the illustrated embodiments, but could be realized in other ways, with any suitable number of components.

The brace links 228 each generally extend between an abutment link end 250 and a rearward link mount 252, with a forward link mount 254 arranged therebetween. The forward link mounts 254 are pivotably coupled to the rearward pivot mounts 246 of the connecting links 226 about the link axis LA, such as by one or more fasteners, bushings, bearings, and the like (not shown in detail). The rearward link mounts 252 are each operatively attached to the deployment lock mechanism 164 about a barrel axis BA, as described in greater detail below. The brace links 228 each define a link abutment surface 256 disposed adjacent to the abutment link end 250 which are arranged to abut the link stops 248 of the connecting links 226 in the deployed position 154B (see FIGS. 7B and 9B). The brace links 228 also define a relief region 258 formed between the forward link mount 254 and the rearward link mount 252. The relief regions 258 are shaped to at least partially accommodate the link stops 248 of the connecting links 226 when the track assemblies 154 are in the retracted position 154A (not shown in detail).

Figure 8:
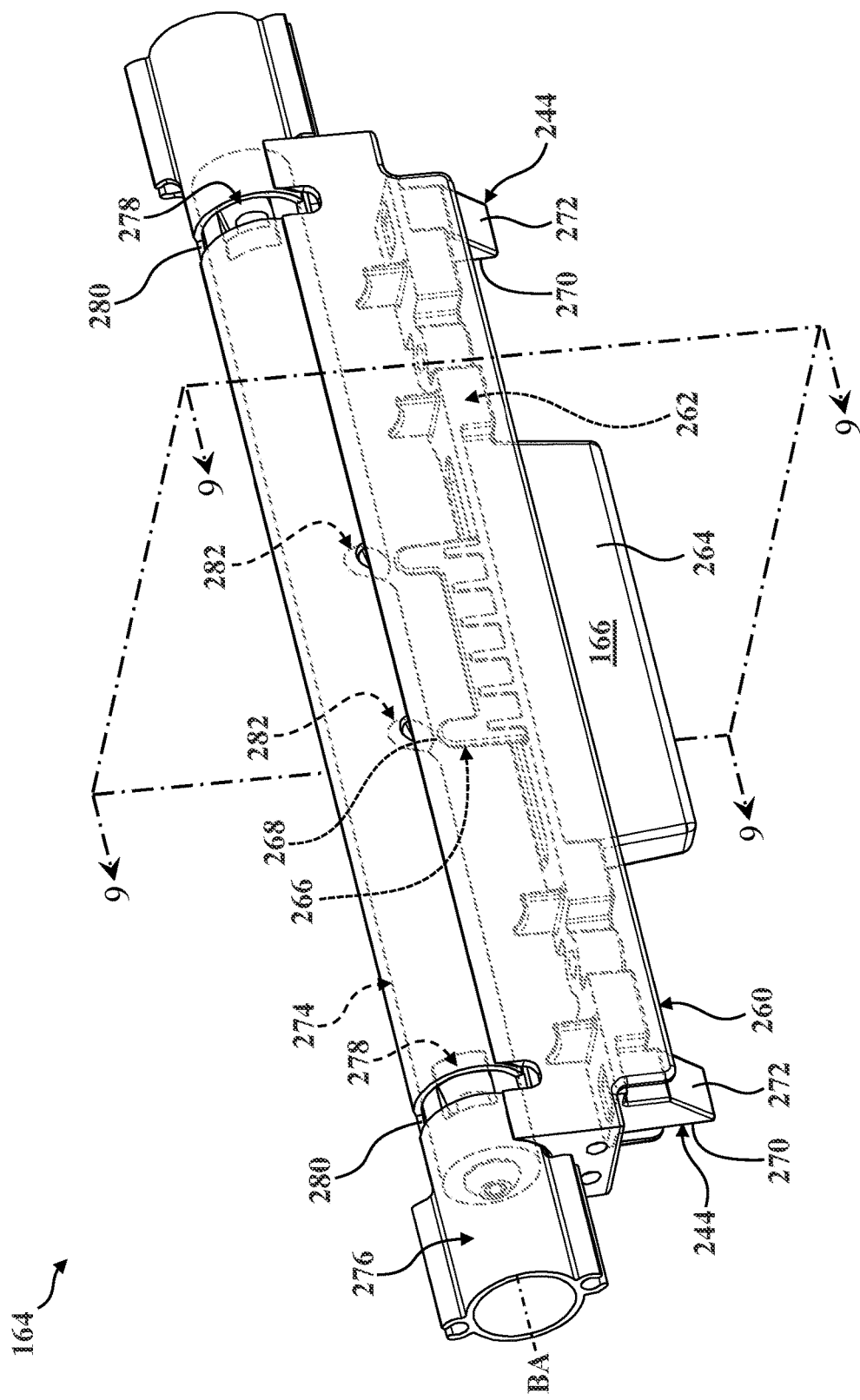
FIG. 8 is a perspective view of portions of the deployment lock mechanism of FIGS. 7A-7B, shown having a deployment lock release.

Referring now to FIG. 8, the deployment lock release 166 of the deployment lock mechanism 164 is supported for movement within a lock housing 260 which, in turn, is coupled to and extends laterally between the rails 168 of the track assemblies 154 (e.g., secured via fasteners; not shown). The deployment lock release 166 is formed as a unitary component in the illustrated embodiment, and generally comprises a deployment body 262, a deployment button 264, one or more push tabs 266, and the trunnion catches 244. The deployment button 264 is arranged for engagement by the caregiver, extends vertically downwardly from the deployment body 262, and is disposed laterally between the trunnion catches 244. The one or more push tabs 266 extend vertically upwardly from the deployment body 262 to respective push tab ends 268, and are employed to facilitate releasing the track assemblies 154 from the deployed position 154B as described in greater detail below. The trunnion catches 244 each define a retention face 270 arranged to abut the trunnions 242 of the connecting links 226 when the track assemblies 154 are in the retracted position 154A (see FIG. 7A; not shown in detail). The trunnion catches 244 also each define a trunnion cam face 272 arranged to engage against the trunnions 242 of the connecting links 226 as the track assemblies 154 are brought toward the deployed position 154B from the retracted position 154A. While not shown in detail throughout the drawings, engagement of the trunnions 242 against the trunnion cam faces 272 urges the deployment body 262 vertically upwardly within the lock housing 260 until the trunnions 242 come out of engagement with the trunnion cam faces 272. Here, one or more biasing elements (not shown) may bias the deployment lock release 166 vertically downwardly within the lock housing 260 such that disengagement of the trunnions 242 with trunnion cam faces 272 occurs as the track assemblies 154 reach the deployed position 154B and the trunnions 242 come into engagement with the retention faces 270 (see FIG. 7A; not shown in detail).

With continued reference to FIG. 8, the deployment lock mechanism 164 also comprises a barrel 274 supported for rotation about the barrel axis BA (compare FIGS. 9A-9B) within a cylinder housing 276 which, in turn, is coupled to and extends laterally between the rails 168 of the track assemblies 154 (e.g., secured via fasteners; not shown). The barrel 274 defines barrel notches 278 which receive the rearward link mounts 252 of the brace links 228 therein. Here, the cylinder housing 276 comprises transverse apertures 280 aligned laterally with the barrel notches 278 and shaped to receive the brace links 228 therethrough to permit the brace links 228 to move generally concurrently with the barrel 274 relative to the cylinder housing 276. Here, the barrel notches 278 and the rearward link mounts 252 are provided with complimentary profiles that allow the brace links 228 to pivot about the barrel axis BA as the barrel 274 rotates within the cylinder housing 276. The barrel notches 278 may be sized slightly larger than the rearward link mounts 252 to prevent binding. However, it will be appreciated that other configurations are contemplated. The barrel 274 also comprises push notches 282 arranged laterally between the barrel notches 278. The push notches 282 are shaped to receive the push tab ends 268 of the push tabs 266 to facilitate releasing the track assemblies 154 from the deployed position 154B in response to the caregiver engaging the deployment button 264. As depicted in FIG. 9A, retention of the track assemblies 154 in the deployed position 154B is achieved based on the geometry of the deployment linkage 162 acting as an "over center" lock.

Figure 9B:
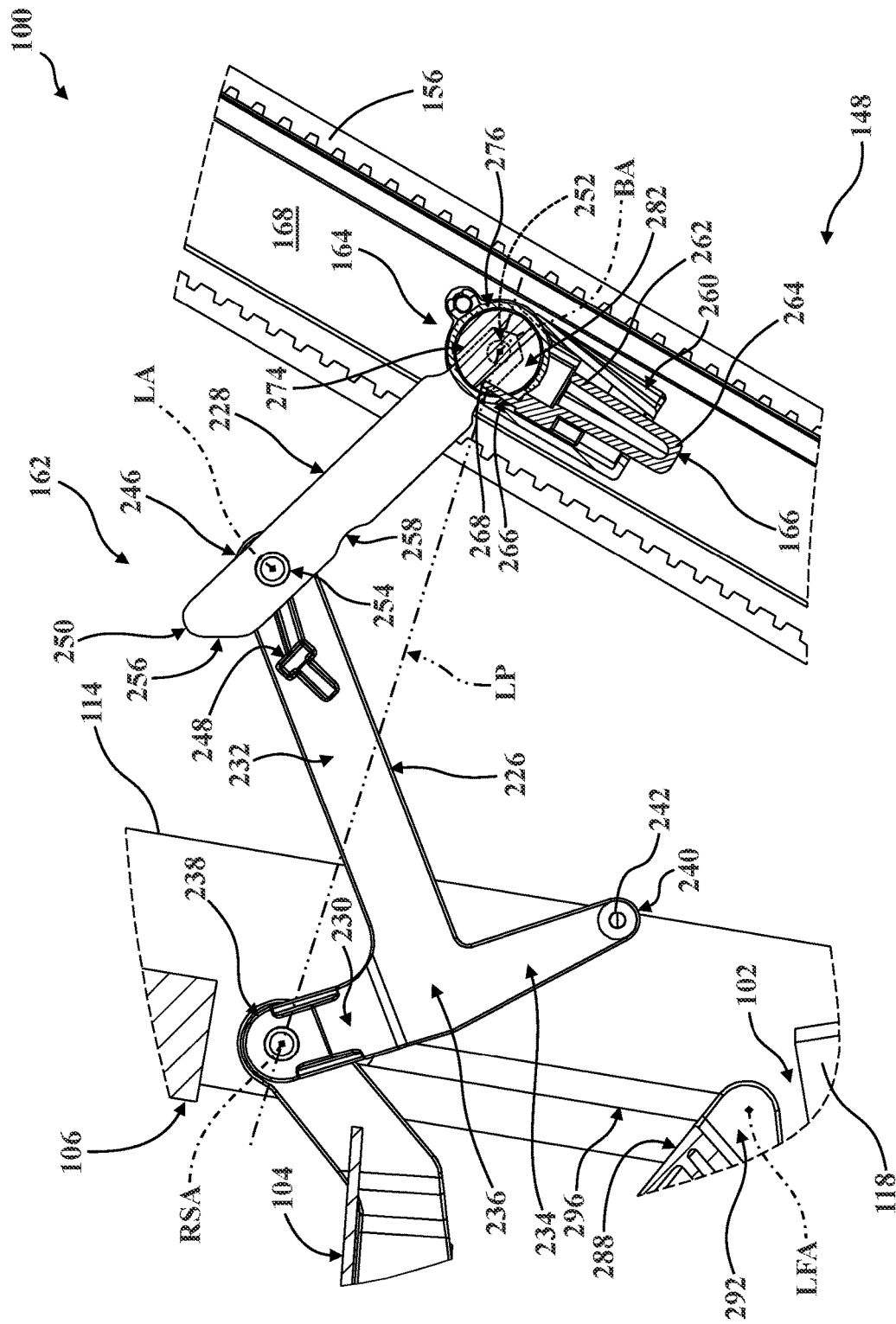
FIG. 9B is another partial section view of the portions of the patient transport apparatus depicted in FIG. 9A, shown with the track assembly having moved from the deployed position in response to engagement of the deployment lock release of the deployment lock mechanism.

More specifically, when the track assemblies 154 move to the deployed position 154B, the link axis LA is arranged below a linkage plane LP defined extending through the rear seat axis RSA and the barrel axis BA, and will remain in the deployed position 154B until the link axis LA is moved above the linkage plane LP (see FIG. 9B). To this end, the caregiver can engage the deployment button 264 to bring the push tab ends 268 of the push tabs 266 into engagement with the push notches 282 formed in the barrel 274 which, in turn, rotates the barrel 274 about the barrel axis BA as the push tab ends 268 contact the barrel 274 within the push notches 282, and pivots the brace links 228 about the barrel axis BA to cause the link axis LA to move above the linkage plane LP as shown in FIG. 9B. It will be appreciated that the deployment lock mechanism 164 could be configured in other ways sufficient to releasably lock the track assemblies 154 in the retracted position 154A and the deployed position 154B, and it is contemplated that one lock mechanism could lock the track assemblies 154 in the retracted position 154A while a different lock mechanism could lock the track assemblies 154 in the deployed position 154B. Other configurations are contemplated.

Figure 10:
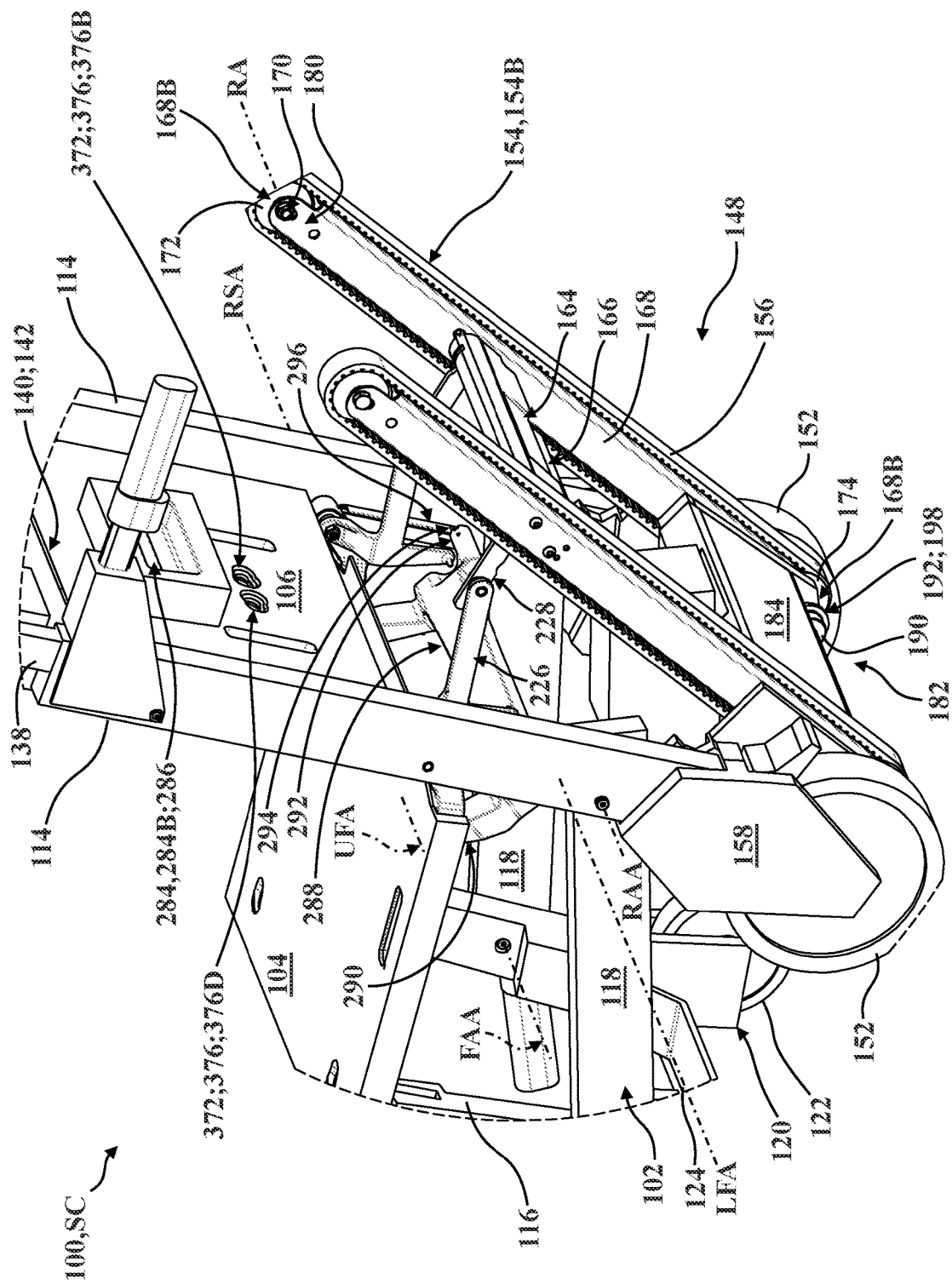
FIG. 10 is a partial rear perspective view of the patient transport apparatus of FIGS. 1-9B, showing additional detail of the folding lock mechanism.
Figure 11A:
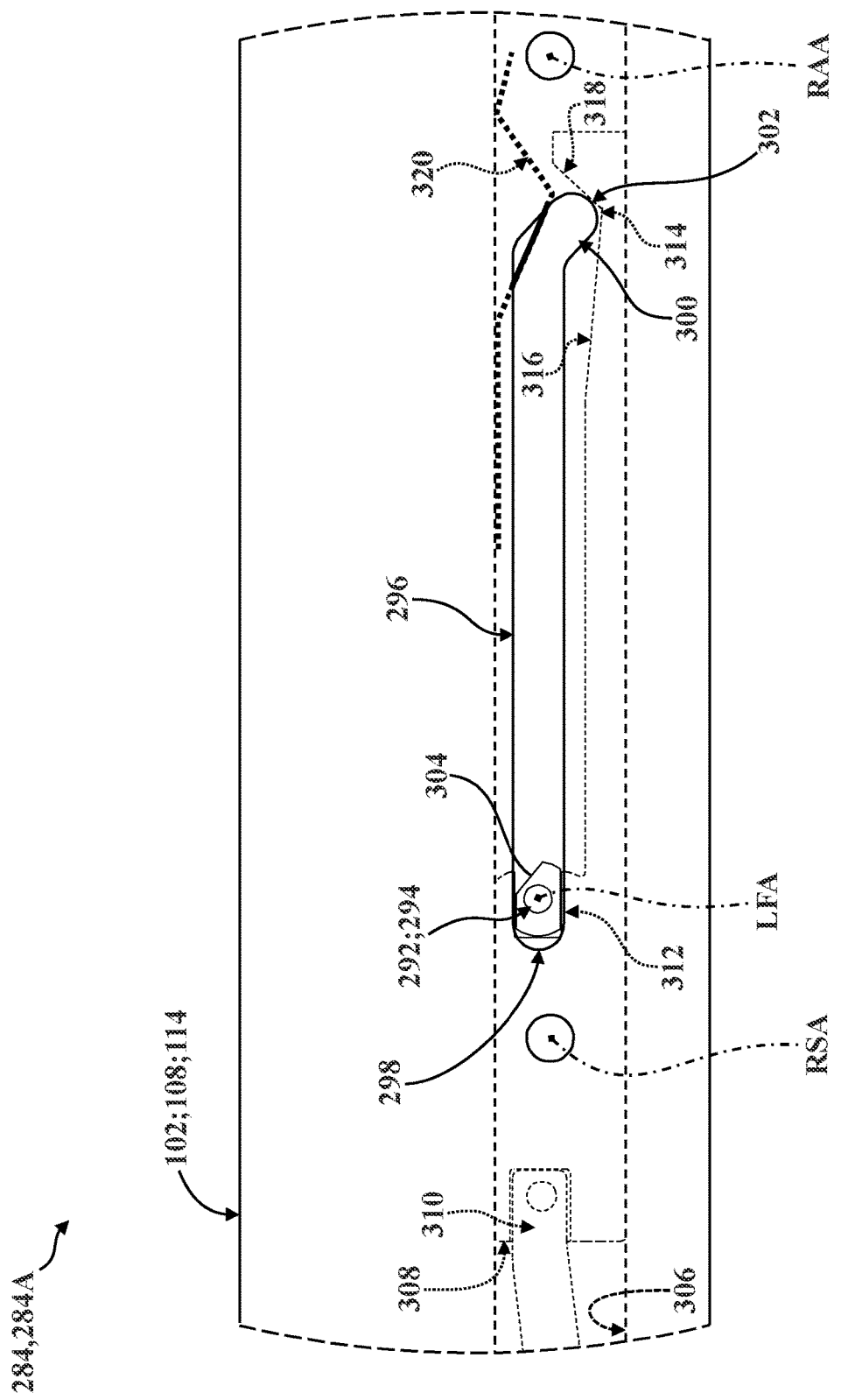
FIG. 11A is a partial schematic view of portions of the folding lock mechanism of the patient transport apparatus of FIGS. 1-10, shown arranged in a stow lock configuration corresponding to the stowed configuration as depicted in FIG. 5.
Figure 11B:
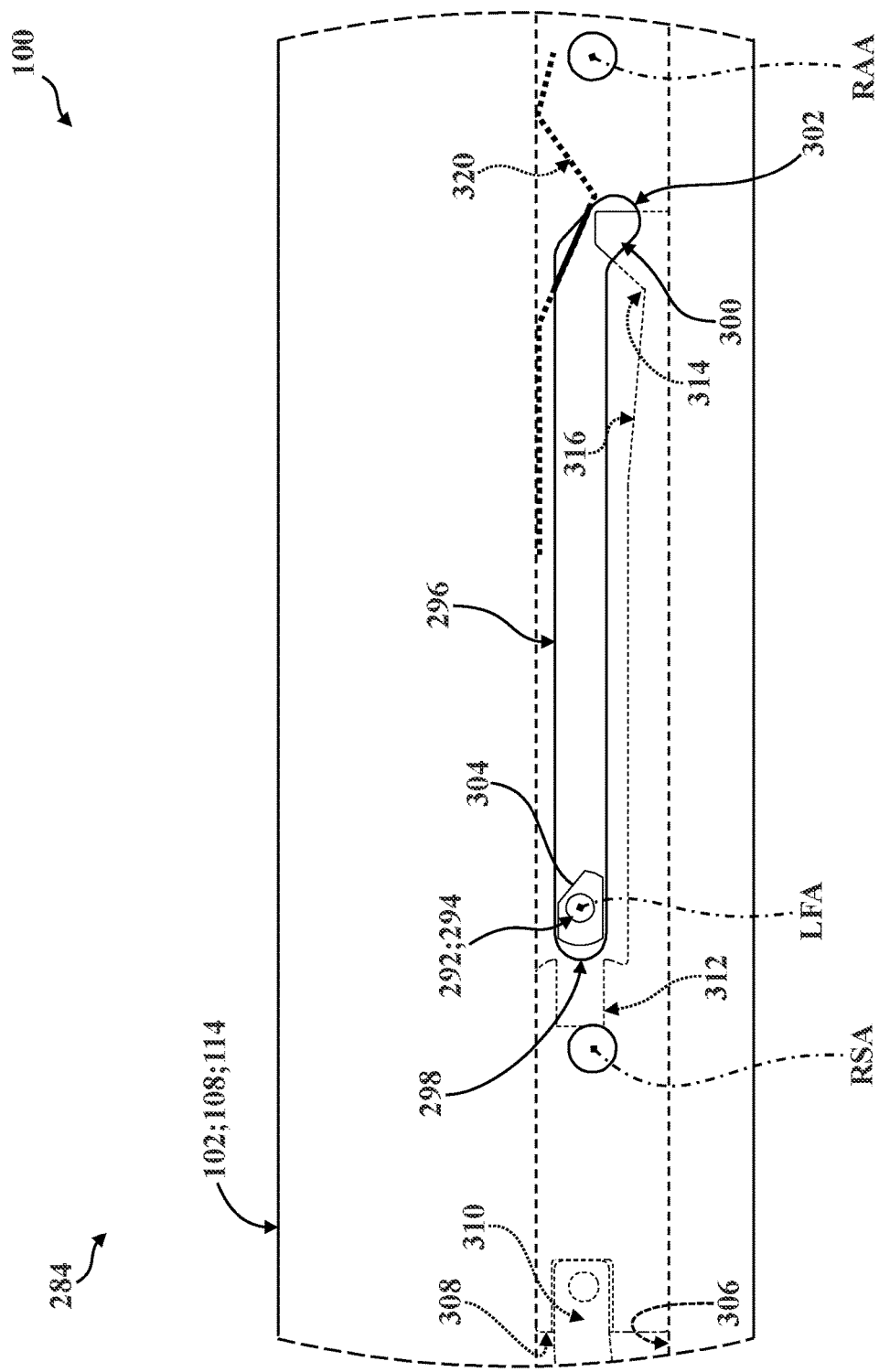
FIG. 11B is another partial schematic view of the portions of the folding lock mechanism of FIG. 11A, shown having moved out of the stow lock configuration to enable operation in the chair configuration as depicted in FIG. 6A.
Figure 11C:
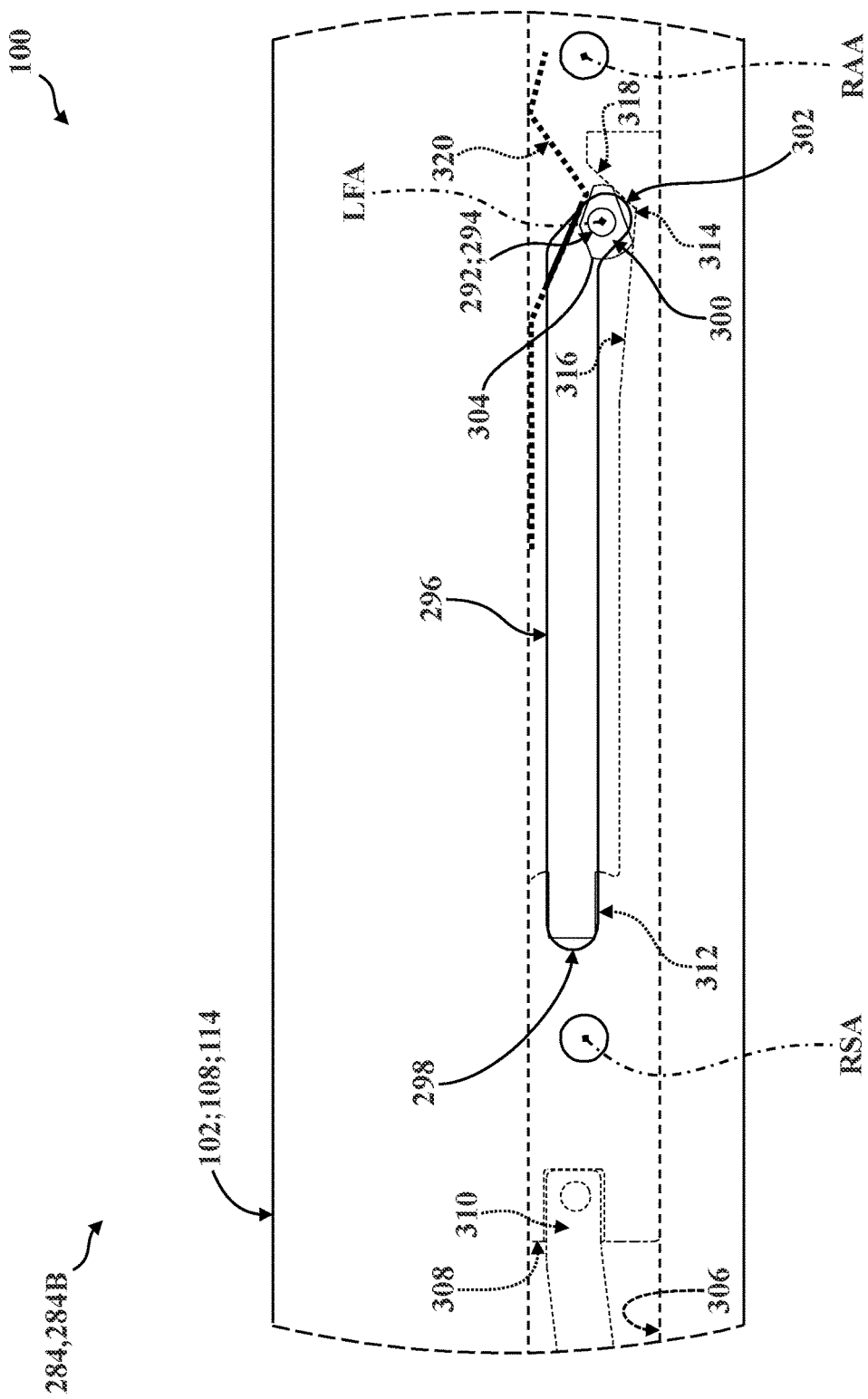
FIG. 11C is another partial schematic view of the portions of the folding lock mechanism of FIGS. 11A-11B, shown arranged in a use lock configuration corresponding to the chair configuration as depicted in FIG. 6A.
Figure 11D:
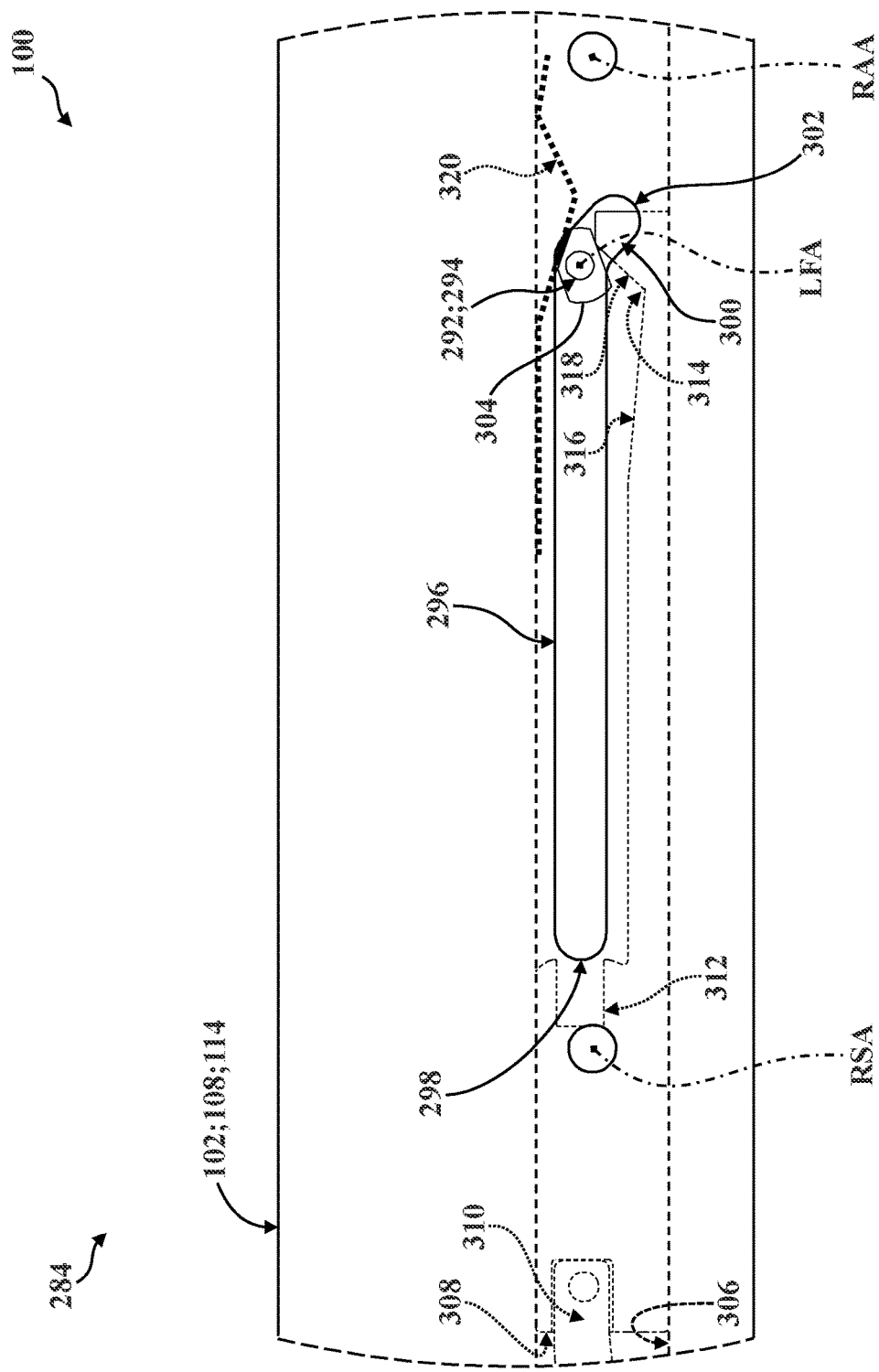
FIG. 11D is another partial schematic view of the portions of the folding lock mechanism of FIGS. 11A-11C, shown having moved out of the use lock configuration to enable operation in the stowed configuration as depicted in FIG. 5.

Referring now to FIGS. 10-11D, the patient transport apparatus 100 employs a folding lock mechanism 284 to facilitate changing between the stowed configuration WC (see FIG. 5) and the chair configuration CC (see FIG. 6A). To this end, the folding lock mechanism 284 generally comprises a folding lock release 286 (see FIG. 10) operatively attached to the back section 106 and arranged for engagement by the caregiver to releasably secure the folding lock mechanism 284 between a stow lock configuration 284A to maintain the stowed configuration WC, and a use lock configuration 284B to prevent movement to the stowed configuration WC from the chair configuration CC or from the stair configuration SC. To this end, the folding lock mechanism 284 generally comprises a folding link 288 with folding pivot mounts 290 and sliding pivot mounts 292. The folding pivot mounts 290 are pivotably coupled to the seat section 104 about an upper folding axis UFA that is arranged between the rear seat axis RSA and the front seat axis FSA (see FIGS. 2 and 6A-6B; pivoting not shown in detail). The sliding pivot mounts 292 each comprise a keeper shaft 294 which extends along a lower folding axis LFA which is arranged substantially parallel to the upper folding axis UFA. The keeper shafts 294 are disposed within and slide along slots 296 formed in each of the rear uprights 114. For the illustrative purposes, the keeper shafts 294 are shown in FIGS. 11A-11D as sized significantly smaller than the width of the slots 296. The slots 296 extend generally vertically along the rear uprights 114 between an upper slot end 298 and a transition slot region 300, and extend at an angle from the transition slot region 300 to a lower slot end 302. The slots 296 are disposed vertically between the rear seat axis RSA and the rear arm axis RAA in the illustrated embodiment. In some embodiments, the folding link 288, the slots 296, and or other portions of the folding lock mechanism 284 may be similar to as is disclosed in U.S. Pat. No. 6,648,343, previously referenced. Other configurations are contemplated.

In the representative embodiment illustrated herein, the folding lock mechanism 284 is configured to selectively retain the keeper shafts 294 adjacent to the upper slot ends 298 of the slots 296 in the stow lock configuration 284A (see FIG. 11A), and to selectively retain the keeper shafts 294 adjacent to the lower slot ends 302 of the slots 296 in the use lock configuration 284B (see FIG. 11C). To this end, keeper elements 304 are coupled to the keeper shafts 294 and move within upright channels 306 formed in the rear uprights 114. Here too, a carriage 308 is slidably supported within the upright channels 306 for movement relative to the slots 296 in response to engagement of the folding lock release 286 via the caregiver. A folding linkage assembly 310 generally extends in force-translating relationship between the folding lock release 286 and the carriage 308. While not shown in detail, the folding lock release 286 is supported by the back section 106 and moves in response to engagement by the caregiver, and the folding linkage assembly 310 comprises one or more components which may extend through the back section 106 and into the rear uprights 114 in order to facilitate movement of the carriage 308 within the upright channels 306 in response to user engagement of the folding lock release 286. As will be appreciated from the subsequent description below, FIGS. 11A and 11C represent an absence of user engagement with the folding lock release 286, whereas FIGS. 11B and 11D represent user engagement with the folding lock release 286.

The carriage 308 generally defines an upper pocket 312 shaped to receive and accommodate the keeper element 304 when the folding lock mechanism 284 is in the stow lock configuration 284A with the patient transport apparatus 100 arranged in the stowed configuration WC, and a lower pocket 314 shaped to receive and accommodate the keeper element 304 when the folding lock mechanism 284 is in the use lock configuration 284B with the patient transport apparatus 100 arranged in the chair configuration CC or in the stair configuration SC. In the illustrated embodiment, the upper pocket 312 has a generally U-shaped profile and the lower pocket 314 has a generally V-shape profile which defines an upper ramp 316 and a lower ramp 318. The keeper element 304 has a par of substantially parallel sides which are shaped to be received within the upper pocket 312 (not shown in detail).

As shown in FIG. 11A, engagement between the keeper element 304 and the upper pocket 312 of the carriage 308 prevents movement of the keeper shaft 294 along the slot 296. When the caregiver engages the folding lock release 286 to move the folding lock mechanism 284 out of the stow lock configuration 284A, the corresponding movement of the folding linkage assembly 310 causes the carriage 308 to travel vertically upwardly within the upright channel 306 until the keeper element 304 comes out of engagement with the upper pocket 312, as shown in FIG. 11B. Here, the keeper shaft 294 can subsequently traverse the slot 296 toward the lower slot end 302 in order to move to the use lock configuration 284B depicted in FIG. 11C (movement not shown; compare FIG. 11B to FIG. 11C). While not shown, it will be appreciated that the carriage 308, the folding linkage assembly 310, and or the folding lock release 286 may comprise one or more biasing elements arranged to urge the carriage 308 vertically down the upright channel 306.

When in the use lock configuration 284B depicted in FIG. 11C, the keeper shaft 294 is disposed adjacent to the lower slot end 302 of the slot 296 such that the keeper element 304 is generally disposed adjacent to or otherwise in the lower pocket 314, such as in contact with the upper ramp 316 and the lower ramp 318. Here, the keeper element 304 is retained via a folding lock biasing element 320 (depicted schematically) that is coupled to the rear upright 114 (e.g., disposed within the upright channel 306). To this end, the keeper element 304 has a notch side that abuts the folding lock biasing element 320 and is arranged transverse (e.g., non-parallel) to the two parallel sides (not shown in detail). The engagement between the keeper element 304 and folding lock biasing element 320 urges the keeper shaft 294 toward the lower slot end 302 of the slot 296 to maintain operation in the use lock configuration 284B depicted in FIG. 11C. When the caregiver engages the folding lock release 286 to move the folding lock mechanism 284 out of the use lock configuration 284B, the corresponding movement of the folding linkage assembly 310 causes the carriage 308 to travel vertically upwardly within the upright channel 306. Here, as the lower ramp 318 of the carriage 308 defined by the lower pocket 314 moves together with the keeper element 304 disposed in engagement therewith, the folding lock biasing element 320 compresses as the keeper shaft 294 travels out of the transition slot region 300, as shown in FIG. 11D. Here, the keeper shaft 294 can subsequently traverse the slot 296 toward the upper slot end 298 in order to move to the stow lock configuration 284A depicted in FIG. 11A (movement not shown; compare FIG. 11D to FIG. 11A). It will be appreciated that the folding lock mechanism 284 could be configured in other ways sufficient to releasably lock the patient transport apparatus in the stowed configuration WC, the stair configuration SC, and the chair configuration CC, and it is contemplated that one lock mechanism could lock the patient transport apparatus 100 in the stowed configuration WC while a different lock mechanism could lock the patient transport apparatus 100 in the stair configuration SC and/or the chair configuration CC. Other configurations are contemplated.

FIGS. 12A-12I successively depict exemplary steps of transporting a patient supported on the patient transport apparatus 100 down stairs ST. In FIG. 12A, a first caregiver is shown engaging the pivoting handle assemblies 130 in the engagement position 130B to illustrate approaching stairs ST while the patient transport apparatus 100 is moved along floor surfaces FS in the chair configuration CC. FIG. 12B depicts a second caregiver engaging the front handle assemblies 128 after having moved them to the extended position 128B. In FIG. 12C, the patient transport apparatus 100 has been moved closer to the stairs ST with the first caregiver still engaging the pivoting handle assemblies 130 and with the second caregiver still engaging the front handle assemblies 128. In FIG. 12D, the first caregiver has moved the handle assembly 132 to the extended position 132B as the second caregiver continues to engage the front handle assemblies 128.

In FIG. 12E, the first caregiver has engaged the deployment lock release 166 to move the patient transport apparatus 100 out of the chair configuration CC and into the stair configuration SC. Here, the track assemblies 154 are shown arranged between the retracted position 154A and the deployed position 154B, and the rear wheels 152 move closer to the front wheels 122, as the first caregiver pulls the track assemblies 154 away from the back section 106. In FIG. 12F, the patient transport apparatus 100 is shown in the stair configuration SC with the track assemblies 154 arranged in the deployed position 154B. Here, the rear wheels 152 are positioned significantly closer to the front wheels 122 compared to operation in the chair configuration CC, and are also arranged further under the seat section 104. It will be appreciated that transitioning the patient transport apparatus 100 from the chair configuration CC to the stair configuration SC has resulted in minimal patient movement relative to the support structure 102 as the carrier assembly 148 pivots about the hub axis HA and moves the rear wheels 152 closer to the front wheels 122 in response to movement of the track assemblies 154 to the deployed position 154B.

Furthermore, while the arrangement of patient's center of gravity has not changed significantly relative to the support structure 102, the longitudinal distance which extends between the patient's center of gravity and the location at which the rear wheels 152 contact the floor surface FS has shortened considerably. Because of this, the process of "tilting" the patient transport apparatus 100 (e.g., about the rear wheels 152) to transition toward contact between the track assemblies 154 and the stairs ST, as depicted in FIG. 12G, is significantly more comfortable for the patient than would otherwise be the case if the patient transport apparatus 100 were "tilted" about the rear wheels 152 from the chair configuration CC (e.g., with the rear wheels 152 positioned further away from the front wheels 122). Put differently, the arrangement depicted in FIG. 12G is such that the patient is much less likely to feel uncomfortable, unstable, or as if they are "falling backwards" during the "tilting" process. Here too, the caregivers are afforded with similar advantages in handling the patient transport apparatus 100, as the arrangement of the rear wheel 152 described above also makes the "tilting" process easier to control and execute.

In FIG. 12H, the caregivers are shown continuing to support the patient transport apparatus 100 in the stair configuration SC as the belts 156 of the track assemblies 154 are brought into contact with the edge of the top stair ST. In FIG. 12I, the caregivers are shown continuing to support the patient transport apparatus 100 in the stair configuration SC as the belts 156 of the track assemblies 154 contact multiple stairs ST during descent.

Figure 13A:
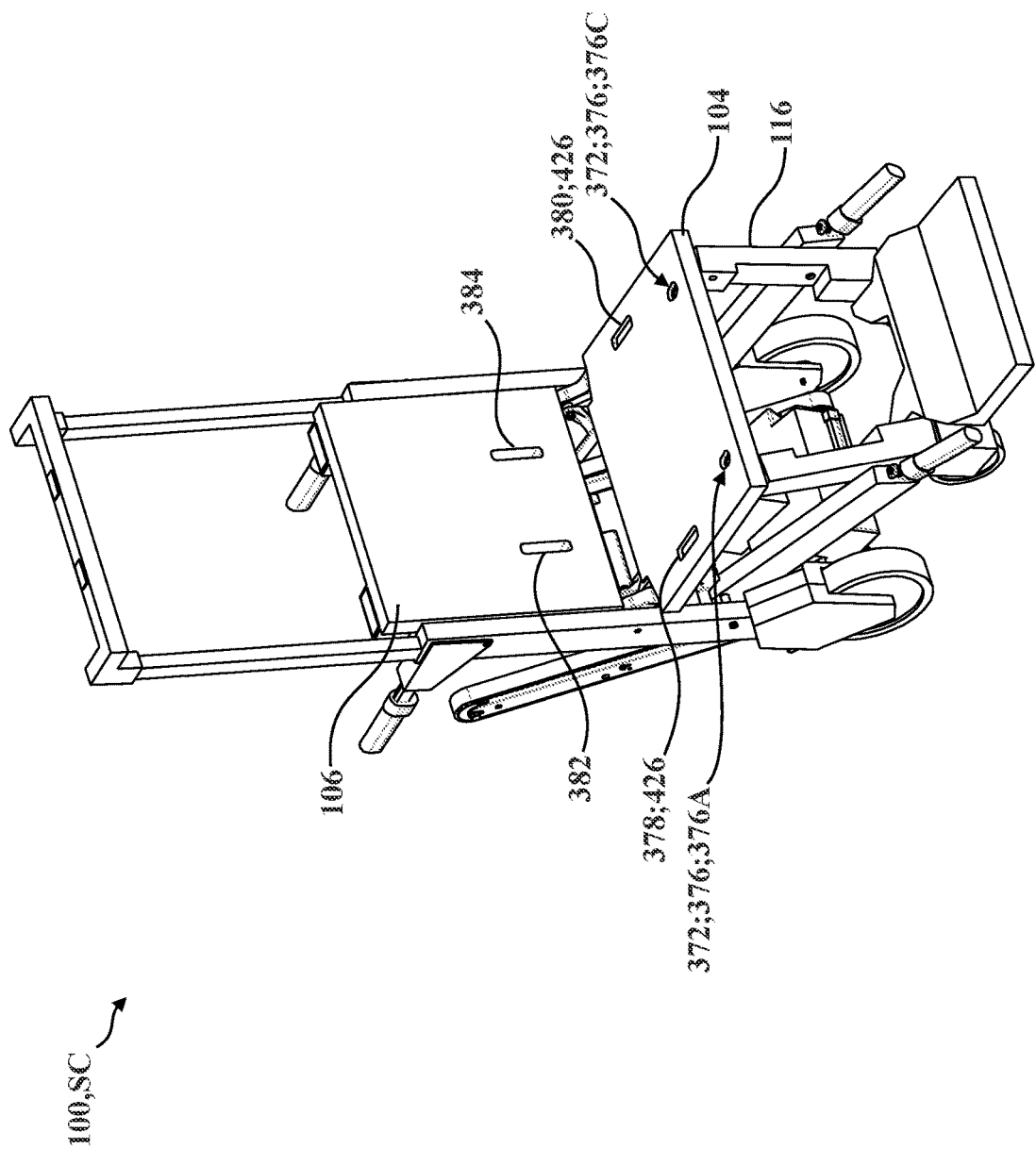
FIG. 13A is another perspective view of the patient transport apparatus of FIGS. 1-12I, shown with a plurality of receivers for use with a patient containment system according to the present disclosure.
Figure 13B:
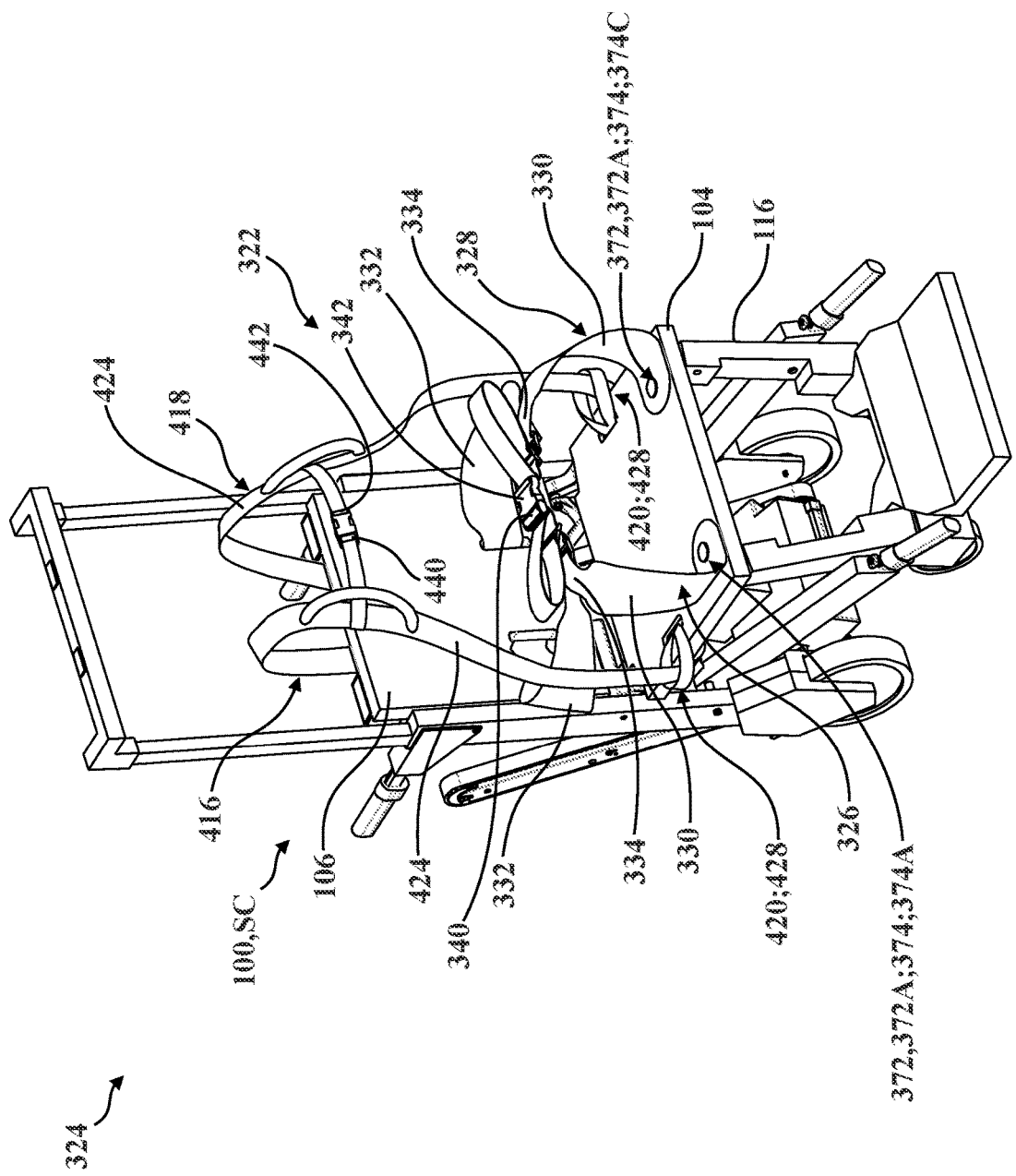
FIG. 13B is another partial perspective view of the patient transport apparatus of FIG. 13A, shown with a patient containment system secured to the patient transport apparatus to define a patient transport system.
Figure 14:
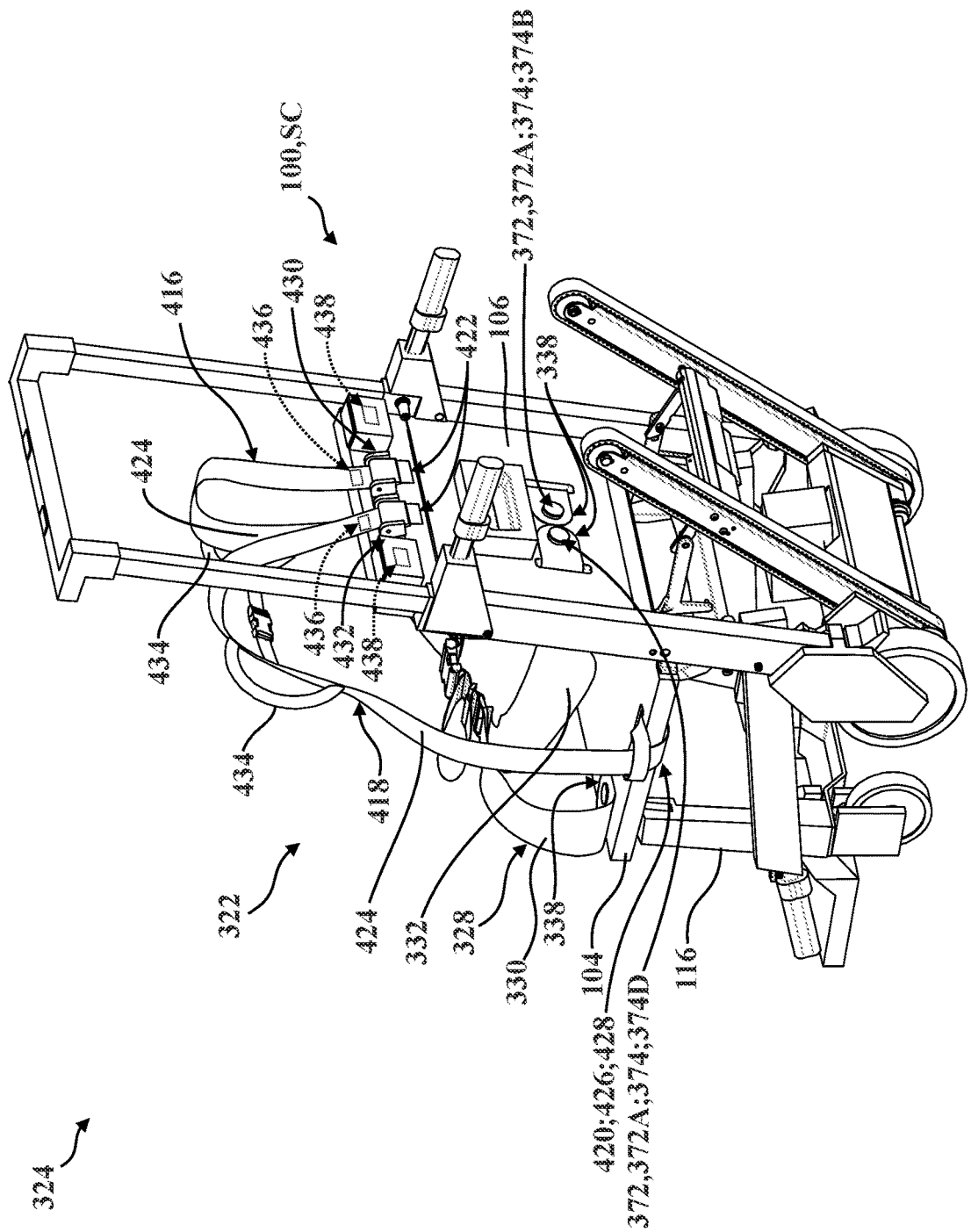
FIG. 14 is another partial perspective view of the patient transport system of FIG. 13B.

Referring now to FIGS. 13A-18C, a patient containment system 322 to secure the patient to the patient transport apparatus 100 is generally shown. The patient containment system 322 may be removably engaged, coupled, or otherwise attached to the patient transport apparatus 100 to define a patient transport system 324 according to the present disclosure. FIGS. 13B-14 depict the patient transport system 324 with the patient containment system 322 engaged with the patient transport apparatus 100. The patient containment system 322 may function to retain a patient supported for transport on the patient transport apparatus 100, particularly during transport up or down stairs ST and/or during ingress or egress into or out of a structure (e.g., a home or building).

Figure 15A:
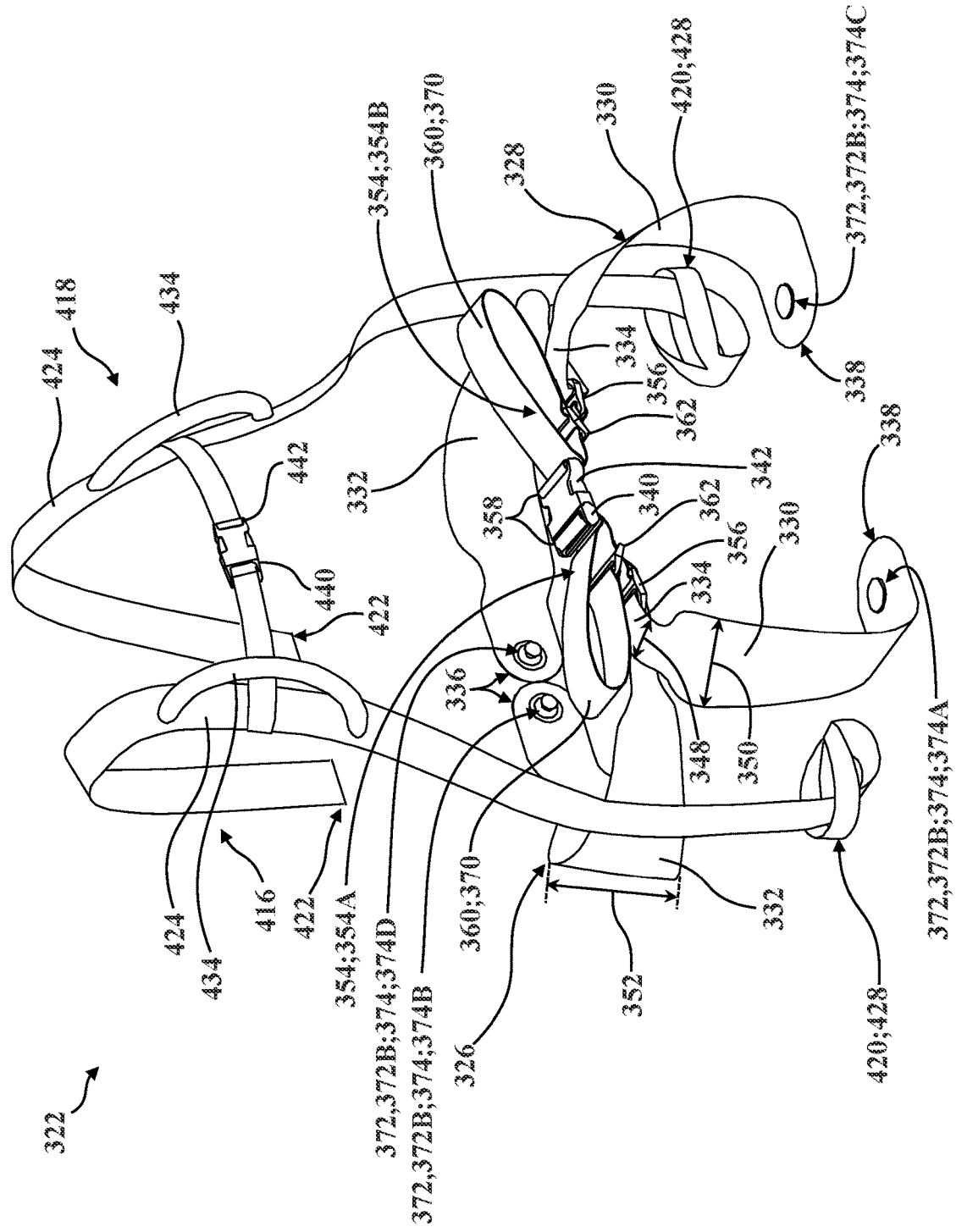
FIG. 15A is a perspective view of the patient containment system of FIGS. 13B-14, shown comprising upper straps, and lower straps having anchors for engaging the receivers of the patient transport apparatus of FIG. 13A.
Figure 15B:
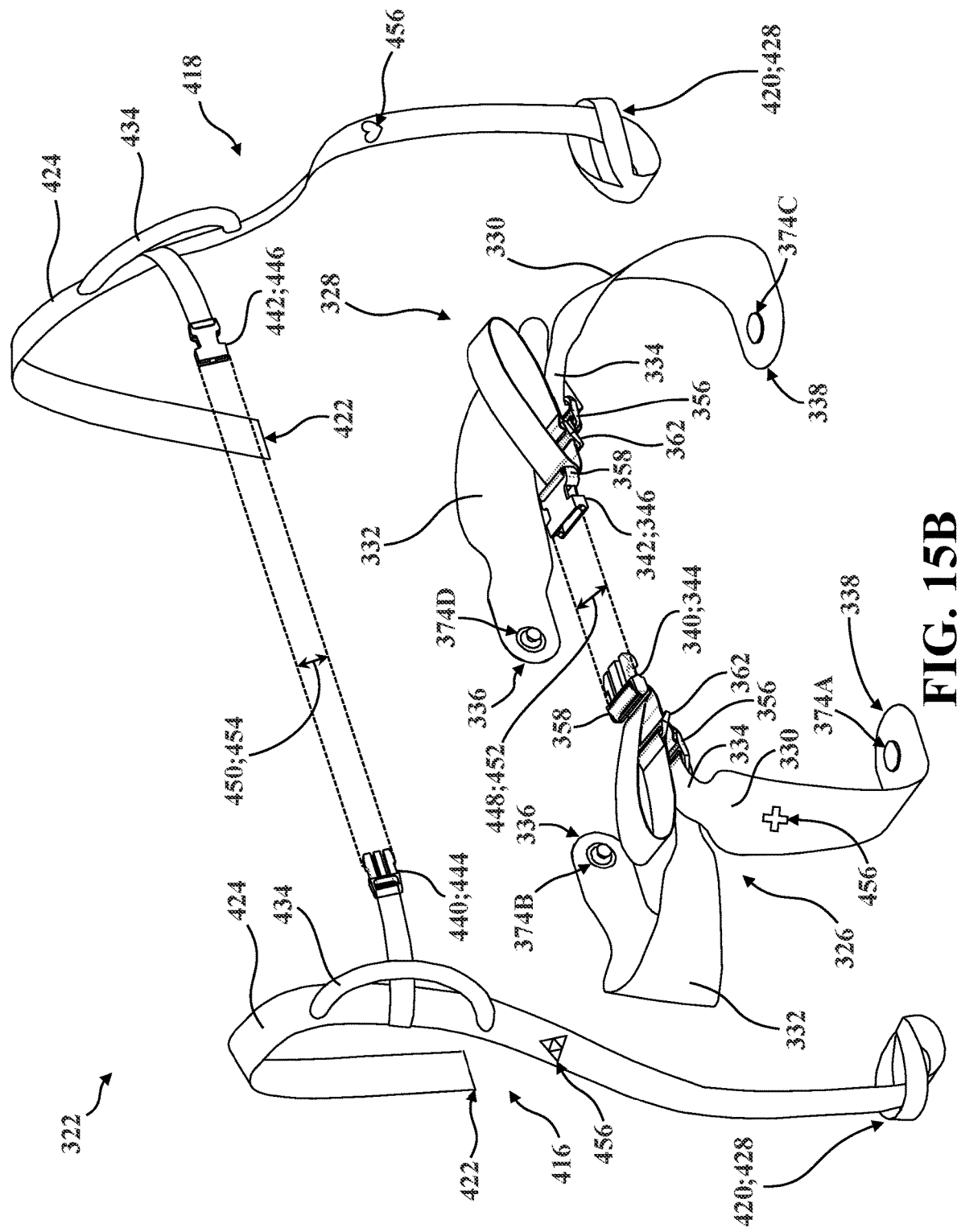
FIG. 15B is a partially-exploded perspective view of the patient containment system of FIG. 15A.

The patient containment system 322 is designed to secure patients of various sizes through the use of straps which are removably attachable to the patient transport apparatus 100. To this end, and as is best depicted in FIGS. 15A-15B, in some embodiments, the patient containment system 322 may comprise a first lower strap 326 and a second lower strap 328 each having a respective thigh region 330, waist region 332, and connection region 334 arranged between an rear lower strap end 336 and a front lower strap end 338. The connection region 334 is arranged between the thigh region 330 and the waist region 332, the thigh region 330 is arranged between the connection region 334 and the front lower strap end 338, and the waist region 332 is arranged between the connection region 334 and the rear lower strap end 336.

A first connector 340 is coupled to the connection region 334 of the first lower strap 326, and a second connector 342 is coupled to the connection region 334 of the second lower strap 328. The connectors 340, 342 cooperate to facilitate releasably attaching the first lower strap 326 and second lower strap 328 together to at least partially limit movement of the first lower strap 326 relative to the second lower strap 328 (and/or relative to each other). In the representative embodiment illustrated herein, one of the first and second connectors 340, 342 is realized as a lower clasp 344, and the other of the first and second connectors 340, 342 is realized as a lower buckle 346 configured to releasably secure to the lower clasp 344. However, and as will be appreciated from the subsequent description below, the first and second connectors 340, 342 could be configured in a number of different ways sufficient to limit movement between the first and second lower straps 326, 328.

With continued reference to FIGS. 15A-15B, for each of the first and second lower straps 326, 328, the connection region 334 defines a connection width 348, the thigh region 330 defines a thigh width 350, and the waist region 332 defines a waist width 352. As is described in greater detail below, the thigh width 350 and the waist width 352 are advantageously configured to help keep a patient contained during transport on the patient transport apparatus 100 while, at the same time, promoting improved patient comfort and the reduction of pressure marks (e.g., for larger patients) while still being configured to accommodate patients of varying sizes. In some embodiments, the thigh width 350 may be wider than the connection width 348. The thigh width 350 may be 50% or more larger than the connection width 348. In one example, the thigh width 350 is 4 inches and is twice as large as the connection width 348 which is 2 inches. Similarly, the waist width 352 may be larger than the connection width 348. In some embodiments, the waist width 352 may be equal to or less than the thigh width 350, or may be larger than the thigh width 350. Other configurations are contemplated.

It will be appreciated that the thigh regions 330, the waist regions 332, and the connection regions 334 could be formed or otherwise defined in a number of different ways. By way of non-limiting example, the first and second lower straps 326, 328 could each be formed as unitary, one piece components between the rear lower strap end 336 and the front lower strap end 338, which taper or otherwise transition between the thigh region 330, the connection region 334, and the waist region 332. It is also contemplated that the first and second lower straps 326, 328 could be respectively formed from multiple components that are secured together (e.g., welded, bonded, adhered, and the like) and cooperate to define the thigh region 330, the connection region 334, and the waist region 332. By way of non-limiting example, a strap defining the connection width 348 could extend between the rear lower strap end 336 and the front lower strap end 338, and separate components that are secured to the strap could define the thigh region 330 and/or the waist region 332 (not shown). Other configurations are contemplated. In some embodiments one or more portions of the patient containment system 322 may comprise polymeric material, such as polyurethane, or other suitable materials to ease cleaning, and may comprise multiple materials (e.g., coated fabric). The components of the patient containment system 322 may provide a smooth, continuous, outer surface for wiping and thereby cleaning, and may be waterproof, water-resistant, and/or impervious to contaminants, such as dirt, grease, and body fluids. Other configurations are contemplated.

In the representative embodiment illustrated herein, the patient containment system 322 includes a tensioner assembly 354 operatively attached to the first connector 340 and/or to the second connector 342. The tensioner assembly 354 may adjust tension between the first and second lower straps 326, 328 (e.g., between the connection regions 334). For example, the tensioner assembly 354 may be operatively attached to the first connector 340 to adjust tension between the connection region 334 of the first lower strap 326 and the connection region 334 of the second lower strap 328. In some embodiments, each of the first and second lower straps 326, 328 each include a respective tensioner assembly 354. Put differently, in some embodiments, a first tensioner assembly 354A is operatively attached to the connection region 334 of the first lower strap 326, and a second tensioner assembly 354B is operatively attached to the connection region 334 of the second lower strap 328. This configuration allows the tension between the connection regions 334 to be adjusted at each of the first and second lower straps 326, 328. However, other configurations are contemplated, and it will be appreciated that a single tensioner assembly 354 could be employed.

Figure 16:
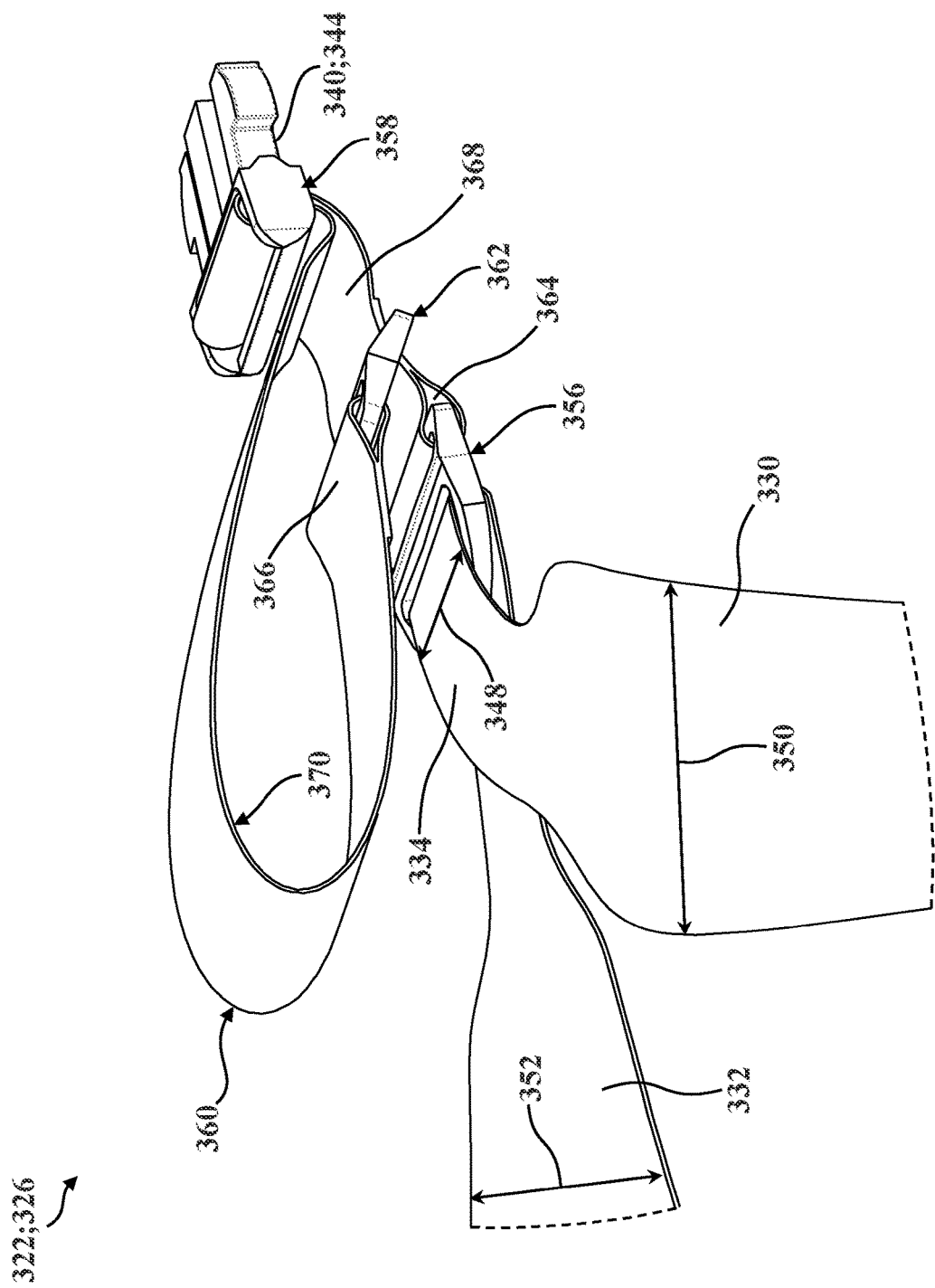
FIG. 16 is a partial perspective view of one of the lower straps of the patient containment system of FIGS. 13B-15B.
Figure 17A:
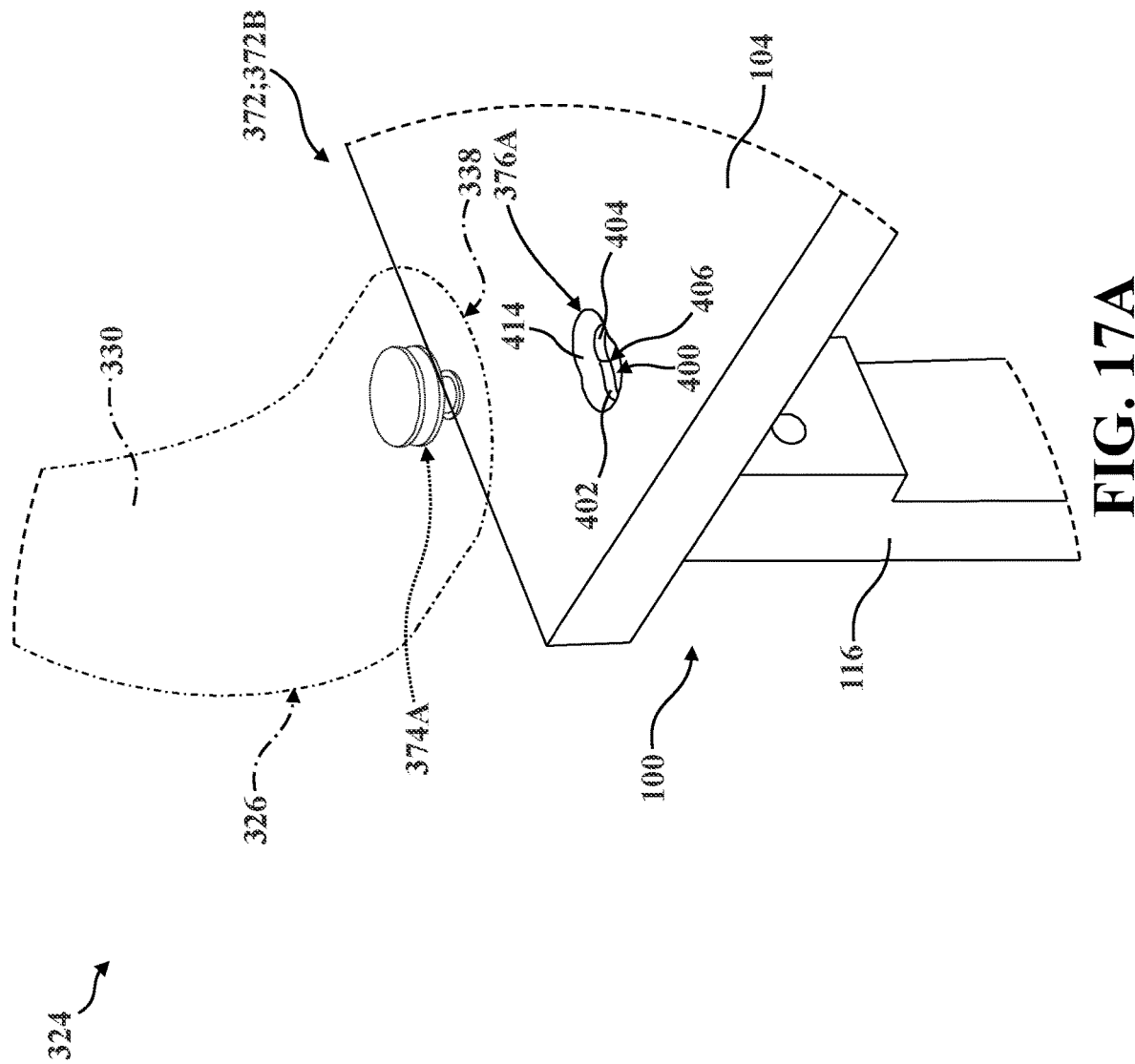
FIG. 17A is a partial perspective view of components of the patient transport system of FIGS. 13A-16, shown with one of the lower straps and one of the anchors depicted in phantom and arranged above one of the receivers of the patient transport apparatus.
Figure 17B:
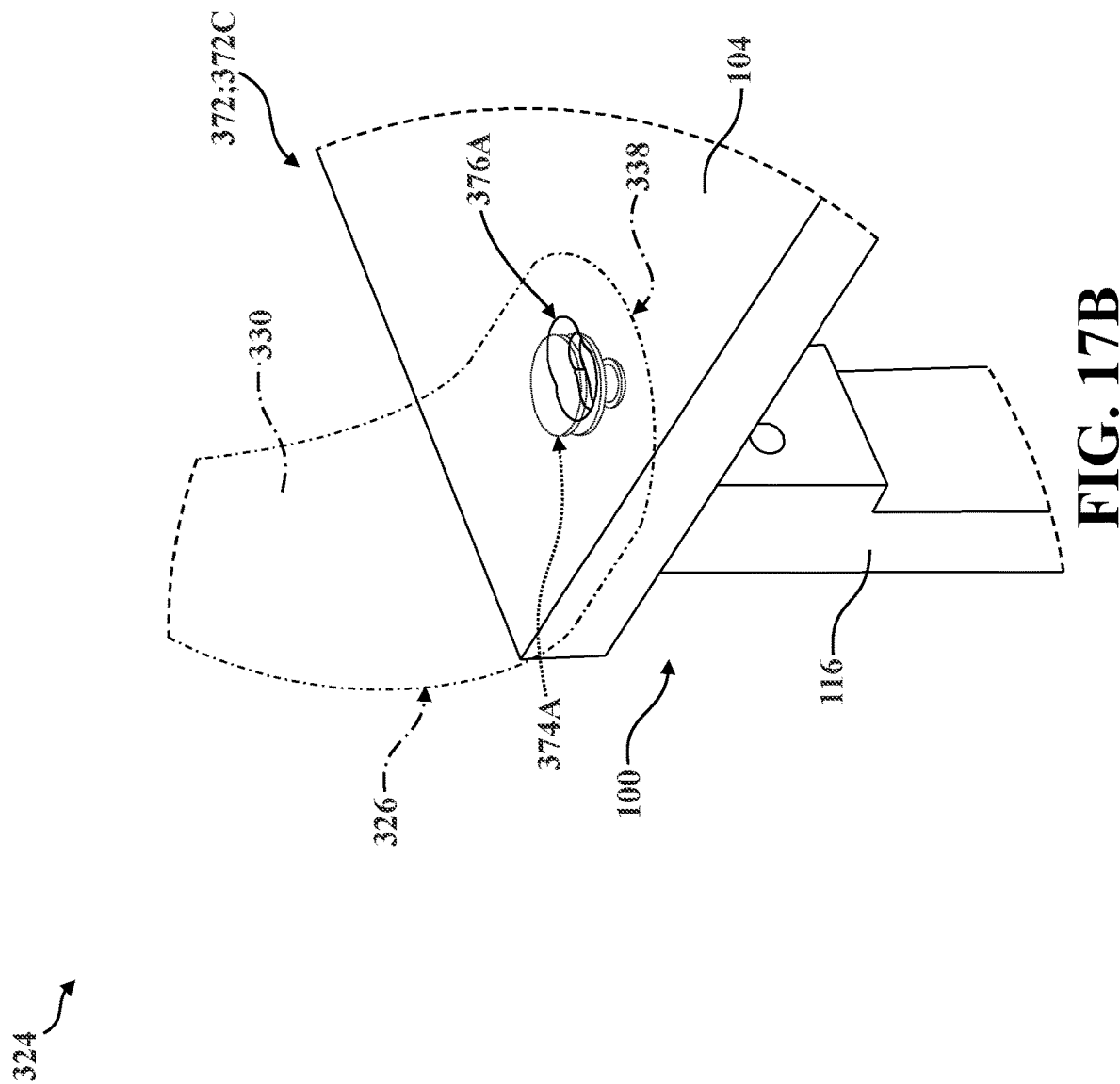
FIG. 17B is another partial perspective view of the components of the patient transport system of FIG. 17A, shown with the anchor inserted into the receiver.
Figure 17C:
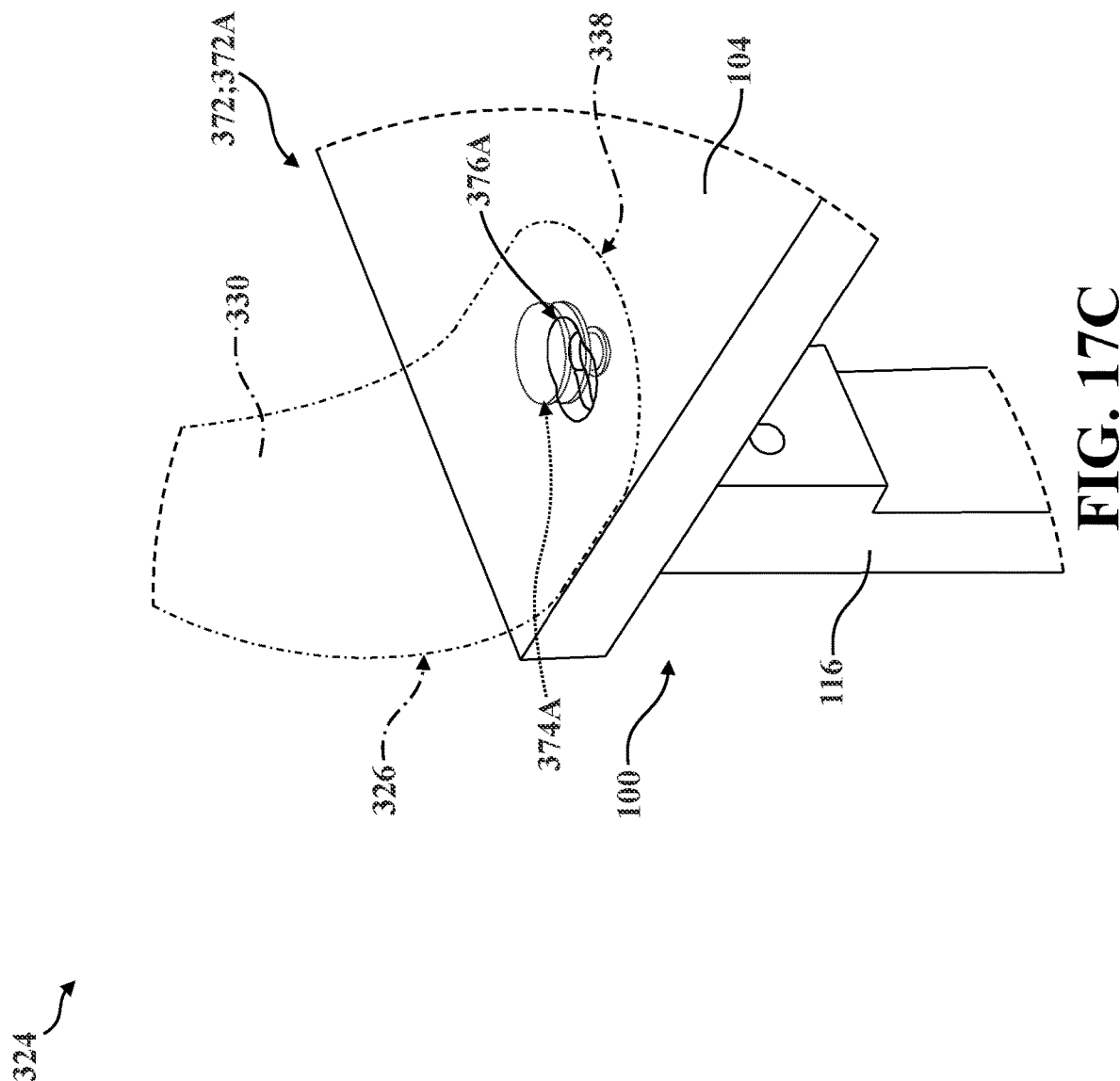
FIG. 17C is another partial perspective view of the components of the patient transport system of FIGS. 17A-17B, shown with the anchor secured to the receiver.

In the representative embodiments illustrated herein, and as is best depicted in FIG. 16, the tensioner assembly 354 generally includes a connection slide 356, a tensioner 358, an intermediate strap 360, and a keeper slide 362. In the illustrated embodiment, the connection slide 356 has or otherwise defines a first connection slide aperture 356A and a second connection slide aperture 356B (not shown in detail or identified in the drawings). Similarly, the keeper slide 362 has or otherwise defines a first keeper slide aperture 362A and a second keeper slide aperture 362B, and the tensioner 358 has or otherwise defines a first tensioner aperture 358A and a second tensioner aperture 358B (not shown in detail or identified in the drawings). The intermediate strap 360 has or otherwise defines a first end 364, a second end 366, and an intermediate region 368 extending between the first end 364 and the second end 366. However, and as will be appreciated from the subsequent description below, the tensioner assembly 354 could be configured in a number of different ways, and the connection slide 356, the tensioner 358, the intermediate strap 360, and/or the keeper slide 362 could be of a number of different styles, shapes, and/or configurations.

As is demonstrated in FIG. 16, the connection slide 356 is supported for movement along the connection region 334 of the first lower strap 326 (or, in some embodiments, of the second lower strap 328) between the thigh region 330 and the waist region 332. To this end, the connection region 334 extends through the first connection slide aperture 356A which, in the illustrated embodiment, has a substantially D-shaped profile. The first end 364 of the intermediate strap 360 is coupled to the connection slide 356 and, in the illustrated embodiments, is realized as a loop end secured to the second connection slide aperture 356B. In the illustrated embodiments, the second connection slide aperture 356B has a substantially rounded-rectangular profile. Similarly, the first and second keeper slide apertures 362A, 362B and the first and second tensioner apertures 358A, 358B also have substantially rounded-rectangular profiles in the illustrated embodiments. The keeper slide 362 is supported for movement along the intermediate region 368 of the intermediate strap 360 between the connection slide 356 and the tensioner 358. Here, the intermediate region 368 extends through the first tensioner aperture 358A, and then back through the second tensioner aperture 358B (not shown in detail). This arrangement facilitates adjustable movement of the tensioner 358 along the intermediate region 368 of the intermediate strap 360 relative to the connection slide 356 in order to adjust the tension between the first and second lower straps 326, 328, as noted above. In the representative embodiment illustrated herein, the tensioner 358 is realized as or otherwise comprises a strap lock that is formed integrally with the first connector 340 (e.g., with the lower buckle 346). However, it will be appreciated that other configurations are contemplated, and the tensioner assembly 354 could be configured with a tensioner 358 that is formed separately from the first connector 340 (or from the second connector 342 of the second tensioner assembly 354B; not shown in detail). Furthermore, it will be appreciated that the tensioner 358 could be of other types and/or styles. Other configurations are contemplated.

The second end 366 of the intermediate strap 360 is coupled to the keeper slide 362 and, in the illustrated embodiments, is realized as a loop end secured to the second keeper slide aperture 362B. This arrangement defines a loop 370 along the intermediate region 368 of the intermediate strap 360 between the tensioner 358 and the keeper slide 362. The loop 370 affords significant advantages for caregivers during the process of securing the patient, routing the straps, and adjusting tension between the first and second lower straps 326, 328 in that the second end 366 of the intermediate strap 360 is retained by the keeper slide 362. Here, the caregiver can manipulate the loop 370 and/or the tensioner 358 to adjust tension, and does not have to manage or relocate the second end 366 when the patient containment system 322 is used to secure relatively small patients. Put differently, the configuration afforded by the loop 370 prevents scenarios typical of conventional patient restraint straps, whereby the "free end" has to be tucked away or otherwise managed. Furthermore, in some embodiments, the loop 370 may be utilized to locate and/or retain the patient's hands or wrists during transport (not shown), which advantageously helps position the patient ideally for transport in certain use cases where there is less than optimal room on the lateral sides of the patient transport apparatus 100 (e.g., when traveling down a narrow stairwell).

Referring now to FIGS. 13A-18C, in the representative embodiment illustrated herein, the patient transport system 324 comprises a coupling system 372 to facilitate releasable attachment of portions of the patient containment system 322 to portions of the patient transport apparatus 100. To this end, the coupling system 372 generally comprises one or more anchors 374 and one or more receivers 376 shaped to releasably secure anchors 374. The coupling system 372 is operable between an engagement configuration 372A to at least partially limit movement of the anchor 374 relative to the receiver 376 (see FIGS. 17C and 18C), a disengagement configuration 372B to release the anchor 374 from the receiver 376 (see FIGS. 17A and 18A), and a transitional configuration 372C (see FIGS. 17B and 18B) to facilitate movement between the engagement configuration 372A and the disengagement configuration 372B. In the representative embodiments illustrated herein, and as is described in greater detail below, anchors 374 are operatively attached to portions of the first and second lower straps 326, 328 of the patient containment system 322, and receivers 376 are operatively attached to portions of the patient transport apparatus 100. However, it will be appreciated that this arrangement could be interchanged in part or in full (e.g., with one or more anchors 374 on the patient transport apparatus 100).

As is best depicted in FIG. 15B, the first lower strap 326 of the patient containment system 322 comprises a first thigh anchor 374A and a first waist anchor 374B, and the second lower strap 328 comprises a second thigh anchor 374C and a second waist anchor 374D. Furthermore, and as is best depicted in FIGS. 10 and 13A, the seat section 104 of the patient transport apparatus 100 comprises a first thigh receiver 376A and a second thigh receiver 376C (see FIG. 13A), and the back section 106 comprises a first waist receiver 376B and a second waist receiver 376D.

In the representative embodiment illustrated herein, the first and second thigh anchors 374A, 374C are operatively attached to the thigh regions 330 (e.g., arranged along the thigh regions 330, adjacent to the front lower strap ends 338, and the like) of the first and second lower straps 326, 328, respectively. Similarly, the first and second waist anchors 374B, 374D are operatively attached to the waist regions 332 (e.g., arranged along the waist regions 332, adjacent to the rear lower strap ends 336, and the like) of the first and second lower straps 326, 328, respectively.

Furthermore, in the representative embodiment illustrated herein, the first and second thigh receivers 376A, 376C are formed in the seat section 104 adjacent to the front struts 116 (see FIG. 13A), are spaced laterally from each other, and are arranged to receive the first and second thigh anchors 374A, 374C, respectively. The seat section 104 also defines a first seat aperture 378 and a second seat aperture 380 (see FIG. 13A) which, in some embodiments, facilitate attaching additional portions of the patient containment system 322 as described in greater detail below. In addition, in the representative embodiment illustrated herein, the first and second waist receivers 376B, 376D are formed in the back section 106 adjacent to the track assemblies 154 (see FIG. 10), are spaced laterally from each other, and are arranged to receive the first and second waist anchors 374B, 374D, respectively. The back section 106 also defines a first back aperture 382 and a second back aperture 384 (see FIG. 13A) which, in the illustrated embodiment, are shaped to respectively receive portions of the first and second lower straps 326, 328 therein adjacent to the waist regions 332 (see FIGS. 13B-14), and to permit the rear lower strap ends 336 to pass therethrough.

Figure 18A:
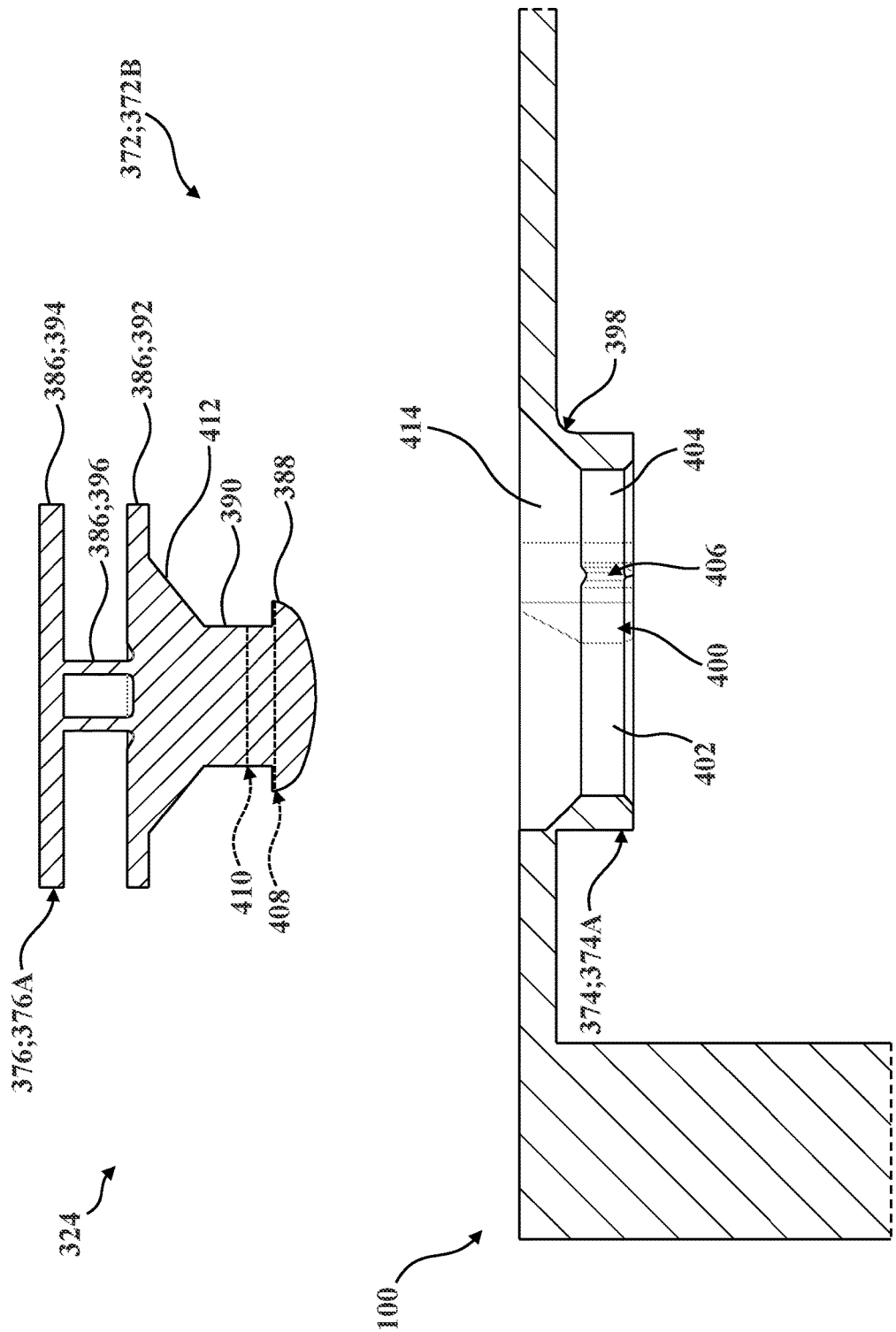
FIG. 18A is a partial sectional view taken generally longitudinally through the receiver of FIG. 17A, shown with the anchor positioned vertically above the receiver.
Figure 18B:
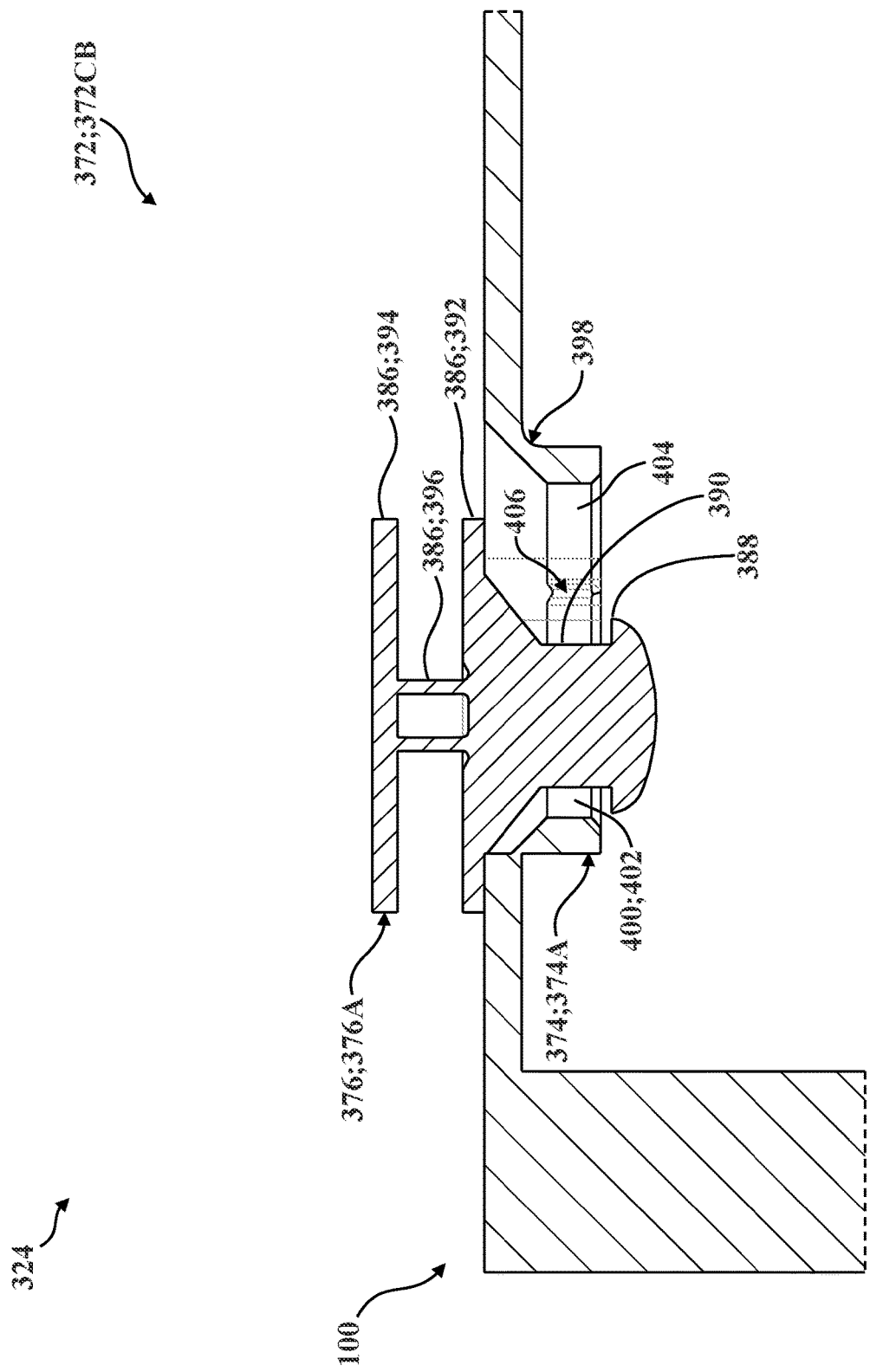
FIG. 18B is a partial sectional view taken generally longitudinally through the receiver of FIG. 17B, shown with the anchor inserted into the receiver.
Figure 18C:
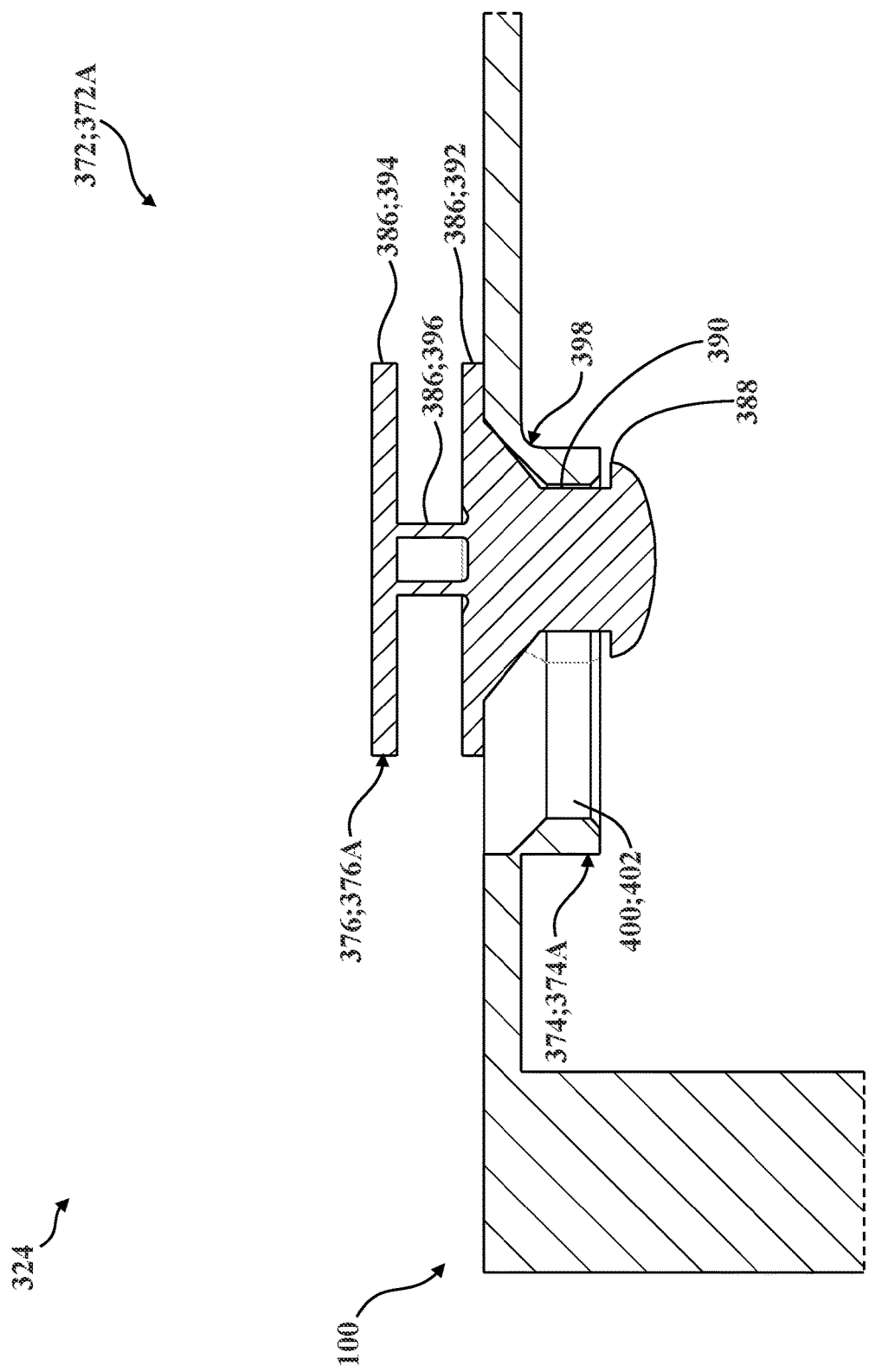
FIG. 18C is a partial sectional view taken generally longitudinally through the receiver of FIG. 17C, shown with the anchor secured to the receiver.

As is best depicted in FIGS. 18A-18C, in the representative embodiment illustrated herein, the anchors 374 each comprise an anchor base 386, an anchor head 388, and an anchor shaft 390 extending between the anchor base 386 and the anchor head 388. In some embodiments, the anchor base 386 may comprise a lower base portion 392 and an upper base portion 394 with a base connector portion 396 extending therebetween (see FIG. 18A). Here, the lower and upper base portions 394 have generally annular profiles and are configured to abut opposing surfaces of the first lower strap 326 (or the second lower strap 328), and the base connector portion 396 extends through an aperture or hole (not shown) formed in the first lower strap 326 (or the second lower strap 328). Here, it is contemplated that the upper base portion 394 could be realized as a washer, and the base connector portion 396 could be realized as a rivet employed to couple the upper base portion 394 and the first lower strap 326 (or the second lower strap 328) to the lower base portion 392. Here too, the upper base portion 394 could be defined by a part of a rivet. In any event, the anchors 374 are depicted as unitary, once-piece components throughout the drawings for illustrative purposes, and other configurations are contemplated.

With continued reference to FIGS. 17A-18C, in the representative embodiment illustrated herein, the receivers 376 each comprise a receiver body 398 defining a receiver aperture 400. The receiver aperture 400 has a first aperture region 402 shaped to receive the anchor head 388 of the anchor 374 therethrough, and a second aperture region 404 shaped to receive the anchor shaft 390 therein. In some embodiments, one or more of the receivers 376 may comprise a tab 406 formed extending into the receiver aperture 400 and arranged adjacent to the second aperture region 404 to at least partially restrict movement of the anchor shaft 390 between the second aperture region 404 and the first aperture region 402. Put differently, the tab 406 helps retain the coupling system 372 in the engagement configuration 372A (see FIG. 18C) by creating resistance to movement of the anchor shaft 390 from the second aperture region 404 to the first aperture region 402.

As is best depicted schematically in FIG. 18A, the anchor head 388 is sized radially larger than the anchor shaft 390. In some embodiments, the anchor head 388 may define a head perimeter 408, and the anchor shaft 390 may define a shaft perimeter 410 that is smaller than the head perimeter 408. Here, the first aperture region 402 and the second aperture region 404 are sized relative to the head perimeter 408 such that the anchor head 388 can pass through the first aperture region 402 (e.g., in a vertical direction; compare FIGS. 18A and 18B), but cannot pass through the second aperture region 404. In the illustrated embodiments, the anchors 374 are also provided with a frustoconical region 412 which is disposed between the anchor base 386 and the anchor shaft 390, and the receivers 376 include tapered profiles leading into the receiver apertures 400 to abut the frustoconical regions 412. This arrangement allows for bearing contact which can be used to facilitate adjusting the first and second lower straps 326, 328 between different orientations, angles, and the like.

Referring now to FIGS. 13B-15B, in some embodiments, the patient containment system 322 may comprise a first upper strap 416 and a second upper strap 418 each having a respective seat end 420, back end 422, and shoulder region 424 extending between the seat end 420 and the back end 422. The seat end 420 is configured to releasably secure to the seat section 104 of the patient transport apparatus 100. More specifically, in the representative embodiment illustrated herein, the first and second seat apertures 378, 380 each define a strap mount 426 that is shaped to receive the back end 422 of one of the first and second upper straps 416, 418 therethrough, and the seat ends 420 each define a pass-through loop 428 shaped to receive the back end 422 therethrough to releasably secure the first and second upper straps 416, 418 to the strap mounts 426 defined by the first and second seat apertures 378, 380. However, it will be appreciated that other configurations are contemplated.

As shown in FIG. 14, in the representative embodiment illustrated herein, the patient transport apparatus 100 comprises first and second webbing adjusters 430, 432 operatively attached to the back section 106, disposed vertically above the first and second back apertures 382, 384, and shaped to receive the back ends 422 of the first and second upper straps 416, 418, respectively, therethrough. Here, the first and second webbing adjusters 430, 432 are configured to releasably engage the shoulder regions 424 of the first and second upper straps 416, 418, respectively, to adjust tension in the first and second upper straps 416, 418 (e.g., between the first and second webbing adjusters 430, 432 and the respective seat ends 420). It will be appreciated that the first and second webbing adjusters 430, 432 could be configured in a number of different ways sufficient to engage the shoulder regions 424 of the first and second upper straps 416, 418.

In the representative embodiments illustrated herein, the first and second upper straps 416, 418 each comprise a strap handle 434 coupled to the shoulder region 424 and arranged for engagement by the patient. Here, the patient can grasp the strap handles 434 during transport. Furthermore, if the patient has a decreased level of consciousness, the caregiver may use the strap handles 434 to locate and/or retain the patient's hands or wrists during transport (not shown), which advantageously helps position the patient ideally for transport in certain use cases where there is less than optimal room on the lateral sides of the patient transport apparatus 100 (e.g., when traveling down a narrow stairwell).

In some embodiments, the first upper strap 416 (and/or the second upper strap 418) may comprise a first magnetic element, and the patient transport apparatus 100 may comprise a second magnetic element 438 arranged to releasably attach to the first magnetic element 436 to at partially restrict movement of the first upper strap 416 (and/or the second upper strap 418) relative to the patient transport apparatus 100 in an absence of engagement occurring between the first webbing adjuster 430 (and/or the second webbing adjuster 432) and the shoulder region 424 (see FIG. 14; not shown in detail). This configuration helps the caregiver route and/or manage the first and second upper straps 416, 418 during the process of securing the patient to the patient transport apparatus 100 (or releasing the patient from the patient transport apparatus 100) with the patient containment system 322. In some embodiments, one or more of the first magnetic element 436 and the second magnetic element 438 may comprise a magnet. In some embodiments, one of the first magnetic element 436 and the second magnetic element may comprise a ferrous material. Other configurations are contemplated.

As is best shown in FIGS. 15A-15B, in some embodiments, a first shoulder connector 440 is coupled to the shoulder region 424 of the first upper strap 416 via an extension strap (not shown in detail), and a second shoulder connector 442 is coupled to the shoulder region 424 of the second upper strap 418 via another extension strap (not shown in detail). The second shoulder connector 442 is configured to releasably attach to the first shoulder connector 440 to at least partially limit movement of the first upper strap 416 relative to the second upper strap 418 (and/or relative to each other). In the representative embodiment illustrated herein, one of the first and second shoulder connectors 440, 442 is realized as an upper clasp 444, and the other of the first and second shoulder connectors 440, 442 is realized as an upper buckle 446 configured to releasably secure to the upper clasp 444. However, it will be appreciated that the first and second shoulder connectors 440, 442 could be configured in a number of different ways sufficient to limit movement between the first and second upper straps 416, 418.

In the representative embodiment illustrated herein, the lower clasp 355 and the lower buckle 346 are of a first connector configuration 448, and the upper clasp 444 and the upper buckle 446 are of a second connector configuration 450 that is different from the first connector configuration 448. To this end, in some embodiments, the first connector configuration 448 defines a first connector width 452, and the second connector configuration 450 defines a second connector width 454 that is less than the first connector width 452. In some embodiments, the first connector width 452 is approximately 2-inches. It will be appreciated that the first connector configuration 448 being different from the second connector configuration 450 helps to prevent the first shoulder connector 440 or the second shoulder connector 442 from being attached to the first connector 340 or the second connector 342. This arrangement further promotes improved strap management and usability of the patient containment system 322 by preventing incorrect attachment. Similarly, in some embodiments, one or more components of the patient containment system 322 may include an identification indicia 456 (see FIG. 15B). The identification indicia 456 may be designated colors, symbols, numbers, letters, tactile patterns, or a combination thereof. The identification indicia 456 may be any identifying visual element or tactile surface which allows a user to easily identify each of the straps 326, 328, 416, 418 from one another.

It will be appreciated that the patient containment system 322 may comprise additional straps, sections, and the like to facilitate securing a patient for transport on the patient transport apparatus 100. For example, additional straps may be provided to wrap around the patient's chest. Other configurations are contemplated. In some embodiments, a strap management box (not shown) may be coupled to the patient transport apparatus 100 to stow one or more components of the patient containment system 322 when not in use.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient transport system comprising:
a patient transport apparatus comprising a seat section and a back section for supporting the patient;
a patient containment system comprising:
an upper strap having a seat end coupled to said seat section, a back end, and a shoulder region extending between said seat end and said back end;
a lower strap having a thigh region, a waist region, and a connection region arranged between said thigh region and said waist region, wherein said connection region defines a connection width and said thigh region defines a thigh width larger than said connection width;
a connector coupled to said connection region of said lower strap; and
a coupling system to facilitate releasable attachment of said patient containment system to said patient transport apparatus, said coupling system comprising:
an anchor operatively attached to one of said patient transport apparatus and said lower strap;
a receiver shaped to releasably secure said anchor, said receiver operatively attached to the other of said patient transport apparatus and said lower strap; and
wherein said coupling system is operable between:
an engagement configuration to at least partially limit movement of said anchor relative said receiver; and
a disengagement configuration to release said anchor from said receiver;
wherein said seat section defines a strap mount shaped to receive said back end of said upper strap therethrough; and
wherein said seat end of said upper strap comprises a pass-through loop shaped to receive said back end of said upper strap therethrough to releasably secure said upper strap to said strap mount.

2. The patient transport system as set forth in claim 1, wherein said anchor comprises an anchor base, an anchor head, and an anchor shaft extending between said anchor base and said anchor shaft; and
wherein said receiver comprises a receiver body defining a receiver aperture having a first aperture region shaped to receive said anchor head therethrough, and having a second aperture region disposed in communication with said first aperture region and being shaped to receive said anchor shaft therein.

3. The patient transport system as set forth in claim 2, wherein said receiver further comprises a tab formed extending into said receiver aperture and arranged adjacent to said second aperture region to at least partially restrict movement of said anchor shaft between said second aperture region and said first aperture region.

4. The patient transport system as set forth in claim 1, wherein said patient transport apparatus further comprises a seat section and a back section for supporting the patient;
wherein said anchor is further defined as a thigh anchor operatively attached to said thigh region of said lower strap;
wherein said receiver is further defined as a thigh receiver operatively attached to said seat section of said patient transport apparatus; and
wherein said coupling system further comprises:
a waist anchor operatively attached to said waist region of said lower strap; and
a waist receiver shaped to releasably secure said waist anchor in said engagement configuration, said waist receiver operatively attached to said back section of said patient transport apparatus.

5. The patient transport system as set forth in claim 1, wherein said patient transport apparatus further comprises a webbing adjuster operatively attached to said back section and shaped to receive said back end of said upper strap therethrough, said webbing adjuster being configured to releasably engage and said shoulder region of said upper strap to adjust tension in said upper strap between said webbing adjuster and said seat end;
wherein said upper strap further comprises a first magnetic element; and
wherein said patient transport apparatus further comprises a second magnetic element arranged to releasably attach to said first magnetic element to at least partially restrict movement of said upper strap relative to said patient transport apparatus in an absence of engagement occurring between said webbing adjuster and said shoulder region of said upper strap.

6. The patient transport system as set forth in claim 1, wherein said upper strap further comprises a strap handle coupled to said shoulder region, said strap handle being arranged for engagement by the patient.

7. The patient transport system as set forth in claim 1, wherein said lower strap is further defined as a first lower strap, said connector is further defined as a first connector, and said upper strap is further defined as a first upper strap; and
wherein said patient containment system further comprises:
a second lower strap having a connection region arranged between a thigh region and a waist region;
a second connector coupled to said connection region of said second lower strap and configured to releasably attach to said first connector to at least partially limit movement of said first lower strap relative to said second lower strap; and
a second upper strap having a shoulder region arranged between a seat end and a back end.

8. The patient transport system as set forth in claim 7, wherein said patient containment system further comprises:
a first shoulder connector coupled to said shoulder region of said first upper strap, and
a second shoulder connector coupled to said shoulder region of said second upper strap and configured to releasably attach to said first shoulder connector to at least partially limit movement of said first upper strap relative to said second upper strap;
wherein one of said first connector and said second connector comprises a lower clasp, and the other of said first connector and said second connector comprises a lower buckle;
wherein one of said first shoulder connector and said second shoulder connector comprises an upper clasp, and the other of said first shoulder connector and said second shoulder connector comprises an upper buckle;

wherein said lower clasp and said lower buckle are of a first connector configuration; and
wherein said upper clasp and said upper buckle are of a second connector configuration different from said first connector configuration.

9. The patient transport system as set forth in claim 7, wherein one or more of said first upper strap, said second upper strap, said first lower strap, and said second lower strap comprises an identification indicia.

10. A patient transport system comprising:
a patient transport apparatus comprising a seat section and a back section for supporting the patient;
a patient containment system comprising:
an upper strap having a seat end coupled to said seat section, a back end, a shoulder region extending between said seat end and said back end, and a strap handle coupled to said shoulder region and arranged for engagement by the patient;
a lower strap having a thigh region, a waist region, and a connection region arranged between said thigh region and said waist region, wherein said connection region defines a connection width and said thigh region defines a thigh width larger than said connection width;
a connector coupled to said connection region of said lower strap; and
a coupling system to facilitate releasable attachment of said patient containment system to said patient transport apparatus, said coupling system comprising:
an anchor operatively attached to one of said patient transport apparatus and said lower strap;
a receiver shaped to releasably secure said anchor, said receiver operatively attached to the other of said patient transport apparatus and said lower strap; and
wherein said coupling system is operable between:
an engagement configuration to at least partially limit movement of said anchor relative said receiver; and
a disengagement configuration to release said anchor from said receiver.

11. The patient transport system as set forth in claim 10, wherein said anchor comprises an anchor base, an anchor head, and an anchor shaft extending between said anchor base and said anchor shaft; and
wherein said receiver comprises a receiver body defining a receiver aperture having a first aperture region shaped to receive said anchor head therethrough, and having a second aperture region disposed in communication with said first aperture region and being shaped to receive said anchor shaft therein.

12. The patient transport system as set forth in claim 11, wherein said receiver further comprises a tab formed extending into said receiver aperture and arranged adjacent to said second aperture region to at least partially restrict movement of said anchor shaft between said second aperture region and said first aperture region.

13. The patient transport system as set forth in claim 10, wherein said patient transport apparatus further comprises a seat section and a back section for supporting the patient;
wherein said anchor is further defined as a thigh anchor operatively attached to said thigh region of said lower strap;
wherein said receiver is further defined as a thigh receiver operatively attached to said seat section of said patient transport apparatus; and
wherein said coupling system further comprises:
a waist anchor operatively attached to said waist region of said lower strap; and
a waist receiver shaped to releasably secure said waist anchor in said engagement configuration, said waist receiver operatively attached to said back section of said patient transport apparatus.

14. The patient transport system as set forth in claim 10, wherein said seat section defines a strap mount shaped to receive said back end of said upper strap therethrough; and
wherein said seat end of said upper strap comprises a pass-through loop shaped to receive said back end of said upper strap therethrough to releasably secure said upper strap to said strap mount.

15. The patient transport system as set forth in claim 10, wherein said patient transport apparatus further comprises a webbing adjuster operatively attached to said back section and shaped to receive said back end of said upper strap therethrough, said webbing adjuster being configured to releasably engage and said shoulder region of said upper strap to adjust tension in said upper strap between said webbing adjuster and said seat end;
wherein said upper strap further comprises a first magnetic element; and
wherein said patient transport apparatus further comprises a second magnetic element arranged to releasably attach to said first magnetic element to at least partially restrict movement of said upper strap relative to said patient transport apparatus in an absence of engagement occurring between said webbing adjuster and said shoulder region of said upper strap.

16. The patient transport system as set forth in claim 10, wherein said lower strap is further defined as a first lower strap, said connector is further defined as a first connector, and said upper strap is further defined as a first upper strap; and
wherein said patient containment system further comprises:
a second lower strap having a connection region arranged between a thigh region and a waist region;
a second connector coupled to said connection region of said second lower strap and configured to releasably attach to said first connector to at least partially limit movement of said first lower strap relative to said second lower strap; and
a second upper strap having a shoulder region arranged between a seat end and a back end.

17. The patient transport system as set forth in claim 16, wherein said patient containment system further comprises:
a first shoulder connector coupled to said shoulder region of said first upper strap, and
a second shoulder connector coupled to said shoulder region of said second upper strap and configured to releasably attach to said first shoulder connector to at least partially limit movement of said first upper strap relative to said second upper strap;
wherein one of said first connector and said second connector comprises a lower clasp, and the other of said first connector and said second connector comprises a lower buckle;
wherein one of said first shoulder connector and said second shoulder connector comprises an upper clasp, and the other of said first shoulder connector and said second shoulder connector comprises an upper buckle;
wherein said lower clasp and said lower buckle are of a first connector configuration; and wherein said upper clasp and said upper buckle are of a second connector configuration different from said first connector configuration.

18. The patient transport system as set forth in claim 16, wherein one or more of said first upper strap, said second upper strap, said first lower strap, and said second lower strap comprises an identification indicia.

19. A patient transport system comprising:
a patient transport apparatus comprising a seat section and a back section for supporting the patient;
a patient containment system comprising:
an upper strap having a seat end coupled to said seat section, a back end, and a shoulder region extending between said seat end and said back end;
a lower strap having a thigh region, a waist region, and a connection region arranged between said thigh region and said waist region, wherein said connection region defines a connection width and said thigh region defines a thigh width larger than said connection width;
a connector coupled to said connection region of said lower strap; and
a coupling system to facilitate releasable attachment of said patient containment system to said patient transport apparatus, said coupling system comprising:
an anchor operatively attached to one of said patient transport apparatus and said lower strap;
a receiver shaped to releasably secure said anchor, said receiver operatively attached to the other of said patient transport apparatus and said lower strap; and
wherein said coupling system is operable between:
an engagement configuration to at least partially limit movement of said anchor relative said receiver; and
a disengagement configuration to release said anchor from said receiver;
wherein said patient transport apparatus further comprises a webbing adjuster operatively attached to said back section and shaped to receive said back end of said upper strap therethrough, said webbing adjuster being configured to releasably engage and said shoulder region of said upper strap to adjust tension in said upper strap between said webbing adjuster and said seat end;
wherein said upper strap further comprises a first magnetic element; and
wherein said patient transport apparatus further comprises a second magnetic element arranged to releasably attach to said first magnetic element to at least partially restrict movement of said upper strap relative to said patient transport apparatus in an absence of engagement occurring between said webbing adjuster and said shoulder region of said upper strap.

* * * * *